US011125749B2

(12) United States Patent
Pulitzer et al.

(10) Patent No.: US 11,125,749 B2
(45) Date of Patent: Sep. 21, 2021

(54) SYSTEM AND METHOD FOR REMOTE COLORIMETRY AND RATIOMETRIC COMPARISON AND QUANTIFICATION IN ANALYSIS OF MEDICAL TEST RESULTS

(71) Applicant: RELIANT IMMUNE DIAGNOSTICS, INC., Austin, TX (US)

(72) Inventors: Jovan Hutton Pulitzer, Frisco, TX (US); Henry Joseph Legere, III, Austin, TX (US)

(73) Assignee: Reliant Immune Diagnostics, Inc., Austin, TX (US)

( * ) Notice: Subject to any disclaimer, the term of this patent is extended or adjusted under 35 U.S.C. 154(b) by 188 days.

(21) Appl. No.: 16/001,771

(22) Filed: Jun. 6, 2018

(65) Prior Publication Data
US 2019/0376966 A1     Dec. 12, 2019

(51) Int. Cl.
*G01N 33/558* (2006.01)
*G01N 33/569* (2006.01)
(Continued)

(52) U.S. Cl.
CPC ......... *G01N 33/558* (2013.01); *G01N 31/22* (2013.01); *G01N 33/492* (2013.01);
(Continued)

(58) Field of Classification Search
None
See application file for complete search history.

(56) References Cited

U.S. PATENT DOCUMENTS 5,587,061 A     12/1996  Chen
5,709,788 A     1/1998   Chen
(Continued)

FOREIGN PATENT DOCUMENTS

CN     105954512 A     9/2016
WO     2010118124 A2   10/2010
(Continued)

OTHER PUBLICATIONS

Rajandran et al., Smartphone based bacterial detection using biofunctionalized fluorescent nanoparticles, Microchim Acta, vol. 181, pp. 1815-1821. (Year: 2014).*
(Continued)

*Primary Examiner* — Melanie Brown

(57) ABSTRACT

A system for providing colorimetric and ratiometric comparison and quantification for medical test results, comprising a testing device including an alignment target and including a plurality of immunoassay test strips, the plurality of immunoassay test strips each including a test line and a control line, and a colorimetry device configured to operate with a mobile device, the mobile device including a camera and a software application stored thereon, wherein the software application provides executable instructions to detect color properties of a color of the test line and a color of a control line of at least one of the plurality of immunoassay test strips, determine a risk value for each of at least one disease risks tested using the biologic sample, wherein the risk value is a rating determined from the color properties of the color of the test line, and provide medical test results based on the risk value.

9 Claims, 45 Drawing Sheets

(51) Int. Cl.
| | |
|---|---|
| G01N 33/49 | (2006.01) |
| G01N 31/22 | (2006.01) |
| G01N 21/78 | (2006.01) |
| G01N 33/50 | (2006.01) |

(52) U.S. Cl.
CPC .......... *G01N 33/569* (2013.01); *G01N 21/78* (2013.01); *G01N 33/5005* (2013.01); *G01N 2333/185* (2013.01); *G01N 2333/471* (2013.01)

(56) References Cited

U.S. PATENT DOCUMENTS

| | | | |
|---|---|---|---|
| 5,904,826 | A | 5/1999 | Chen |
| 6,149,865 | A | 11/2000 | Hsu |
| 7,090,802 | B1 | 8/2006 | Wang |
| 7,235,098 | B2 | 6/2007 | Palmaz |
| 8,308,452 | B2 | 11/2012 | Amirouche et al. |
| 8,506,901 | B2 | 8/2013 | Chen et al. |
| 8,655,009 | B2 | 2/2014 | Chen et al. |
| 8,807,169 | B2 | 8/2014 | Amirouche et al. |
| 8,877,140 | B2 | 11/2014 | Chen et al. |
| 8,911,679 | B2 | 12/2014 | Chen et al. |
| 9,285,323 | B2 | 3/2016 | Burg et al. |
| 9,390,237 | B2 | 6/2016 | Myers et al. |
| 9,523,358 | B2 | 12/2016 | Amirouche et al. |
| 9,569,858 | B2 | 2/2017 | Babcock et al. |
| 9,607,380 | B2 | 3/2017 | Burg et al. |
| 9,726,161 | B2 | 8/2017 | Kim et al. |
| 9,857,373 | B1* | 1/2018 | Pulitzer ................ G01N 33/558 |
| 2002/0134682 | A1 | 9/2002 | Chen |
| 2003/0207458 | A1 | 11/2003 | Sookbumroong |
| 2005/0266582 | A1 | 12/2005 | Modlin et al. |
| 2006/0014302 | A1 | 1/2006 | Martinez |
| 2006/0222567 | A1 | 10/2006 | Kloepfer et al. |
| 2006/0245933 | A1 | 11/2006 | Balch |
| 2008/0070599 | A1 | 3/2008 | Apodaca |
| 2008/0118397 | A1 | 5/2008 | Slowey |
| 2009/0298191 | A1 | 12/2009 | Whitesides et al. |
| 2011/0077971 | A1 | 3/2011 | Surwit |
| 2012/0082598 | A1 | 4/2012 | Baydoun |
| 2013/0161190 | A1 | 6/2013 | Ewart et al. |
| 2013/0189794 | A1 | 7/2013 | Emeric et al. |
| 2013/0203043 | A1* | 8/2013 | Ozcan .................. G06F 16/245 435/5 |
| 2013/0273528 | A1 | 10/2013 | Ehrenkranz |
| 2014/0051173 | A1 | 2/2014 | Barstis et al. |
| 2014/0072189 | A1 | 3/2014 | Jena |
| 2014/0089006 | A1 | 3/2014 | Abreu |
| 2014/0121487 | A1 | 5/2014 | Faybishenko et al. |
| 2014/0170679 | A1 | 6/2014 | Aitchison |
| 2015/0056719 | A1 | 2/2015 | Karlovac |
| 2015/0359458 | A1 | 12/2015 | Erickson et al. |
| 2016/0077091 | A1 | 3/2016 | Tyrrell et al. |
| 2016/0223536 | A1 | 8/2016 | Johnson et al. |
| 2016/0349185 | A1* | 12/2016 | Park ....................... G01N 21/78 |
| 2017/0059566 | A1 | 3/2017 | Reed et al. |
| 2017/0089893 | A1 | 3/2017 | Legere, III |
| 2017/0154438 | A1* | 6/2017 | Kisner .................... G06T 5/001 |

FOREIGN PATENT DOCUMENTS

| | | |
|---|---|---|
| WO | 2013158504 A1 | 10/2013 |
| WO | 2015143309 A1 | 9/2015 |

OTHER PUBLICATIONS

Hou et al., Smartphone-Based Dual-Modality Imaging System for Quantitative Detection of Color or Fluorescent Lateral Flow Immunochromatographic Strips, Nanoscale Research Letters, vol. 12, pp. 1-13. (Year: 2017).*

Lee et al., A Low-Cost, High-Performance System for Fluorescence Lateral Flow Assays, Biosensors, vol. 3, pp. 360-373. (Year: 2013).*

Brown, M. C. et al. (2009). Lateral Flow Immunoassay. Tse, H. Y., Wong, R. C. (Eds.). New York, NY: Humana Press.

Baltekin O., et al. (Aug. 22, 2017). Antibiotic susceptibility testing in less than 30 min using direct single-cell imaging. Proceedings of the National Academy of Sciences. 114(34).

Mudanyali, O. et al. Integrated Rapid-Diagnostic-Test Reader Platform on a Cellphone. Lab on a Chip, vol. 12, No. 15. Aug. 7, 2012; pp. 7, 12.

FisherSCI. Anti-Zika virus ELISA (IgM) test instruction. Sep. 2, 2016.

Acharya, D. et al. An ultrasensitive electrogenerated chemiluminescence-based immunoassay for specific detection of Zika virus. Scientific Reports 6, Article No. 32227. Aug. 2016.

International Search Report and Written Opinion of the International Searching Authority from PCT/US17/57037, dated Dec. 28, 2017.

International Search Report and Written Opinion of the International Searching Authority from PCT/US17/57039, dated Dec. 26, 2017.

International Search Report and Written Opinion of the International Searching Authority from PCT/US17/57041, dated Dec. 14, 2017.

International Search Report and Written Opinion of the International Searching Authority from PCT/US17/60252, dated Jan. 12, 2018.

International Search Report and Written Opinion of the International Searching Authority from PCT/US17/66528, dated Mar. 7, 2018.

Jianjun Li et al. Application of Microfluidic Devices to Proteomics Research. Journal: Molecular & Cellular Proteomics Jan. 3, 2002. 1:157-168. Canada.

Kling A. et. al. Electrochemical microfluidic platform for simultaneous multianalyte detection. Article, 2015, 916-919, Europe.

Andre Kling et al. Multianalyte Antibiotic Detection on an Electrochemical Microfluidic Platform. Article. Jul. 19, 2016, 10036-10043, Germany.

Meichei Wang Kadlec et. al. A Cell Phone—Based Microphotometric System for Rapid Antimicrobial Susceptibility Testing. Journal. 2014, vol. 19 (3) 258-266. Tucson, AZ.

Hongying Zhu et. al. Cost-effective and compact wide-field fluorescent imaging on a cell-phone. Article. Jan. 21, 2011. 315-322, 11(2). California.

Moffitt Jeffrey R. et. al. The single-cell chemostat: an agarose-based, microfluidic device for high-throughput, single-cell studies of bacteria and bacterial communities. Article. Oct. 24, 2017. 21pgs. 12(8).

Temiz Yuksel et al. Microelectronic Engineering. Article. 2015. 156-175. Published by Elsevier B.V. Switzerland.

Vasdekis Andreas et al. Review of methods to probe single cell metabolism and bioenergetics, Journal, Jan. 20151. 115-135. Published by Elsevier.

Wang Shuqi et al. Portable microfluidic chip for detection of *Escherichia coli* produce and blood. International Journal of Nanomedicine. May 27, 2012. 2012:7 2591-2600. MA.

Hoylandm James Donaldson. Microfluidic chip and connector. Nov. 11, 2012, 16pgs. Europe.

Baltekin Ozden et al. Antibiotic susceptibility testing in less than 30 min using direct single-cell imaging. Aug. 22, 2017. 9170-9175 vol. 114-34.

Ashraf Muhammad Waseem. Micro Electromechanical Systems (MEMS) Based Microfluidic Devices for Biomedical Applications. Journal : Molecular Sciences. Jun. 7, 2011. 3648-3704.

U. Hassan et al, A microfluidic biochip for complete blood cell counts at the point-of-care, Dec. 2015, 201-213, 3(4).

Au K. Anthony et al, Microvalves and Micropumps for BioMEMS, May 24, 2011, 179-220.

Sticker Drago et al, Multi-layered, membrane-integrated microfluidics based on replica molding of a thiol-ene epoxy thermoset for . . . Article, Nov. 2015, 4542-4554.

Shaegh et al, Plug-and-play microvalve and micropump for rapid integration with microfluidic chips, Article, Apr. 22, 2015, 557-564, Massachusetts, Springer Berlin Heidelberg.

(56) References Cited

OTHER PUBLICATIONS

Schafer Dawn et al, Microfluidic cell counter with embedded optical fibers fabricated by femtosecond laser ablation and anodic bonding, Article, Apr. 13, 2009, 17(8), 6068-6073, Colorado.
Hassan U. et al, A microfluidic biochip for complete blood cell counts at the point-of-care, Dec. 2015, 201-213. 3(4).

* cited by examiner

SYSTEM AND METHOD FOR REMOTE COLORIMETRY AND RATIOMETRIC COMPARISON AND QUANTIFICATION IN ANALYSIS OF MEDICAL TEST RESULTS

TECHNICAL FIELD

The following disclosure is related to a system and method for initiating a telemedicine conference in response to diagnostic test results.

SUMMARY

A system for providing colorimetric and ratiometric comparison and quantification for medical test results is provided. The system comprises a testing device including thereon an alignment target and including a plurality of immunoassay test strips, the plurality of immunoassay test strips each including a sample pad capable of receiving a biologic sample, a conjugate pad containing particles for conjugating with antibodies or antigens present in the biologic sample, and a membrane strip including a test line and a control line, wherein the test line and the control line are viewable, a colorimetry device configured to operate with a mobile device, the mobile device including a camera, a viewing screen, and a software application stored thereon, wherein the software application provides executable instructions to receive a test selection, issue a notification concerning use of the colorimetry device and instructions regarding configuration of the colorimetry device, initiate operation of the camera of the mobile device, present on the viewing screen of the mobile device an alignment graphic to be aligned with the alignment target of the testing device, detect when an alignment of the alignment graphic and the alignment target has taken place, capture an image of the testing device in response to detecting the alignment of the alignment graphic and the alignment target, detect color properties of a color of the test line and a color of a control line of at least one of the plurality of immunoassay test strips, transmit the image and color properties to a server, determine a risk value for each of at least one disease risks tested using the biologic sample, wherein the risk value is a rating determined from the color properties of the color of the test line, and provide medical test results based on the risk value.

A method for providing colorimetric and ratiometric comparison and quantification for medical test results is provided. The method comprises collecting at least one biologic sample by a testing device including thereon an alignment target and including a plurality of immunoassay test strips, conjugating the at least one biologic sample with particles on a conjugate pad on at least one of the plurality of immunoassay test strips to create an immune complex, binding antigens or antibodies of the immune complex to antigens or antibodies of a test line of at least one of the plurality of immunoassay test strips, providing a software application to be stored on a mobile device, the mobile device including a camera and a viewing screen, providing a colorimetry device configured to operate with the mobile device, receiving a test selection via the software application, issuing by the software application a notification concerning use of the colorimetry device and instructions regarding configuration of the colorimetry device, initiating operation of the camera, presenting on the viewing screen an alignment graphic to be aligned with the alignment target of the testing device, detecting when an alignment of the alignment graphic and the alignment target has taken place, capturing an image of the testing device in response to detecting the alignment of the alignment graphic and the alignment target, detecting color properties of a color of the test line and a color of a control line of at least one of the plurality of immunoassay test strips, transmitting the image and color properties to a server, determining a risk value for each of at least one disease risks tested using the biologic sample, wherein the risk value is a rating determined from the color properties of the color of the test line, and providing medical test results based on the risk value.

BRIEF DESCRIPTION OF THE DRAWINGS

For a more complete understanding, reference is now made to the following description taken in conjunction with the accompanying Drawings in which.

DETAILED DESCRIPTION

Figure 1:
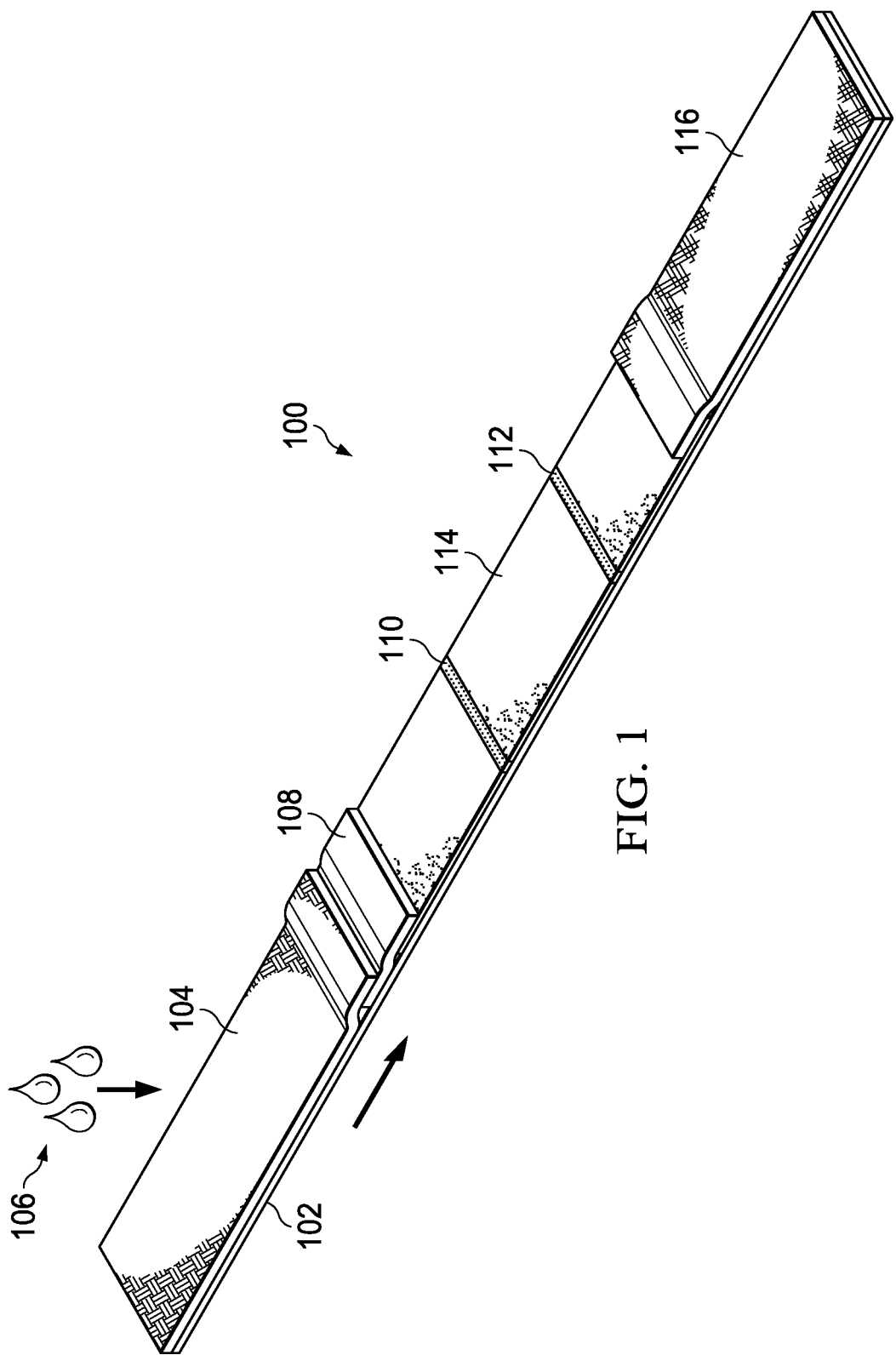
FIG. 1 illustrates a diagrammatic representation of one embodiment of a immunoassay test strip.

Referring now to the drawings, wherein like reference numbers are used herein to designate like elements throughout, the various views and embodiments of an arbovirus indicative birth defect risk test are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated one embodiment of an immunoassay test strip 100. The test strip 100 is typically housed in a testing device configured to collect a biologic analyte 106 from a user and to direct to the biologic analyte 106 onto the testing strip 100. However, it will be understood that the biologic may be applied onto a strip 100 without the strip 100 needing to be within a testing device. The test strip 100 includes a backing 102. The test strip 100 is made up of multiple sections disposed on the backing 102. A sample pad 104 is disposed on one end of the strip 100, for collecting the biologic analyte 106. The biologic analyte 106 may be any biologic needed for use in the immunoassay, such as urine, blood, saliva, stool, sweat, or other biologics to be used as an analyte. Various methods may be used to acquire the needed biologic, and such may be provided to the user packaged with the test, such as swabs, vials, containers, dilutants and other solutions, or any other equipment required. In the case of a blood analyte, a few drops of blood may be obtained from a finger stick using a finger prick device. Such a blood analyte may be blood mixed with an adequate amount of buffered solution to create the sample analyte 106 or a blood sample that is not diluted or otherwise manipulated, in which case the blood only is the analyte 106.

The biologic analyte 106, after coming into contact with the sample pad 104, begins to migrate across the strip 100 by capillary action, coming into contact with other sections of the strip 100. A particle conjugate pad 108 is disposed between the sample pad 104 and a test line 110. The conjugate pad 108 may contain various reagents associated with a particular antigen, such as a virus, allergen, or bacteria, the reagents being items such antibodies, enzymes, or other reagents needed to diagnose the particular condition. The reagent in the conjugate pad 108 may be conjugated with particles of materials such as colloid gold or colored latex beads. As the analyte 106 migrates through the conjugate pad 108, antibodies present in the sample analyte 106 complex with the reagents in the conjugate pad 108, thereby creating an immune complex that will migrate to the test zone or test line 110.

The test line 110 (T) may be precoated with the relevant antigen in question, i.e., a virus, allergen, or bacteria, for the detection of antibodies associated with the particular antigen. The immune complex created when the analyte 106 passes through the conjugate pad 108 is captured onto the antigen contained on the test line 110. This may create a qualitative response on the strip where the test line 110 is located, such as a colored response. In some embodiments, the test line 110 may not be a line, but may be other shapes or symbols, such as a plus sign. If no antigen-anti-antigen complexes are present in the analyte, no reaction occurs in the test line 110 and a qualitative response will not occur.

After passing through the test line 110, the analyte migrates further along the strip to reach a control line 112, where excess anti-antibody-colloidal gold or latex conjugates get bound. A qualitative response may be shown at the control line 112, indicating that the sample has adequately migrated across the testing membrane or substrate as intended. It will be understood that the control line 112 is not necessarily needed to perform the test, and may be eliminated entirely, but the control line 112 does provide a comparative example for a user reading the test. For example, the control line 112, in embodiments where a colored qualitative response is provided, may appear as an overly saturated color, such as a dark or bright saturated red, once the sample reaches the control line 112. This saturated color may be used as a comparison against the qualitative response shown on the test line 110. For example, if the qualitative response shown on the test line 110 is a much lighter red than that on the test line 110, it may be that very little reaction occurred at the test line. Of course, if no response is shown at all at the test line 110, no reaction has occurred. If the qualitative response at the test line 110 is of a similar saturation to the control line 112, a strong reaction is indicated.

The strip 100 may not be a continuous substrate. Rather, the various sections of the strip 100 may be separate from each other, but all adhered to the backing 102. As shown in FIG. 1, the sample pad 104 and the conjugate pad 108 are separate structures from each other. The test line 110 or zone and the control line 112 or zone are both disposed as part of a nitrocellulose membrane strip 114. The nitrocellulose membrane strip 114 is also adhered to the backing 102, but separate from the sample pad 104 and the conjugate pad 108. As shown in FIG. 1, the end of the sample pad 104 adjacent to the conjugate pad 108 may overlap the conjugate pad 108, with that end of the sample pad 106 lying over the adjacent end of the conjugate pad 108. Similarly, the end of the conjugate pad adjacent to the nitrocellulose membrane strip 114 may lie over the end of the nitrocellulose membrane adjacent to the conjugate pad. This allows for the analyte 106 to be more easily deposited onto each section of the strip 100 as it migrates across the strip 100. After the analyte 106 migrates across the nitrocellulose membrane strip 114, and thus across the test line 110 and the control line 112, the analyte 106 comes into contact with a wick 116 for absorbtion and collection of the analyte 106. The end of the wick 116 adjacent to the nitrocellulose membrane strip 114 may lie over that adjacent end of the nitrocellulose membrane strip 114, as shown in FIG. 1.

Several Flow Immune Assays have been directed toward identifying proteins, molecules of interest, and even immunoglobulins IgG, IgA, and IgM. IgE is an antibody (immunoglobulin E) that is normally present in the blood freely circulating until it moves into the tissue where it is bound to mast cells through the receptor FcERI (F-C-epsilon-R-one) otherwise known as the high affinity IgE receptor. There is a small amount of IgE bound to IgE receptors (high and low affinity receptors) on basophils, eosinophils, and other cells in the blood and tissues.

Many assay systems are geared toward the detection of infectious proteins. All of the aforementioned tests use a non-human antibody—usually IgG type—e.g., goat IgG antibody directed against a protein of interest to detect the protein of interest from the sample (blood, urine, saliva, sweat, etc.). This antibody complexes with protein of interest and forms a complex that travels across the membrane until it reaches the test zone. In the test zone there is an IgG type antibody directed against IgG from that species of animal. As further described herein, the present detecting apparatus and method use human (patient/consumer-derived) antibodies from the sample and the test zone that contains a humanized antibody directed against the protein of interest that is preconjugated to a detecting substance that results in a visual change.

Summary of Target Antigen:
The target antigens may be proteins, glycoproteins, lipoproteins or other molecular substances capable of eliciting an immune reaction and/or being bound by human specific IgE (sIgE).

Immune Assay to Detect Specific IgE:
In the detecting apparatus and method of using the same, the antigens are proteins conjugated to a noble metal, for example, gold, or latex conjugated to antigen in the test zone, for the purpose of detecting the presence of specific IgE (e.g., anti-peanut IgE in a blood sample from a finger prick). For example, an IgG class antibody (IgG1, IgG2, IgG3, or IgG4) or fragments of those classes of antibodies (fab fragments) whose origin may be any animal species (goat, rat, human, etc.) capable of detecting human IgE (anti-IgE IgG)—a suitable commercially available humanized antibody, such as omaluzimab may be used—may be used to form immune complexes of IgG-anti-IgE-sIgE that will migrate to the test zone having selected specific IgE that can bind to the conjugated antigen.

Immune assay to detect total IgE (not concerned about specific IgE):
Another embodiment includes using an IgG class antibody (IgG1, IgG2, IgG3, or IgG4) or fragments of those classes of antibodies (fab fragments) whose origin may be any animal species (goat, rat, human, etc.) capable of detecting human IgE (anti-IgE IgG)—a suitable commercially available humanized antibody that is preconjugated to a detecting molecule that results in a color change when bound to IgE as the target antigen in the test zone.

Figure 2:
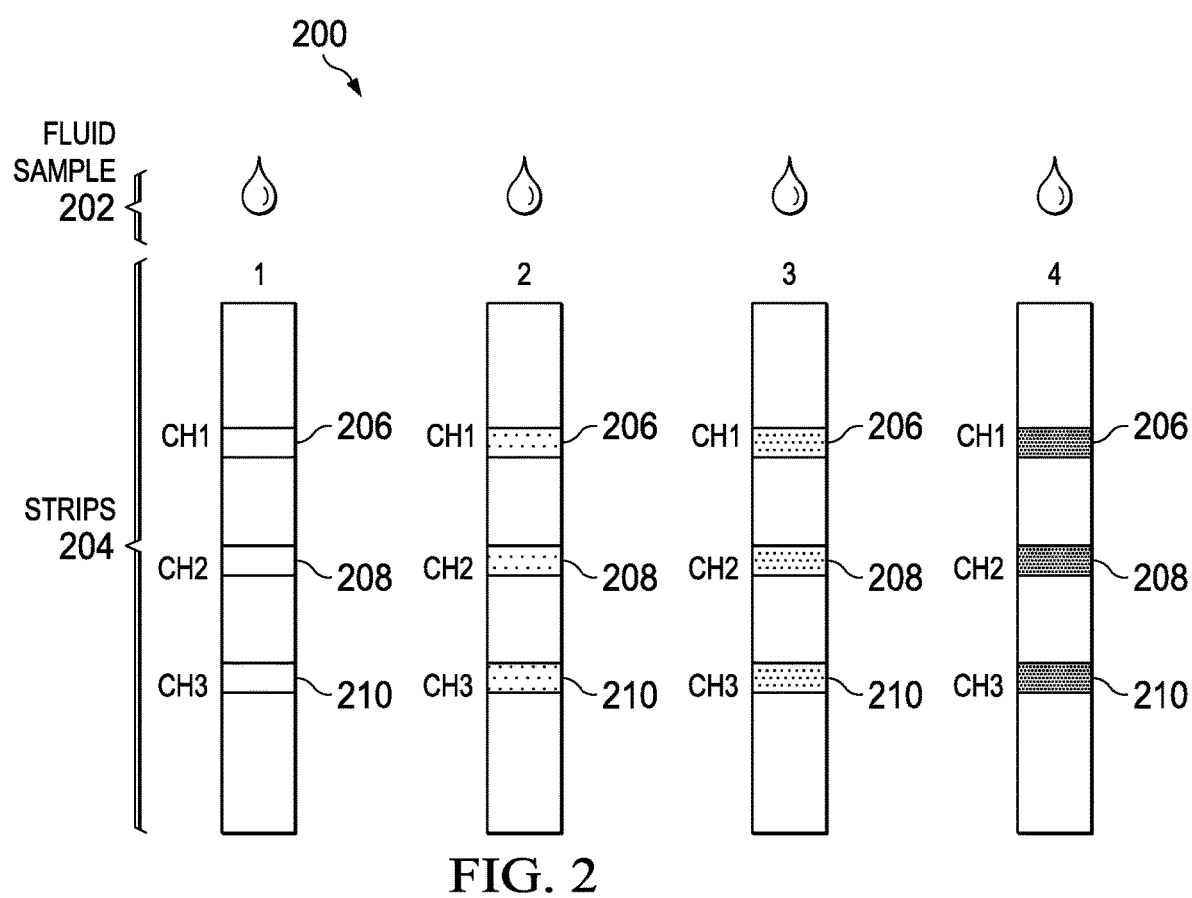
FIG. 2 illustrates a diagrammatic representation of one embodiment of an immunoassay test wherein an analyte is tested across a plurality of test strips.

Referring now to FIG. 2, there is illustrated one embodiment of an immunoassay test 200 wherein an analyte 202 is tested across a plurality of test strips 204. The plurality of test strips 204 may each be configured for testing for a particular antigen. For instance, one strip may be for testing for the presence of streptococcal bacteria (strep throat), one strip may be for testing for a peanut allergy, one strip may be for testing for the Zika virus, etc. Additionally, each strip may also test for multiple antigens. For example, as shown in FIG. 2, multiple testing panels or lines maybe be incorporated. Each line may be for a particular antigen. As shown in FIG. 2, multiple test lines 206, 208, and 208 may be disposed along the plurality of strips 204. A strip testing for allergens may have a panel for testing for peanut allergies shown at test line 206 (CH1), for cat allergies shown at test line 208 (CH2), or grass allergies shown at test line 210 (CH3).

Other examples of configurations for the testing panels can be, but are not limited to: 1) Food 5: Peanut, milk, soy, wheat, egg; 2) Nut and seed panel: almond, cashew, hazelnut, peanut, pecan, walnut, sesame seed, sunflower seed; 3) seafood: crab, lobster, shrimp, salmon, tuna; 4) Pets: cat, dog; 5) Indoor allergens: dust mites, mold mix (*alternaria, aspergillus, penicillium, cladosporium*), cat, dog; and 6) seasonal allergens: grass (Bermuda, bahia, Johnson, rye, timothy), trees (oak, elm, cedar, mesquite, pine, etc.), weeds (pigweed, ragweed, sage, Russian thistle).

With respect to other non-allergen antigens, the panels may be for testing for strep, Zika, flu, anthrax, cold viruses, cancer, HPV, Lyme disease, mononucleosis (mono), and other illnesses, and/or other conditions such as pregnancy (hCG detection) and disease risks. Some embodiments may allow for the testing of various arboviruses (arthropod-borne viruses). Arboviruses are viruses that are transmitted by arthropods, with mosquitos being a common vector for the virus. Vectors are organisms that transfer the virus from a host that carries the virus. Thus, in the case of mosquitos, a mosquito that feeds on a host that is infected with a virus may infect others when that mosquito again feeds on an uninfected host. Well-known arboviruses include Dengue virus, Japanese encephalitis virus, Rift Valley fever virus, West Nile virus, yellow fever virus, chikungunya, and Zika virus. Urine, blood, and saliva and other biologics may be used for arboviruses testing.

Certain antigens or medical conditions may be logically paired together. For instance, a testing device may include both a strip for detection of pregnancy and a strip for the detection of the zika virus, as the Zika virus has been known to cause birth defects in infants born to pregnant women that are infected with Zika. Thus, combining these two tests into a single testing device or kit would alert a woman to a potential Zika infection proximate in time to the time she also discovers she is pregnant, allowing the woman to seek medical attention immediately. This is a substantial improvement over past Zika testing, where a woman may be required to wait weeks before results are returned from a lab after having the biologic collected by her physician. In many cases, this may lead to a woman having passed a state-mandated cutoff point for abortions, such as 24 weeks in some states. Combining a Zika test with a pregnancy test and physically linking the two tests, and thus allowing for a woman to determine a Zika risk at the time of taking a pregnancy test, in which a pregnancy test may be taken as soon as six days after conception, allows for that woman to take action much sooner than the state mandated cutoff and waiting for lab results would allow.

Various testing devices that include the test strip 100 or strips may be used, such as a slide that supports the test strip 100, a cassette based diagnostic test, a dipstick, or combinations thereof. The test results in various embodiments may be in the form of a visual qualitative reading test, a visual semiquantitative format, a reader quantitative assay format, and/or combinations thereof. Additionally, an electronic implementation may be used where the result is displayed digitally on a screen disposed within the apparatus, and visible to the user.

The apparatus and method of detection may be a "one-step" approach from sample to reading without sample dilution or other sample manipulation. The sample may be diluted or endure other sample manipulation, for example the blood sample is diluted with a buffer.

Figure 3:
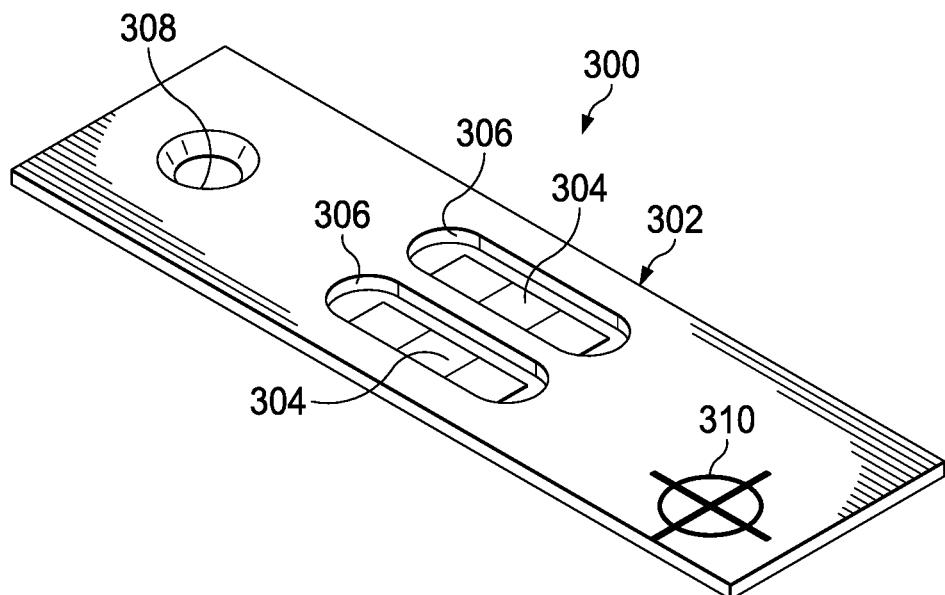
FIG. 3 illustrates a diagrammatic representation of one embodiment of a testing device.

Referring now to FIG. 3, there is illustrated a diagrammatic representation of one embodiment of a testing device 300. The testing device 300 includes a housing 302 that forms the body of the testing device. The housing 302 may be made of plastic, metal, or any material durable enough for shipping and subsequent handling by a user. The housing 302 may be hollow so that a plurality of test strips 304 may be housed within and so that a biologic may be deposited within the housing 302. The testing device 300 may further have a plurality of windows 306, each window being associated with one of the plurality of test strips 304, and allowing for a user to view at least the section of the nitrocellulose membrane strip 114 where the test line 110 and control line 112 are located. The plurality of windows 306 may be open, or covered with plastic, glass, or other materials that allow for viewing the plurality of strips 304. A sample well 308 may be disposed on a surface of the housing 302 to allow a user to deposit a biologic into the housing 302. The sample well 308 would be disposed over or near the sample pad 104 of the test strip or strips 100. In the embodiment shown in FIG. 3, a single sample well 308 is included for collection of a single type of biologic for testing, with each of the plurality of strips 304 being suited for testing for antigens using that particular biologic sample type. For example, if the testing device 300 is a combined pregnancy and Zika test, having both a pregnancy strip and a Zika strip, a urine sample may be deposited into the sample well 308, causing the urine sample to come into contact with the sample pad 104 on both the pregnancy strip and the Zika strip. It will be understood that both of these tests may also be performed with a blood sample.

The testing device 300 may also have disposed on the surface of the housing a crosshair symbol 310, used as an alignment target. This symbol may be a graphic printed or adhered to the testing device 300. The crosshair symbol 310 is used to align the testing device 300 for the taking of an image of the testing device 300 using a camera on a mobile device, for use in a mobile device application described herein. In other embodiments, the crosshair symbol 310 may be other types of symbols, such as a simple shape (circle, square, etc.), other images (such as a medical cross symbol, an arrow, etc.), or any other type of image.

Figure 4:
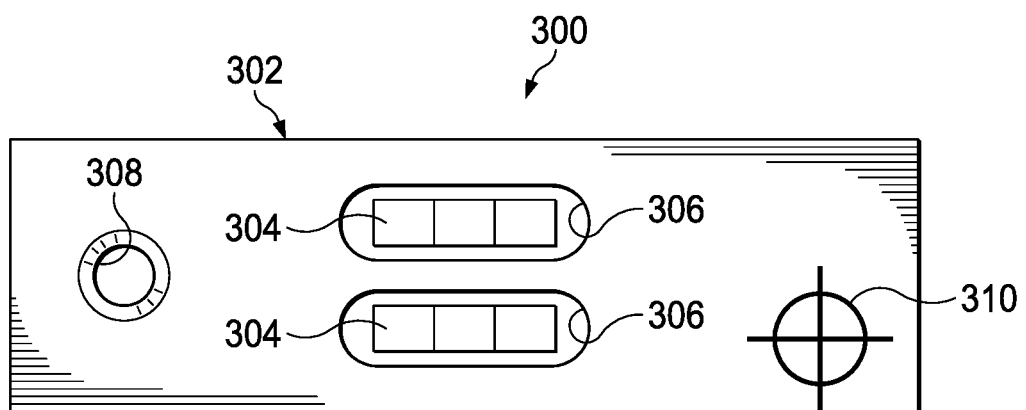
FIG. 4 illustrates a top view of the testing device of FIG. 3.

Referring now to FIG. 4, there is illustrated a top view of the testing device 300. There is again shown the housing 302, the plurality of test strips 304, the plurality of windows 306, the sample well 308, and the crosshair symbol 310.

Figure 5:
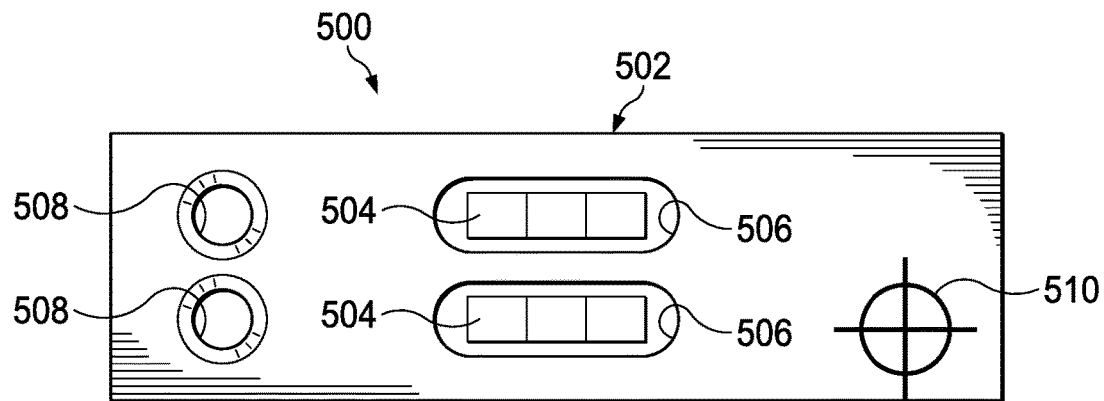
FIG. 5 illustrates a top view of one embodiment of a testing device.

Referring now to FIG. 5, there is illustrated a top view of one embodiment of a testing device 500. The testing device 500 includes a housing 502 having a plurality of test strips 504 within the housing 502 and a plurality of windows 506 for display of the plurality of strips 504. The housing 502 also includes a plurality of sample wells 508 disposed on one side of the testing device 500. Each of the plurality of sample wells 508 is associated with one of the plurality of test strips 504 and each of the plurality of sample wells 508 may be disposed over one of the sample pads 104 on the associated one of the plurality of test strips 504. This allows for a biologic to be deposited into each of the plurality of sample wells 508, with each well 508 serving to transfer the biologic to the test strip underneath the sample well. The testing device 500 further includes a crosshair 510. The crosshair symbol 510 is used to align the testing device 500 for the taking of an image of the testing device 500 using a camera on a mobile device, for use in a mobile device application described herein.

Figure 6:
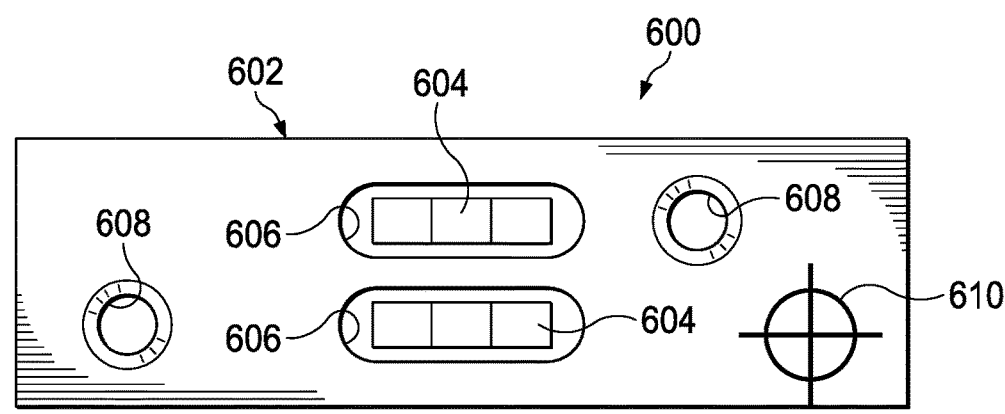
FIG. 6 illustrates a top view of another embodiment of a testing device.

Referring now to FIG. 6, there is illustrated a top view of another embodiment of a testing device 600. The testing device 600 includes a housing 602 having a plurality of test strips 604 within the housing 602 and a plurality of windows 606 for display of the plurality of strips 604. The housing 602 also includes a plurality of sample wells 608. In this embodiment, the sample wells are located on different ends of the housing 602. In the case of a two test strip device, the sample wells 608 are disposed on opposite ends of the testing device 600. The strips 604 would be arranged within the housing in such a way as to allow the sample pad 104 on each of the strip to be disposed underneath one of the sample wells 608. This is useful for testing devices that require different biological samples. For example, if the testing device 600 required a urine sample for one strip and a blood sample for the other strip, having the wells 608 disposed on opposite sides of the testing device would reduce the likelihood that a urine sample, for instance, might be inadvertently deposited into the well designated for the blood sample. In embodiments where there are more than two strips, and more than two wells, the well positions may alternate between the two sides of the testing device. For instance, a first well for a first strip might be disposed on the left side of the testing device, a second well for a second strip might be disposed on the right side of the testing device, a third well for a third strip might be disposed on the left side of the testing device, a fourth well for a fourth strip might be disposed on the right side of the testing device, and so on. The testing device 600 further includes a crosshair 610. The crosshair symbol 610 is used to align the testing device 600 for the taking of an image of the testing device 600 using a camera on a mobile device, for use in a mobile device application described herein.

The diagnostic test can, for example, be produced in a various formats for different users, such as, but not limited to, consumer/in-home use where the test is purchased through retail channels which will allow individuals to get an immediate, cost-effective test result that can lead to specific avoidance and treatment through follow-up with a medical professional.

The diagnostic test can be provided to and used by hospitals and clinics to provide rapid, on-site test results that are required to prescribe certain medications, such as omaluzimab, by their FDA labels.

This diagnostic assay can be modified to detect the presence of specific IgE in pets.

It is also noted that housing 602 is designed such that both strips 604 are disposed in physical proximity thereto and in the same actual housing. In this manner, both sets are linked physically to each other such that they cannot be separated and can be associated with a single individual and the actual test cannot be separated. As such, when a patient applies the specimens to the two sample wells 608 and the test results are exhibited, there is a high probability that two tests were performed at the same time associated with the same patient. Additionally, and electronic chip (not shown) can be embedded within the housing 602 such that the housing 602 can be registered to a specific patient and associated with the medical records of that patient.

Figure 7:
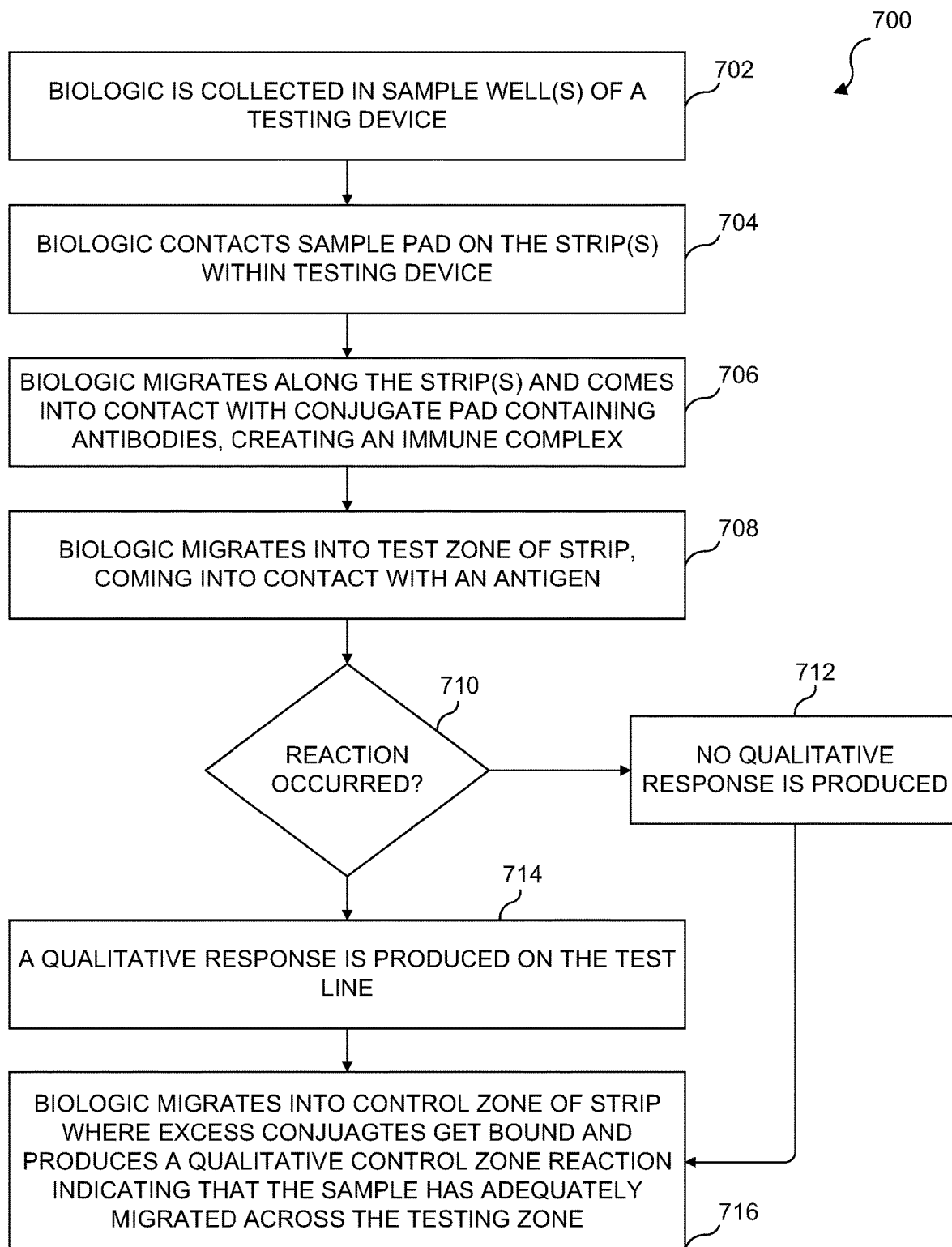
FIG. 7 illustrates a flowchart of one embodiment of a testing device use method.

Referring now to FIG. 7, there is illustrated a flowchart of one embodiment of a testing device use method 700. The method 700 begins at step 702 where a biologic is collected in a sample well or wells of a testing device. The biologic collected may be a non-diluted or non-manipulated biologic, such as blood, urine, or saliva from the user of the test. Diluted or manipulated biologics may be used instead, as required by the specific test. For example, if a viral test requires the biologic to be added to a solution, the biologic could be added to a solution that has previously been placed in a sterilized vial provided with the testing device. After the required amount of time has passed, the solution containing the biologic could be deposited into the well or wells. At step 704, the biologic contacts a sample pad disposed on a strip or strips within the testing device. At step 706, the biologic migrates along the strip or strips to come into contact with a conjugate pad containing antibodies. Antibodies present in the biologic will complex with the antibodies in the conjugate pad to create an immune complex. At step 708, the biologic migrates into a test zone of the strip or strips, coming into contact with an antigen. The antibodies in the conjugate pad serve to provide a means of detection, such as a colored response, if the immune complex binds with the antigen present in the test zone of the strip. At decision block 710, binding of the antibodies with the antigen may or may not occur depending on if antibodies associated with the antigen are present in the biologic or not. If a binding between the antibodies and the antigen does not occur the process moves to step 712 where no qualitative response is produced on the test line. If a binding does occur, at step 714 a qualitative response is produced on the test line. Whether a binding occurs or not, and whether a qualitative response is produced or not, the process moves to step 716 where the biologic migrates into a control zone of the strip or strips where excess conjugates get bound and produces a qualitative control zone reaction indicating that the sample has adequately migrated across the testing zone.

It will be understood by one skilled in the art that the antibodies and antigens applied to the testing strip may be altered depending on the type of condition being tested. For example, in the case of testing for medical conditions that do not involve an illness or infection, like pregnancy, and thus the sample biologic does not contain antibodies associated with the condition, antibodies that react to markers being tested for may be applied to the testing strip instead of an antigen. For instance, pregnancy test requires testing for the presence of hCG. Since hCG is a hormone and not an antibody produced in response to an infection, the testing strip may have antibodies that will react to the presence of hCG applied to the testing zone or line of the testing strip, as well as to the conjugate pad. Similarly, some tests might require antibodies be applied to the testing strip to detect antigens present in the sample, rather than antibodies.

Figure 8A:
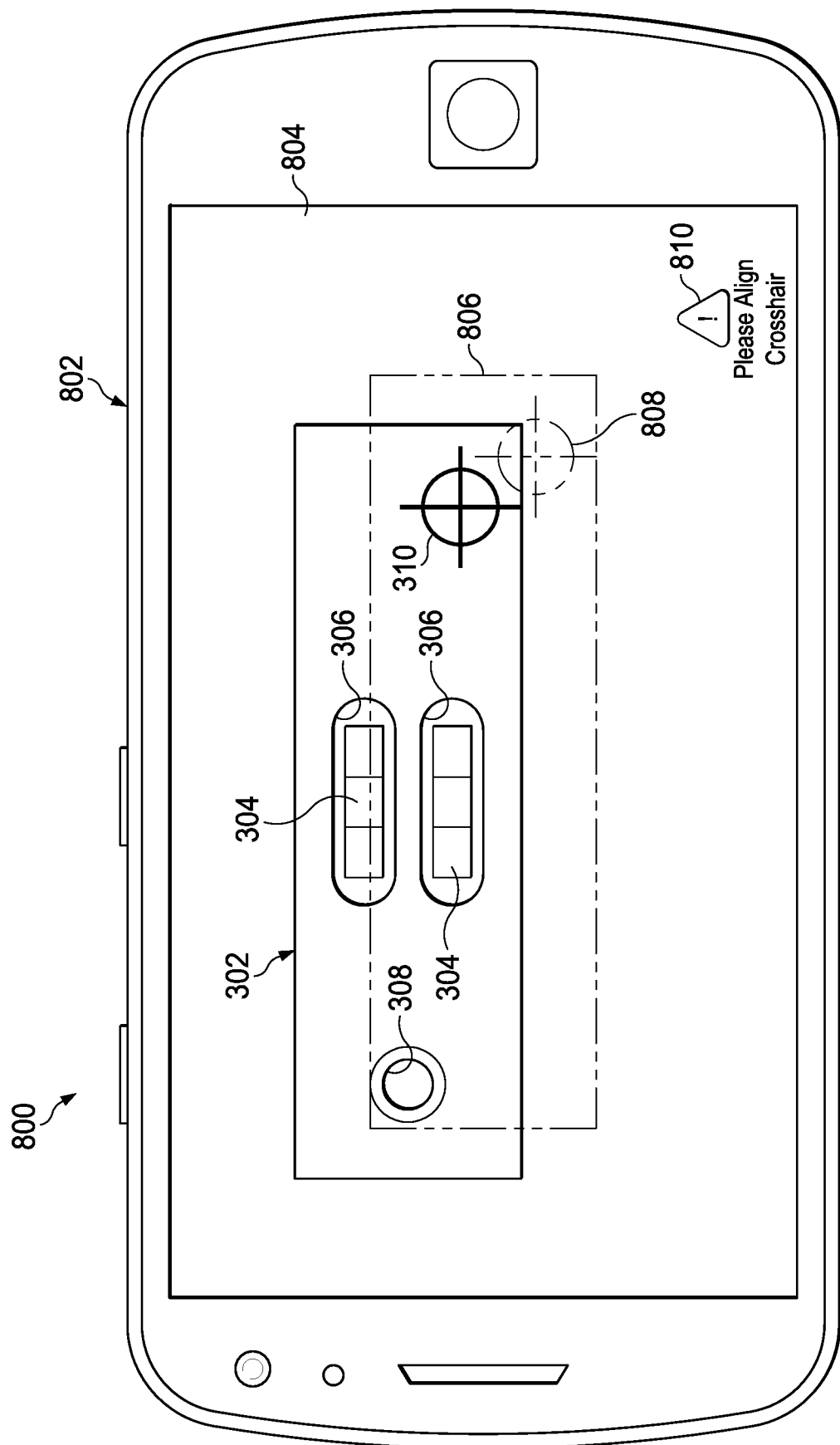
FIG. 8A illustrates a diagrammatic representation of one embodiment of a process for a mobile device application for testing device image capture and image processing, wherein an image alignment indicator is not aligned with the subject of the image.
Figure 8B:
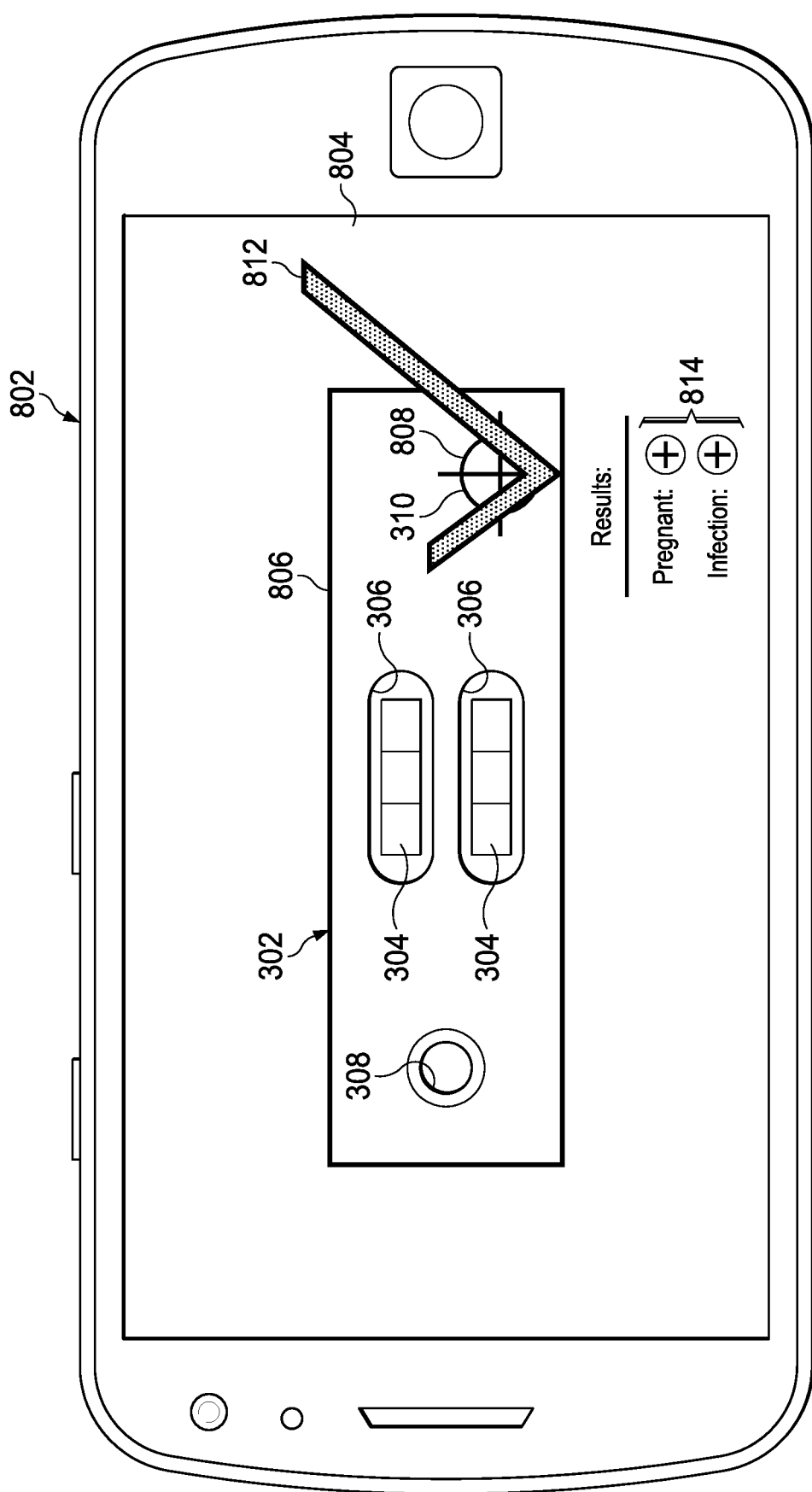
FIG. 8B illustrates a diagrammatic representation of one embodiment of a process for a mobile device application for testing device image capture and image processing, wherein an image alignment indicator is aligned with the subject of the image.

Referring now to FIGS. 8A and 8B, there is illustrated a diagrammatic view of one embodiment of a process 800 for a mobile device application for testing device image capture and image processing. The mobile device application allows for an image of a testing device, such as testing device 300, to be captured using a camera installed on a mobile device 802 having a screen 804. While the mobile device 802 displays on the screen 804 the scene captured by the camera, the mobile device application also displays a graphic on the screen 804 in the form of a boxed outline 806, the size of the outline 806 corresponding to the size of the testing device 300. Also displayed on the screen of the mobile device 802 within or near the outline is a crosshair graphic 808. A user of the mobile device 802 attempts to align the outline 806 with the borders of the testing device 300 and also attempts to align the crosshair graphic 808 with the crosshair 310 on the testing device 300. While alignment has not yet been achieved, a misalignment warning 810 may appear on the screen of the mobile device 802, indicating to the user that alignment has not yet been achieved. Such is shown in FIG. 8A.

In FIG. 8B, there is shown the result of a successful alignment of the outline 806 with the testing device 300 and successful alignment of the crosshair graphic 808 with the crosshair 310 on the testing device 300. As shown in FIG. 8B, once aligned, a success indicator 812 may appear, such as a check mark or other positive status symbol, on the aligned image. Successful alignment causes the camera on the mobile device 802 to capture the current image of the testing device 300. Other checks may occur, including ensuring that the image is focused before the image is saved. This image is then processed to determine a result based on the severity of the reaction occurring on the test strip. The mobile device application performs an analysis of the test line captured in the image, counting the number of colored pixels, as well as determining the intensity of the color. The mobile device may then compare this number and color intensity to that in the control line, providing a mathematical evaluation of the test line. Utilizing unique wavelengths of light for illumination in conjunction with either CMOS or CCD detection technology, a signal rich image is produced of the test lines to detect the colloid gold or latex particles. This provides an advantage because a user simply looking at the two lines may not know what the test line indicates, such as when the colored line does appears on the strip, but it is a faded line, rather than a dark line. Based on this analysis, the mobile device application may provide a results indicator 814.

The results indicator 814 may be a qualitative result or a quantitative result. For example, and as shown in FIG. 8B, a qualitative result for the results indicator 814 may indicate, in the case of a testing device for testing pregnancy as well as an infection, a plus sign next to a line reading "pregnant:" and a plus sign next to a line reading "infection:" to indicate that the user is both pregnant and infected with the bacteria or virus being tested, such as the Zika virus. For a quantitative result, the results might provide a numeric rating. For instance, a rating system between 1-100 may be used. If the results provide a low rating to the user, such as a rating of 10, this indicates a low risk of infection, although medical attention may be sought by the user anyway. For example, if the user is pregnant, and also receives a 10 rating for Zika, this may indicate that Zika was detected in low amounts. However, the user may still seek medical attention or further testing from her doctor because Zika has been known to cause birth defects. If the rating is a high rating, such as 95, this indicates that an infection has most likely occurred and medical attention should be sought immediately.

This same quantitative rating system may be applied to any test (viral infections, bacterial infections, pregnancy, and other health conditions), as the quantitative test can be performed using the software described herein to accurately test bound antibody concentrations on the test strip. In some embodiments, a combined qualitative and quantitative result may be presented, such as both a rating and a plus or minus sign being presented, or other types of quantitative and qualitative indications. Additionally, various combinations of tests may be provided for in the testing device, such as pregnancy/Zika, preganancy/flu, pregnancy/strep/Zika, etc.

Figure 9:
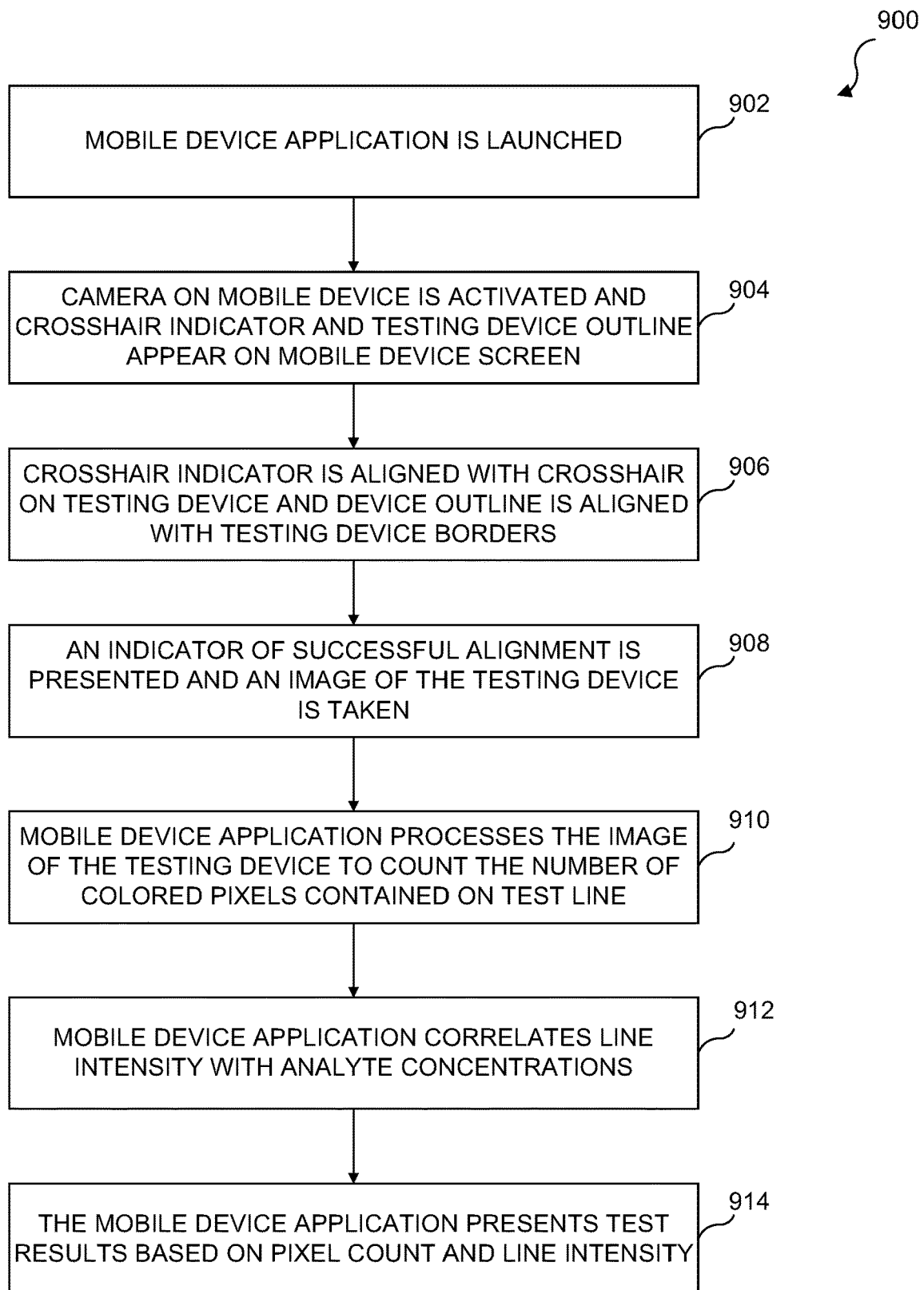
FIG. 9 illustrates a flowchart of one embodiment of an image analysis process using a mobile device.

Referring now to FIG. 9, there is illustrated a flowchart of one embodiment of an image analysis process 900 using a mobile device. At step 902 a mobile device application is launched. At step 904 a camera on the mobile device is activated and a crosshair indicator and a testing device outline appear on the mobile device screen. At step 906 the crosshair indicator presented on the screen of the mobile device is aligned with a crosshair icon on the testing device and the device outline presented on the screen of the mobile device is aligned with the borders of a testing device. At step 908, an indicator of successful alignment is presented on the screen and an image of the testing device is taken by the mobile device camera. At step 910, the mobile device application processes the image of the testing device to determine test line strength by counting the number of colored pixels contained in the test line. At step 912, the mobile device application correlates line intensity with analyte concentrations to further determine test line strength. At step 914, the mobile device application presents the test results based on pixel count and line intensity, providing either a qualitative or quantitative result.

In some embodiments, the number of pixels indicating bound antibodies on the strip may be measured against that in the control line to compare line intensity between the two lines, with the control line acting as an example of a strong reaction, indicating a strong infection, and determining how close the test line intensity is to the control line. This would lead to a logical quantitative result. For instance, if the test line is determined to have a pixel count and line intensity that is 25% of the pixel count and line intensity of the control line, a rating of 25 may be given. If a qualitative result is to be provided, a rating of 25 may give a qualitative result that is negative, or it could be positive depending on the type of condition being tested and known actual infection results where a rating of 25 occurred for that condition.

In some embodiments, the test line may not be compared with the control line to determine a result. Rather, the mobile device application may have access to a database having data on numerous past tests for the same condition. This data may instead be used as the control. This allows the application on the mobile device to retrieve data on past tests and compare the test line data of the current test to past tests. Overall data for past tests may be provided and compared against, such as providing an average or a curve of past tests, or individual tests rated as having accurate results may be compared against.

In addition to a status result of an infection or other medical condition being provided to the user, other indicators of health may also be tested and results thereon provided. This provides for potential early identification of pregnancy and risk of morbidity, allowing for medical attention to be sought much more quickly. Indicators of health may be detected from biologics, such as urine and blood. Urine, for example, allows for the detection of glucose levels, proteins, bacteria, and infectious markers. In the case of glucose, glucose is usually not found in urine, but, if it is, that is an indicator of extremely high levels of glucose in the body, where the kidneys release excess glucose into urine. This is often a sign of diabetes. Protein in the urine may indicate a malfunctioning of the kidneys, which could be the result of high blood pressure. Similarly, if blood is detected in urine, it could be a sign of a problem with the kidneys or the bladder. Blood, for example, allows for the detection of glucose, inflammation, hormones, genetic defect risks, and metabolic endocrine disorders.

Figure 10:
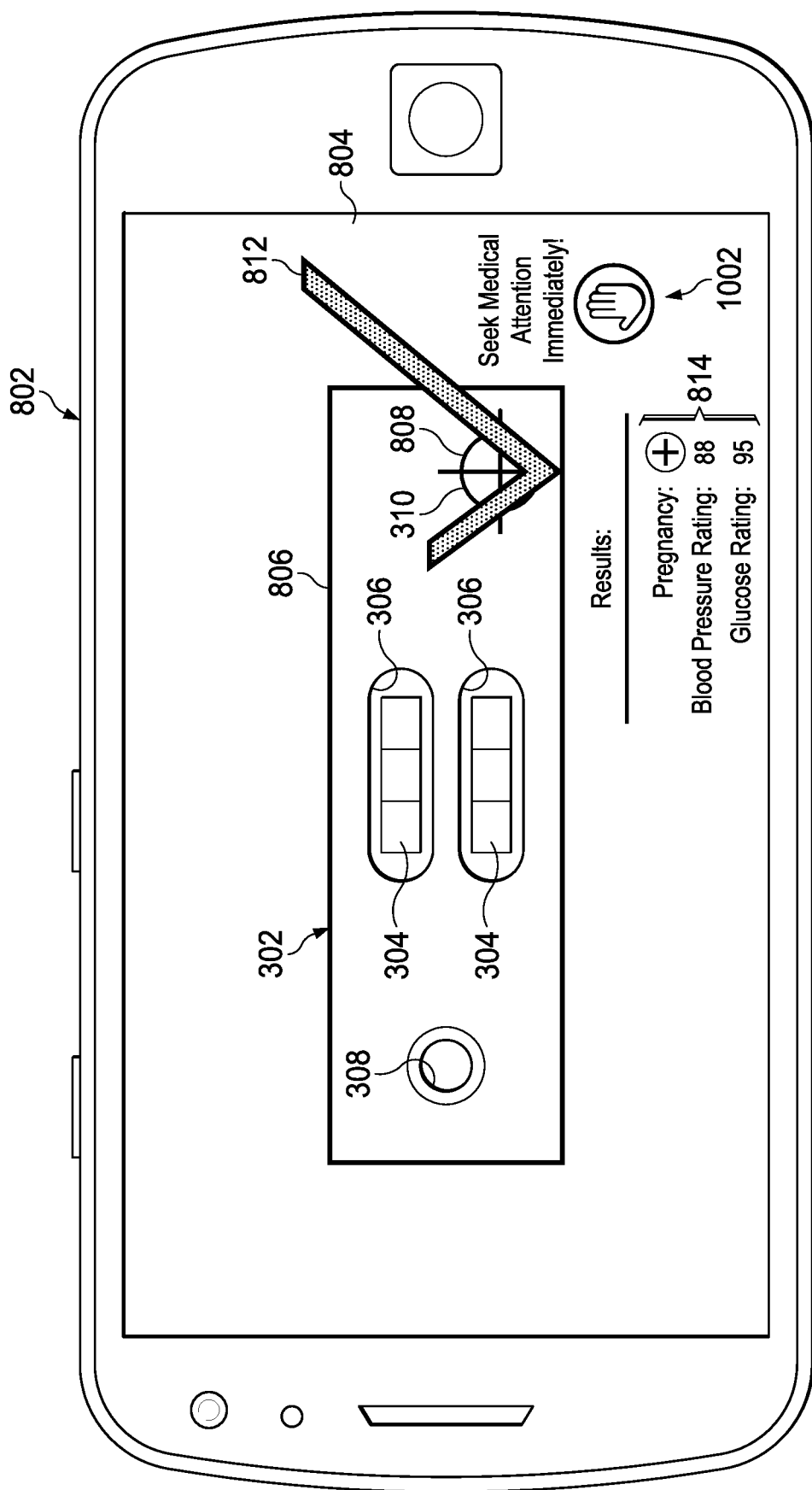
FIG. 10 illustrates a diagrammatic representation of another embodiment of a process for a mobile device application for testing device image capture and image processing, wherein an image alignment indicator is aligned with the subject of the image.

Referring now to FIG. 10, there is illustrated another embodiment of a successful alignment of the outline 806 with the testing device 300 and successful alignment of the crosshair graphic 808 with the crosshair 310 on the testing device 300, wherein quantitative results for health risk indicators are provided. In this embodiment, the results indicator 814 provides a qualitative result for pregnancy, and quantitative results for other health risk indicators. In the embodiment shown in FIG. 10, the health risk indicators being tested are markers for blood pressure and for glucose levels. For blood pressure, this is a test for markers in the blood that can be associated with high blood pressure. These could be test for such things as low levels of vitamin D and the such. Studies have shown that patients suffering from essential hypertension will be under oxidative stress and Malondialdehyde (MDA) is the principal and most studied product of polyunsaturated fatty acid pre-oxidation. This can show an indirect correlation with anti-oxidants, particularly with superoxide dismutases (SODs) (r=0.573) and catalase (r=0.633) representative anti-oxidant are involved in reducing the stress of a patient's biological system during hypertension. Another marker for hypertension is buildup of uric acid, where in uric acid is a marker for xanthine oxidase-associated oxidants and that the latter could be driving the hypertensive response. Additional markers are cortisol, a hormone. The test strips 604 can test for the different biological markers.

The results indicator 814 provides numeric ratings, in this case, 1-100, with the blood pressure rating being 88 and the glucose rating being 95. This indicates that both blood pressure and glucose are extremely high. Due to this, an additional alert indicator 1002 is presented to the user on the screen of the mobile device, alerting the user to seek medical attention immediately. This is to ensure that the health of both the pregnant woman and the fetus can be checked as close to the time of pregnancy detection as possible and medical attention received if needed.

Figure 11:
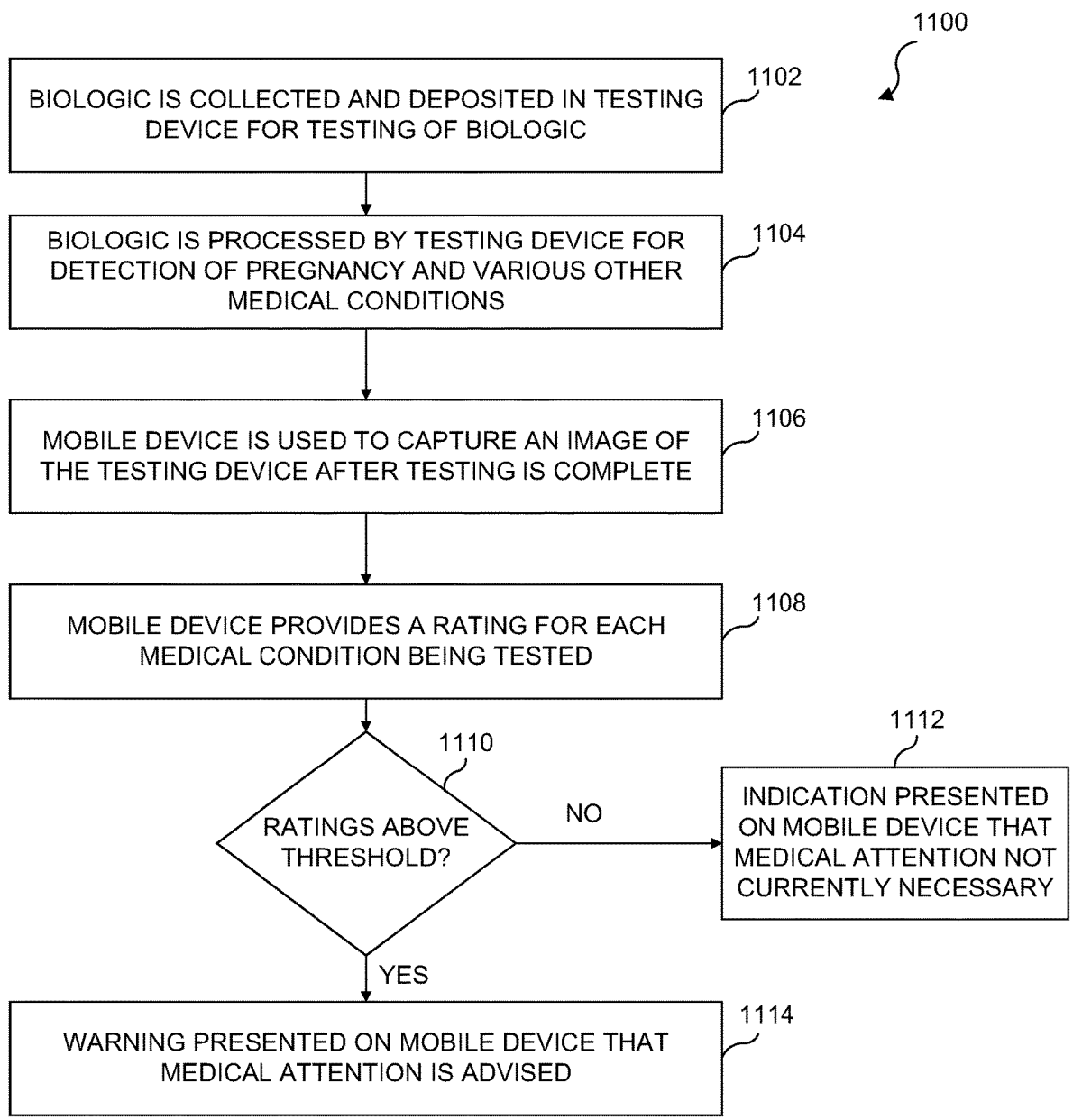
FIG. 11 illustrates one embodiment of a consumer driven biologic and disease data collection system.

Referring now to FIG. 11, there is provided a flowchart of one embodiment of a pregnancy disease risk assessment process 1100. The process 1100 begins at step 1102 where a biologic is collected and deposited in a testing device for testing of the biologic. At step 1104, the biologic is processed by the testing device for detection of pregnancy and various other medical conditions. These medical conditions may be high blood pressure, diabetes, bacterial or viral infections, inflammation, an increase in hormone levels, genetic disease markers, and/or metabolic disorders. At step 1106, a mobile device is used to capture an image of the testing device after testing is complete. In some embodiments, test results may be immediate. In other embodiments, and depending on the medical conditions being tested, the test may take a certain amount of time to complete. In this case, the user of the test would be alerted to this fact in instructions provided with the testing device. Additionally, a visual indicator on the testing device may alert the user that a test is now complete. At step 1108, the mobile device provides a rating for each medical condition being tested, such as that described with respect to FIG. 10 herein.

At decision block 1110, it is determined whether the ratings for each condition exceed a certain threshold for that condition. If not, the process 1100 moves to step 1112, where an indication is presented to the user via the mobile device screen that medical attention is not currently advised or necessary. If at decision block 1110 it is determined that at least one of the medical conditions being tested rises above a certain threshold, the process 1100 moves to step 1114 where a warning is presented to the user via the mobile device screen that medical attention is advised. The thresholds for medical conditions may not trigger a warning even if a rating exceeds a threshold, if, in the event of multiple tests being performed, the combined test results do not warrant immediate medical attention. For example, if a user is testing for a cold virus, blood pressure, and glucose, and only the cold virus rating is above the threshold, there may not be a warning provided to the user. Additionally, ratings may be weighted or aggregated based on the medical conditions being tested. For example, if blood pressure, inflammation, and glucose are being tested for, and they all are given only moderate ratings that do not rise above the threshold for any condition individually, an warning to seek medical attention may still be provided due to the combination of conditions taken together.

Figure 12:
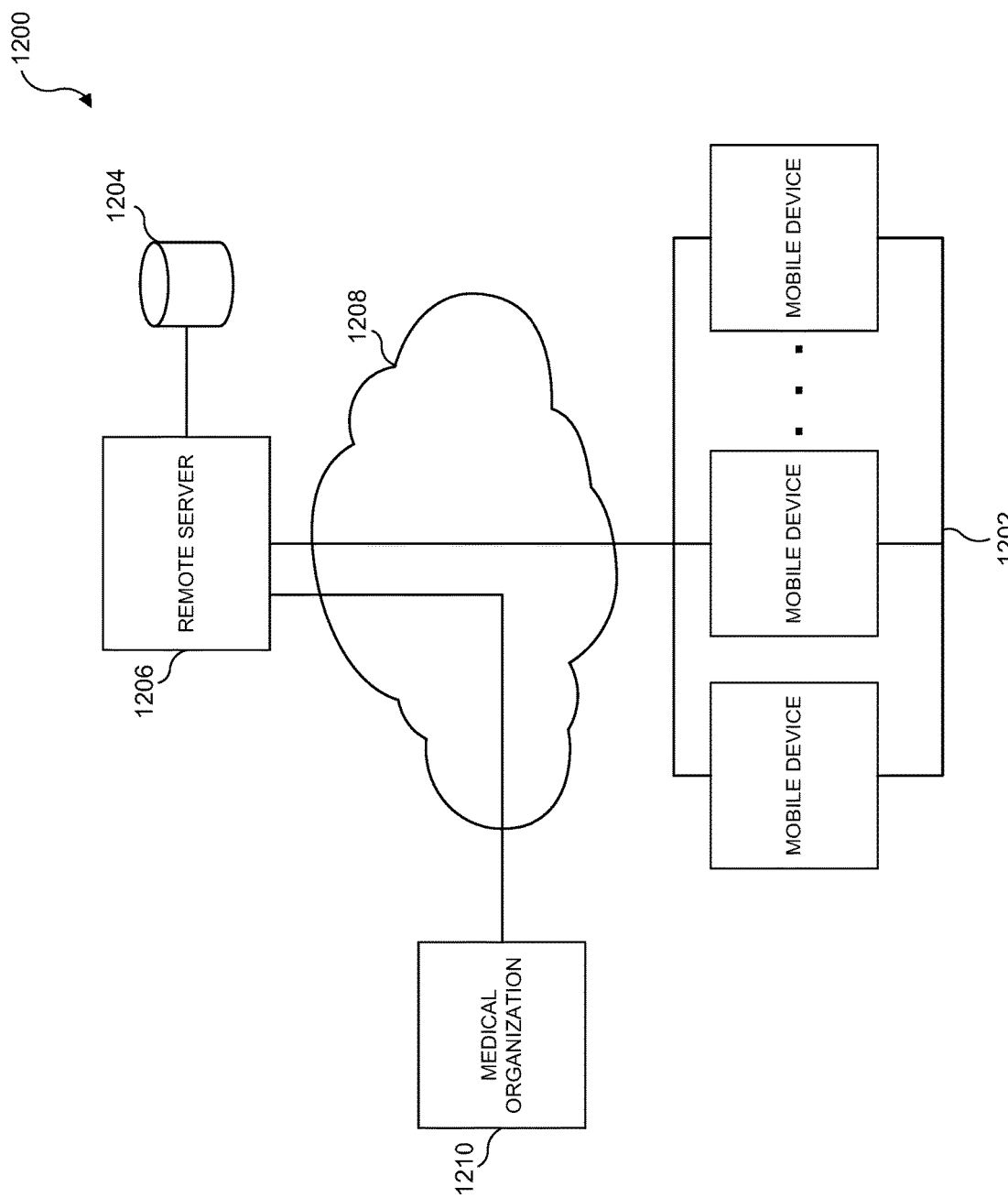
FIG. 12 illustrates one embodiment of a consumer driven biologic and disease data collection system.

Referring now to FIG. 12, there is illustrated one embodiment of a consumer driven biologic and disease data collection system 1200. Data collected from users performing the tests disclosed herein effectively can provide a wealth of information. As tests are performed data may be passed by a plurality of mobile devices 1202 being used by users performing tests to a database 1204, the database being at a remote server 1206, over a network 1208. The user is sourcing a biologic from user's own body. This is done at home, not in a lab, hospital, or clinic. Each particular test would expect a certain type of biologic to be provided. For instance, for a pregnancy test, a urine sample is provided and tested for pregnancy markers. For a stool test, the stool might be dissolved in a vial with a solution provided with the testing device/kit, and tested for various disease or infectious markers. Data and results from the tests may be stored on the database 1204 at the remote server 1206. As described herein, this data may be used as a control for testing analysis for users of the plurality of mobile devices 1202. This data may also be used to provide data sets for biologics to a medical organization 1210. The medical organization 1210 may be doctor's offices, researchers, hospitals, testing labs, and other individuals or organizations that have an interest in the health and analysis of users taking the test and of their biologic samples. In this way, data can be gathered from a variety of biologics tested for a variety of different medical conditions and characteristics.

Figure 13:
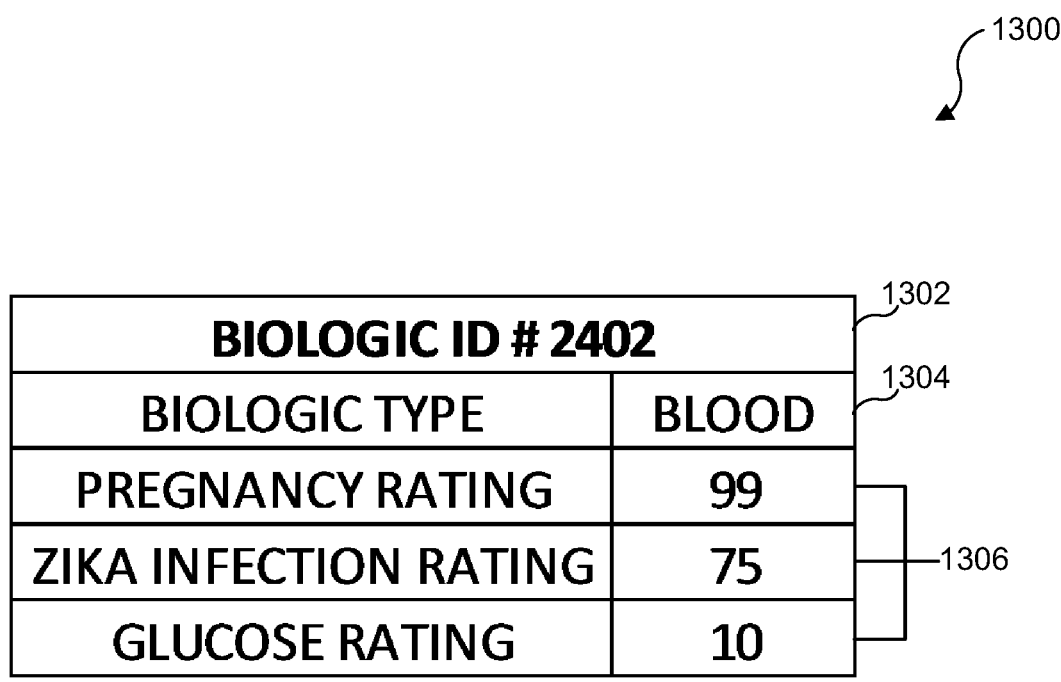
FIG. 13 illustrates an example of a unique biologic ID database table.

Referring now to FIG. 13, there is illustrated an example of a unique biologic ID database table 1300. The table 1300 is illustrative of the type of data stored in association with data for a biologic transmitted by the plurality of mobile devices 1202 for storage on the database 1204. A biologic ID header 1302 is provided that shows that the biologic sample has been given a unique ID. All data concerning the biologic may be stored in association with the unique biologic ID. The table 1300 also includes a biologic type entry 1304. This designates what type of biologic that the biologic associated with the unique ID is, such as blood, urine, stool, saliva, sweat, or other biologics. The table 1300 also provides a plurality of test ratings 1306, for various tests performed on the biologic. In the example shown in FIG. 13, a blood biologic is provided having an assigned ID of 2402, and having been testing for pregnancy markers, the Zika virus, and for glucose levels. The rating for pregnancy was a 99 rating, the rating for a Zika infection was a 75, and the rating for glucose levels was a 10. This would indicate that the test subject has an extremely high likelihood of both a pregnancy and a Zika infection, which would have resulted in a warning to seek medical attention at the conclusion of the tests. Other information may also be stored in the database in relation to the biologic, including other condition ratings, time and date each test was performed, user information such as ethnicity, gender, and age, and status indicators such as whether a test subject visited a physician as a result of the tests. The database 1204 thus provides the test subject with a growing collection of information that may be accessed by the test subject. This allows the test subject to present the test results to her physician for medical attention or additional testing, and allows for others who may access the database, such as disease researchers, to have access to data on various biologic samples and their markers.

Figure 14:
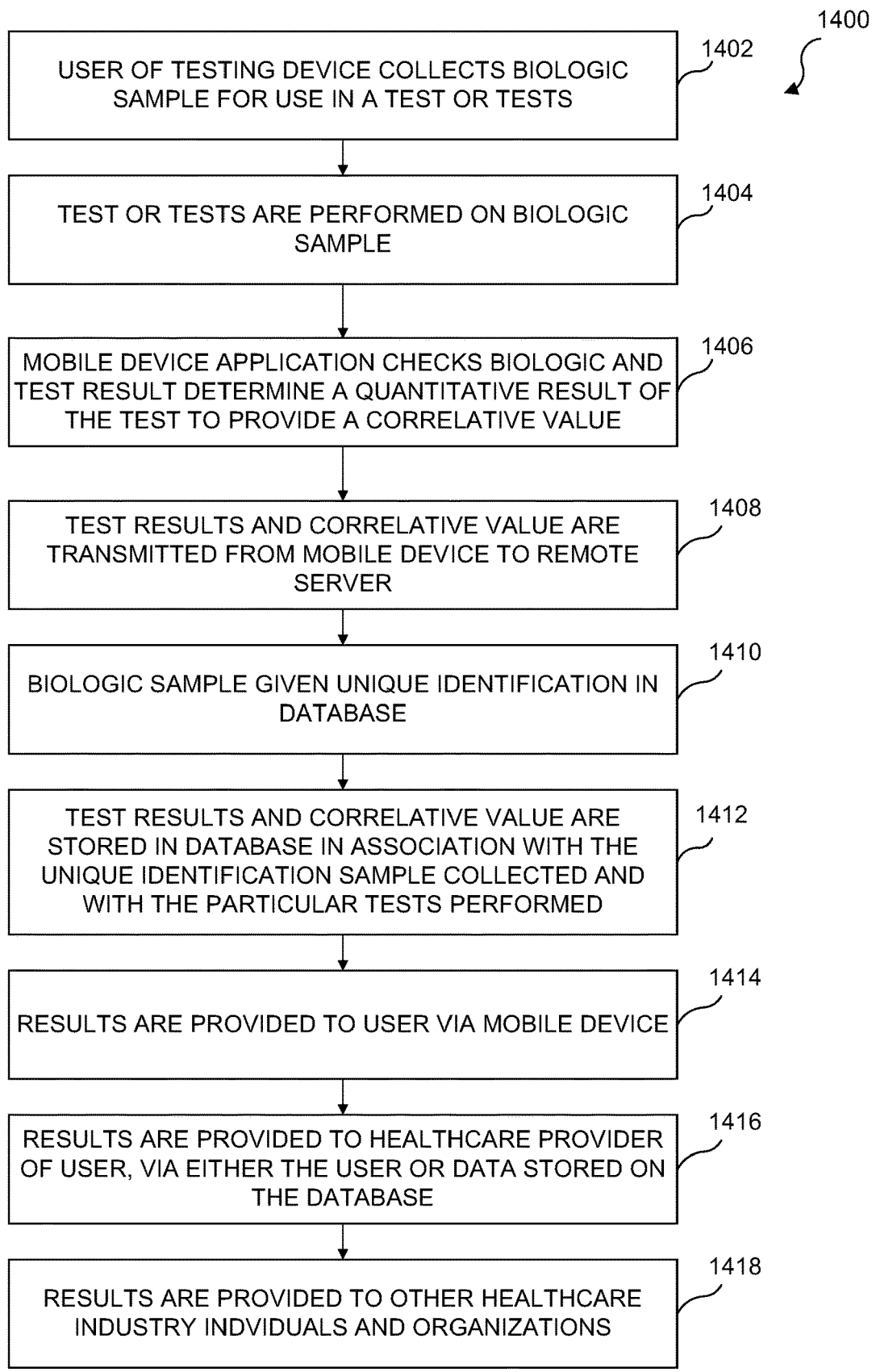
FIG. 14 illustrates a flowchart of one embodiment of a biologic data collection and dissemination process.

Referring now to FIG. 14, there is illustrated a flowchart of one embodiment of a biologic data collection and dissemination process 1400. The process 1400 begins at step 1402 where a user of a testing device collects a biologic sample for use in a test or a series of tests. At step 1404, the test or series of tests are performed on the biologic sample. At step 1406, a mobile device application checks the biologic sample the testing device result to determine a quantitative result of the test to provide a correlative value for the condition being tested in the biologic sample. At step 1408, the test results and correlative values, or multiple values if multiple tests on the biologic sample were conducted, are transmitted to the remote server 1206. At step 1410, the biologic sample is given a unique identification number in the database 1204. At step 1412, the test results and correlative value or values are stored in the database 1204 in association with the unique identification number given to the biologic sample collected and in association with the particular tests performed. This way, the particular biologic sample may have various characteristics stored and retrieved in association with the biologic sample, and the test results may also be retrieved when data on a particular test is needed on a cross-section of users.

At step 1414, the results are provided to the user on the user's mobile device. At step 1416, the results are provided to the user's healthcare provider. The healthcare provider may receive the test results due to a visit from the user, the user bringing the results of the test with her on her mobile device, or the healthcare provider may receive the results from the database 1204 if the healthcare provider has permission to access the database 1204, or if access is granted in anticipation of the user's appointment with the healthcare provider. At step 1418, the test results are also provided to other healthcare industry individuals and organizations, including medical researchers, hospitals, and others.

Figure 15:
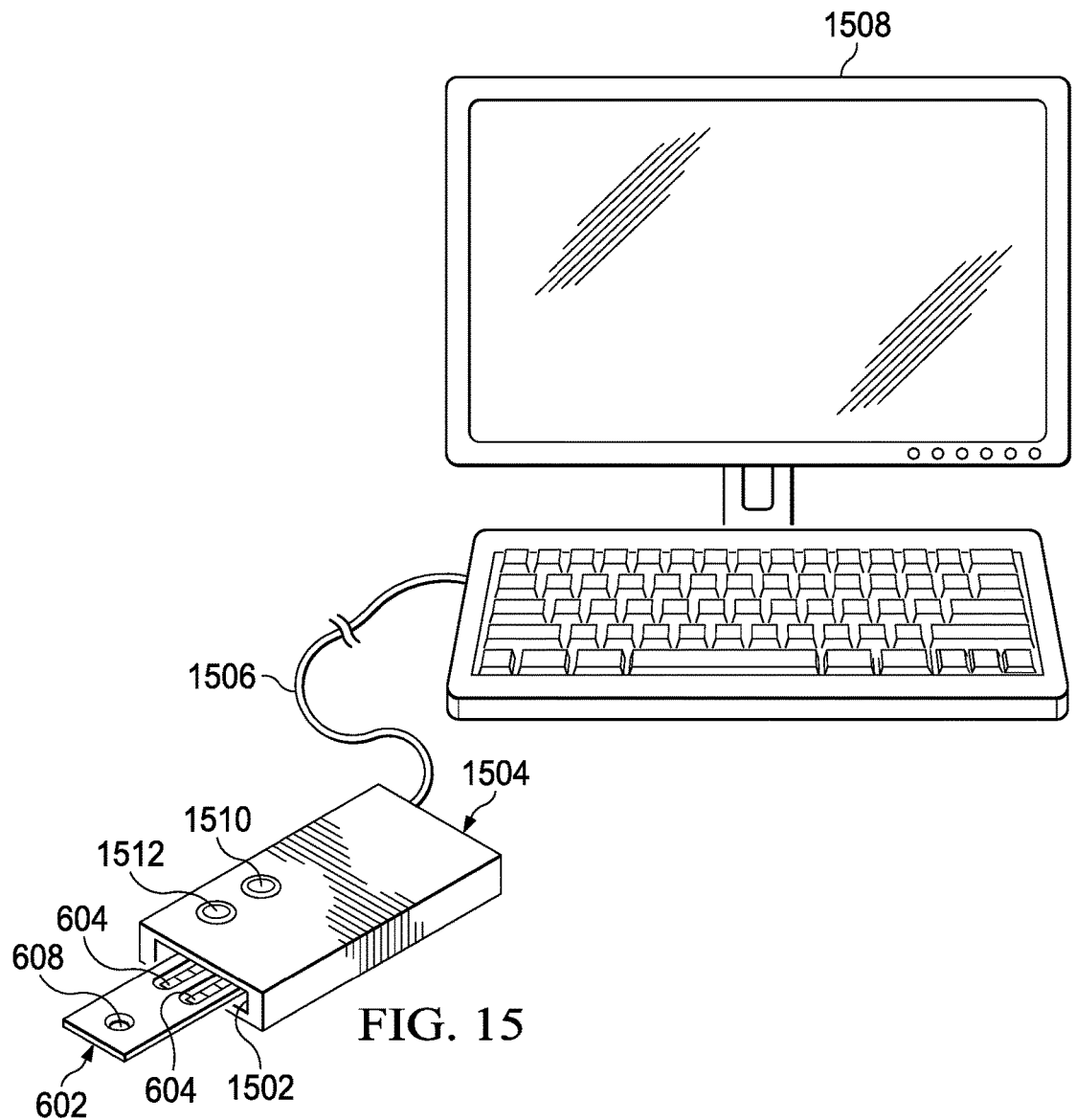
FIG. 15 illustrates a perspective view of a system for scanning test strips.

Referring now to FIG. 15, there is illustrated a perspective view of a system for scanning test strips. The housing 602, as described hereinabove with respect to FIG. 6, is illustrated as being disposed within a slot 1502 in a test housing 1504. The test housing 1504 is connected through a line 1506 to a PC 1508. When the housing 602 containing the test strips 604 after being subjected to the biologics is inserted within the slot 1502, the test housing 1504 will scan the test strips 604 and analyze the results with the PC 1508. The PC 1508 will run some type of algorithm that can analyze the results of both of the test strips 604. There can be provided to indicators 1510 and 1512 on the surface of the test housing 1504, one being, for example, a ready LED and one being a green LED. The PC 1508, after analyzing results, can then provide a warning indicator such as lighting up the green LED for a positive indication of pregnancy and the red LED for indicating that there is some issue. As an example, suppose that the second test strip tested for the Zika virus. If so, a warning would be appropriate to output and activate the red LED. There could be any other type of indicator associated with the second test at 604 that, in a combination with the test results of the first test strip, i.e. for testing for the presence of a pregnancy state, testing for such things as diabetes, etc. Further, although only two test strips 604 are illustrated, there could be multiple test strips testing for many different biological issues that may be present in an individual. In this embodiment, by inserting the housing 602 into the test housing 1504 and allowing the PC 1508 to analyze the results, the indicators associated with the test strips can be analyzed with the assumption that all of the test return results were associated with an individual and in proximate time to each other. That means that the individual patient applied biological specimens, such as urine, blood, etc., to the appropriate test strips and, since these were all contained within the same test strip housing 602, this provides an indication that they are associated with a single patient. Further, the test performed will typically be a test that will provide a very short-term response. Thus, the specimens can be applied to the test strips 604 in the test strip housing 602 and then inserted within the slot 1502 for testing by the PC 1508.

Figure 16:
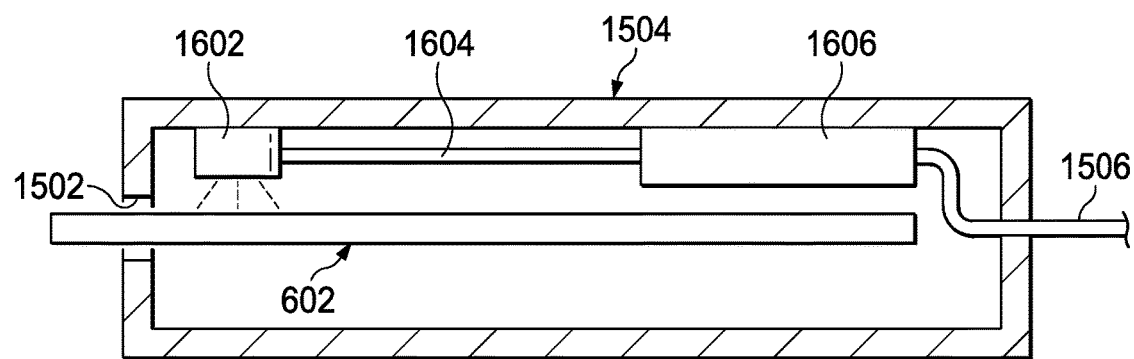
FIG. 16 illustrates a cross-sectional view of the system of FIG. 15.

Referring now to FIG. 16, there is illustrated a cross-section of the test housing 1504. It can be seen that the test strip housing 1504 is passed in slot 1502 past the camera 1602. The camera 1602 is operable to scan a small cross-section of the test strips 604 on the surface thereof as the test strip housing 602 passes thereby. Of course, there could also be a much larger camera provided for taking an entire image of the test strips 604 after being inserted within the test housing 1504. The camera 1602 is connected via a wire 1604 two in electronics package 1606 to process the information and send it to the PC 1508. The electronics package 1606 will also drive the indicators 1510 and 1512.

Figure 17:
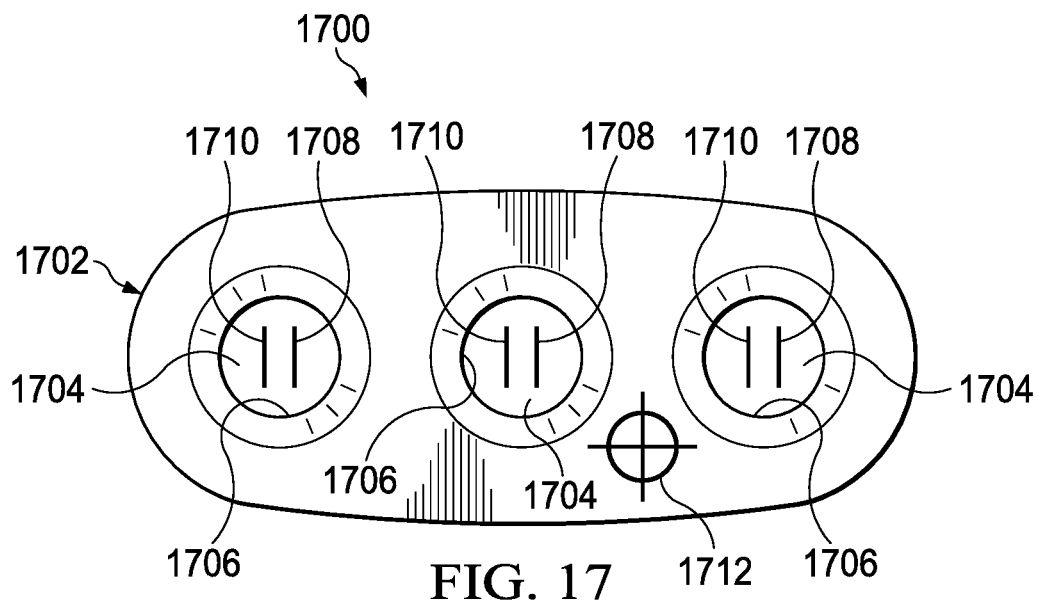
FIG. 17 illustrates one embodiment of a vertical flow immunoassay device.

Referring now to FIG. 17, there is illustrated one embodiment of a vertical flow immunoassay device 1700. It will be understood that testing device 300 and other embodiments herein illustrate a lateral flow immunoassay device. However, other types of immunoassay devices may be used. For example, vertical flow immunoassay devices may be used, a two-sided flow through assay, or even a sandwich ELISA test may be run.

The testing device 1700 includes a housing 1702 that forms the body of the testing device. The housing 1702 may be made of plastic, metal, or any material durable enough for shipping and subsequent handling by a user. The housing 1702 may be hollow so that a plurality of immunoassay test pads 1704 may be housed within and so that a biologic may be deposited within the housing 1702. The testing device 1700 may further have a plurality of sample wells 1706, each sample well having one of the plurality of immunoassay test pads 1704 disposed within, and allowing for a user to view at least a section of a nitrocellulose membrane of each of the immunoassay test pads 1704, the membrane having a test line 1708 and control line 1710. The testing device 1700 may also have disposed on the surface of the housing a crosshair symbol 1712, used as an alignment target. This symbol may be a graphic printed or adhered to the testing device 1700. The crosshair symbol 1712 is used to align the testing device 1700 for the taking of an image of the testing device 1700 using a camera on a mobile device, for use in a mobile device application described herein. In other embodiments, the crosshair symbol 1712 may be other types of symbols, such as a simple shape (circle, square, etc.), other images (such as a medical cross symbol, an arrow, etc.), or any other type of image. In other embodiments, the device 1700 may be configured in such a way as to allow a biologic sample to be deposited into a sample well, and to present the results of the test on the opposite side of the housing. Such a configuration would allow the biologic to flow through the testing pad within the housing, with the reaction occurring on a reactive membrane on the side of the device opposite the sample well, with the device having a window for viewing the results.

Figure 18:
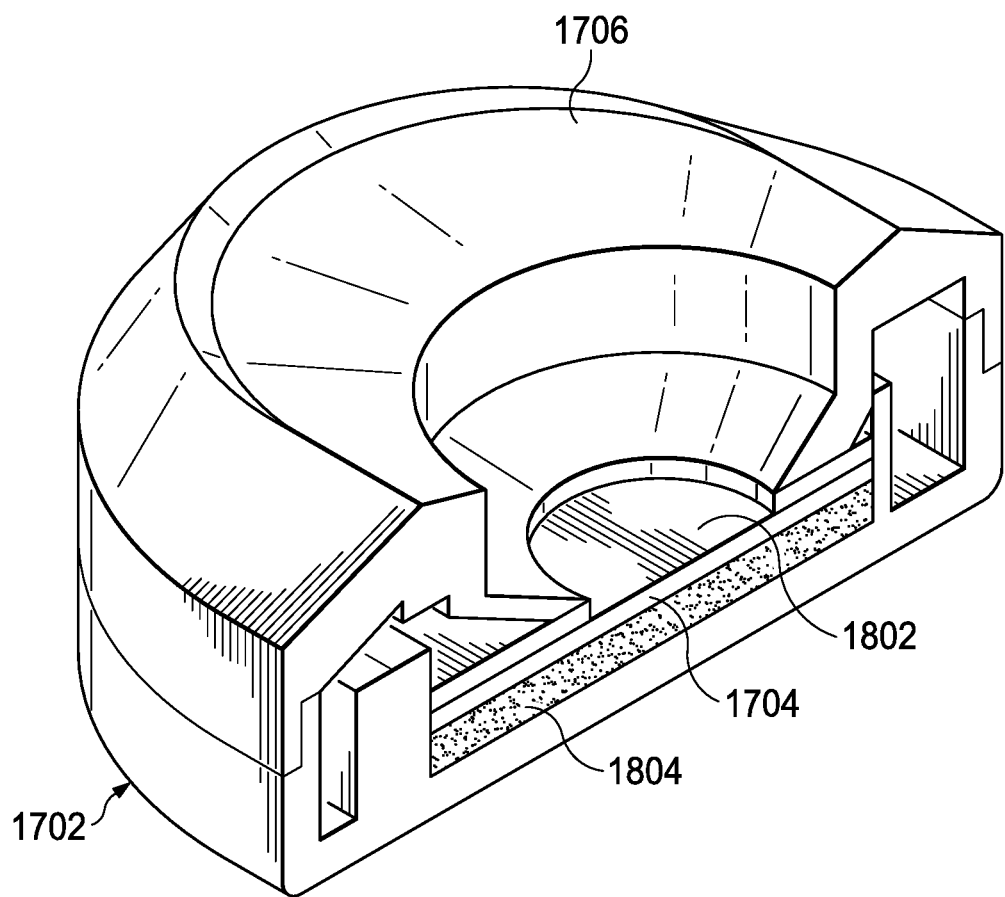
FIG. 18 illustrates a cross-sectional view of one embodiment of the vertical immunoassay device of FIG. 17.

Referring now to FIG. 18, there is illustrated a cross-sectional view of one embodiment of the vertical immunoassay device 1700. There is shown one of the plurality of immunoassay test pads 1704 residing within the housing 1702 below one of the plurality of sample wells 1706. The one of the plurality of immunoassay test pads 1704 includes a immunoreactive membrane 1802, such as the nitrocellulose membranes disclosed herein. The immunoreactive membrane 1802 may have particle conjugates disposed thereon that binds when a biologic sample is received onto the immunoreactive membrane 1802 via the sample well 1706, if the biologic sample contains the antigens or antibodies, or other indicators, for which the test is configured. The one of the plurality of immunoassay test pads 1704 also includes an absorbent pad 1804 for collection of excess biologic sample. It will be understood that the cross-sectional view illustrated in FIG. 18 shows one well of the plurality of sample wells 1706. The other wells included in the device 1700 would be configured in a similar manner as that shown in FIG. 18. There may also be included in the device 1700 an inner separating wall between each of the plurality of immunoassay test pads 1704, to ensure that excess biologic material that is not adequately absorbed by the absorbent pad 1804 does not contaminate neighboring immunoassay test pads.

Figure 19:
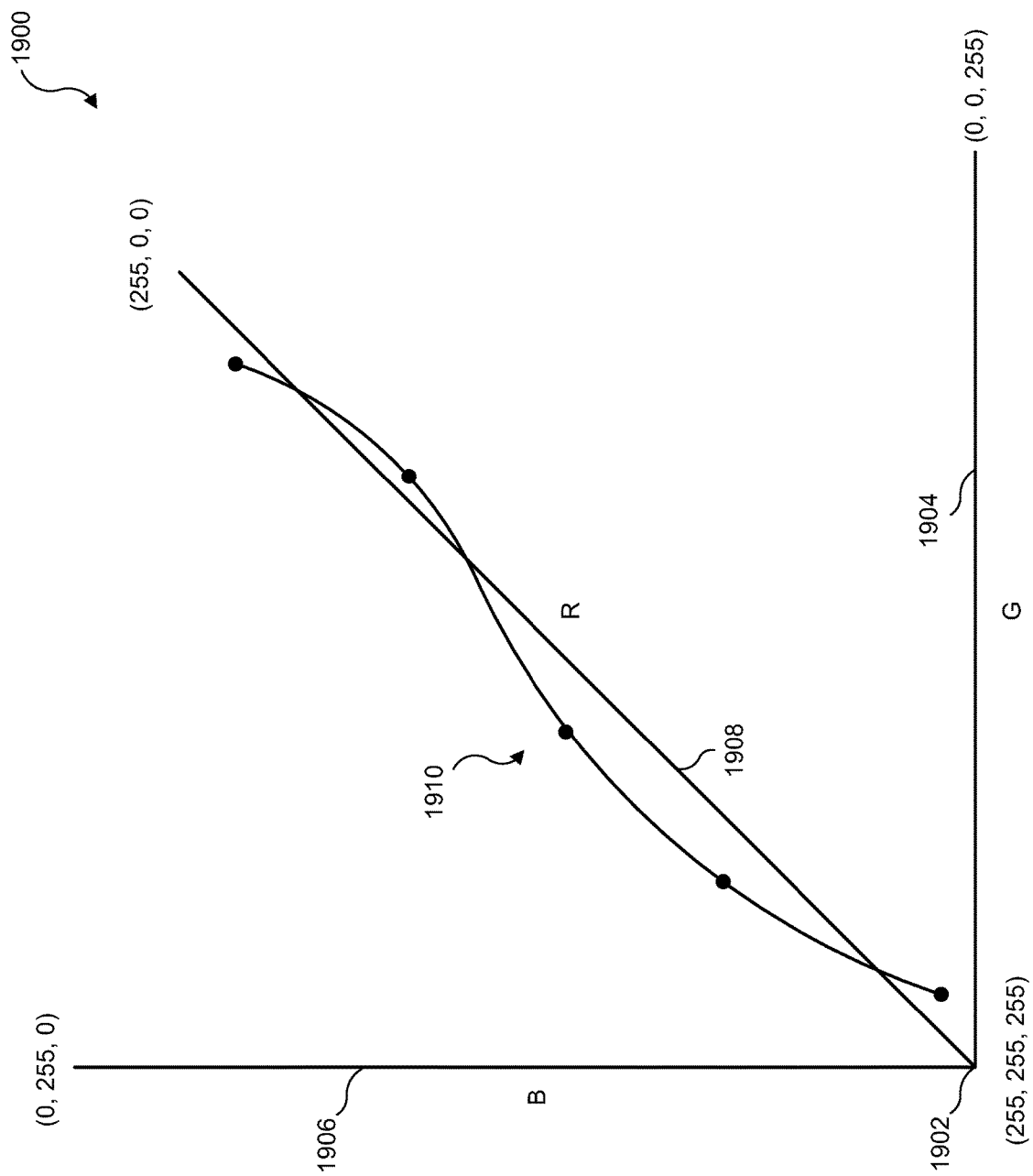
FIG. 19 illustrates a color gradient chart.

Referring now to FIG. 19, there is illustrated a color gradient chart 1900. When the mobile application described herein captures an image of the testing device, in some embodiments each pixel that makes up the test line captured in the image is processed to place it on a color gradient scale. In some embodiments, this placement may be done by examining the RGB values of the pixel. For any given test, there may be a visual color indicator (such as a test line) presented to the user of the test to indicate whether a reaction occurred. The color that is to be presented is known for the given test. Additionally, in some embodiments, the strength of the reaction will affect the strength of the color indicator. For example, if a test is supposed to produce a brown colored indicator, an image can be taken of the colored indicator to examine each pixel of the colored indicator to determine the strength of the color produced on the testing device, which indicates the strength of the reaction, and thus the risk level for the user.

The embodiment illustrated in FIG. 19 uses as an example a set of pixel RGB results for a test that produces a red colored indicator on the test strip when a reaction has occurred. There can be seen an origin point 1902 on the chart 1900, wherein the RGB value is (255, 255, 255) or white. This may represent a no reaction state for the test strip, since the test line on the strip may only appear as a white blank space if no reaction has occurred. An x axis 1904 represents the color green, wherein the amount of green in the pixel decreases as it moves away from the origin in relation to the x axis 1904. A y axis 1906 represents the color blue, wherein the amount of blue in the pixel decreases as it moves away from the origin in relation to the y axis 1906. A diagonal line 1908 running in between the x axis 1904 and the y axis 1906 represents the color red, wherein the diagonal line 1908 running through the center of the chart 1900 is a maximum red color all along the diagonal line 1908. If a pixel has less red than a 255 value, the pixel would be plotted away from the diagonal line 1908 in relation to whichever color is more predominant. For instance, if the pixel has RGB values of (127, 50, 205), a shade of purple, the pixel would be plotted somewhere in the lower right quadrant of the chart 1900. FIG. 19 further illustrates an example plurality of pixel plot points 1910, connected by a curved line, wherein the example plurality of pixel plot points 1910 shows tests results that likely indicate a positive reaction, as the plot points are all located near the diagonal line 1908, demonstrating that the colored indicator was a heavy red color for the most part.

Figure 20:
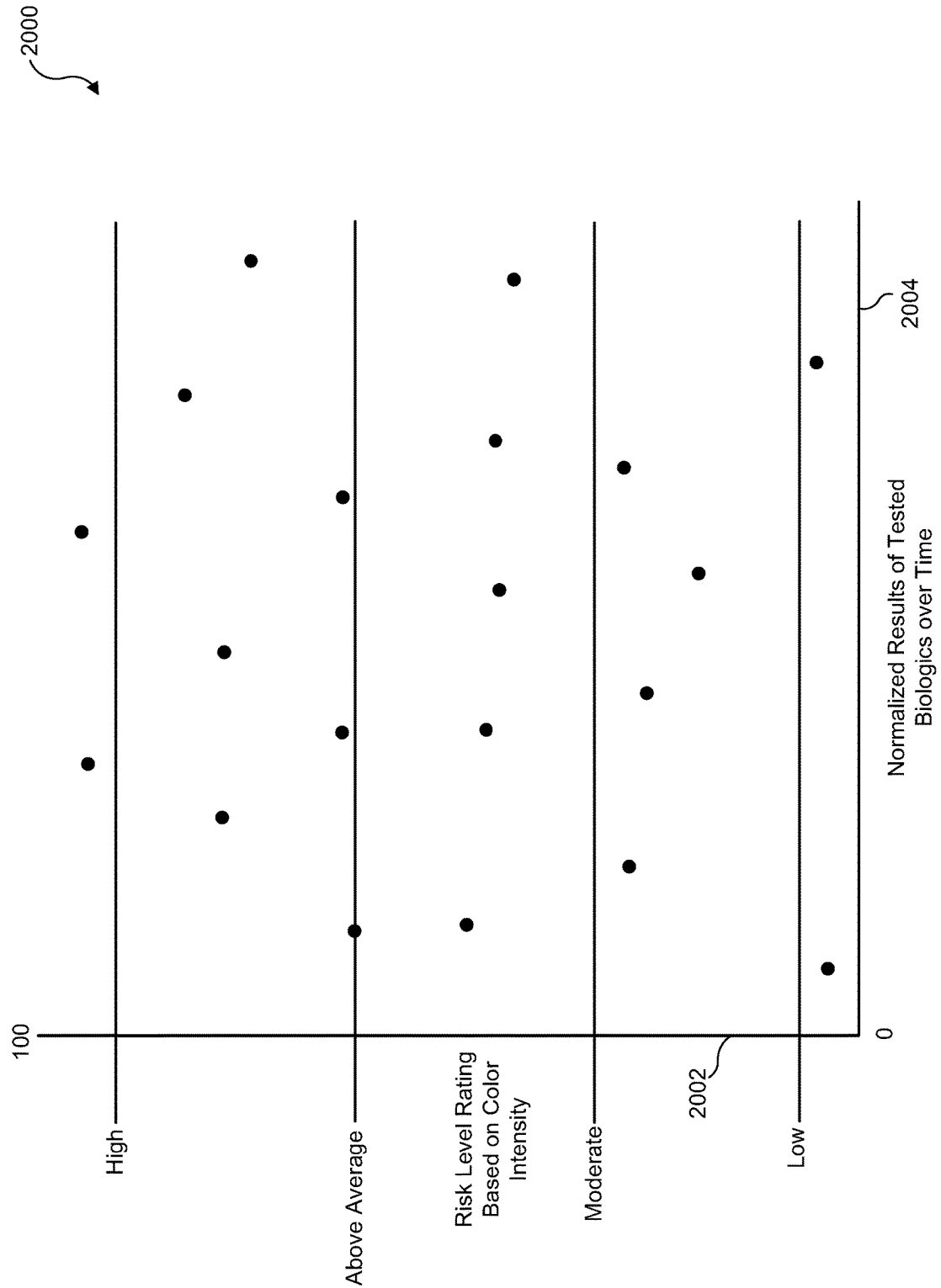
FIG. 20 illustrates a normalized past tests results rating chart.

Referring now to FIG. 20, there is illustrated a normalized past tests results chart 2000. The captured pixels may be normalized into a single value for determining whether there is a likelihood of infection, pregnancy, or whatever else the test is designed to detect. This may be done in various ways. For example, the shade of red in all the pixels may be averaged to reach a single RGB value. Outliers may be left out so that the average is not heavily skewed, especially when there are few outliers present. This RGB value may then be given a value, such as a risk rating, ranging from 0 to 100. For example, an RGB value of (255, 255, 255) would be given a rating of 0. An RGB value of (255, 0, 0) would be given a rating of 100. An RGB value of (205, 150, 75) may be given a rating of 70, and so on. This normalized value may then be used to compare the user of the test to users of past tests to determine a risk level. In some embodiments, the control line and the test line may be captured and the results compared, as well. In addition, the real results of risk levels may also be used to adjust the stored normalized value. For instance, if a particular RGB value that seems to indicate a strong reaction repeatedly was found to not indicate an infection, this value may be adjusted to provide a lower risk rating. For instance, if a physician who saw a patient who had a (205, 150, 75) RGB value later reported to the operator of the server 1206 that further testing showed no infection was present, and if this trend continued substantially as reported by other physicians or medical organizations, subsequent test results by other test users that were near the RGB value of (205, 150, 75) may be given a lower rating.

Chart 2000 illustrates how past tests results may be collected and used to determine the risk of a current test user. A y axis 2002 represents a risk level rating, ranging from 0 at the origin to 100. An x axis 2004 represents time, wherein a plurality of normalized test results is plotted on the chart 2000. The chart 2000 is further divided into sections across the y axis 2002, indicating various risk level thresholds. For instance, and as illustrated in the chart 2000, there may be at certain rating levels different thresholds of risk labeled as low, moderate, above average, and high risk levels. These thresholds may be moved over time as more data is accumulated via users conducting tests and the mobile application storing the data on the tests. When a user conducts a test, the user's normalized rating can be plotted similarly to past test results and weighed against them in order to provide a risk level for the user.

Figure 21:
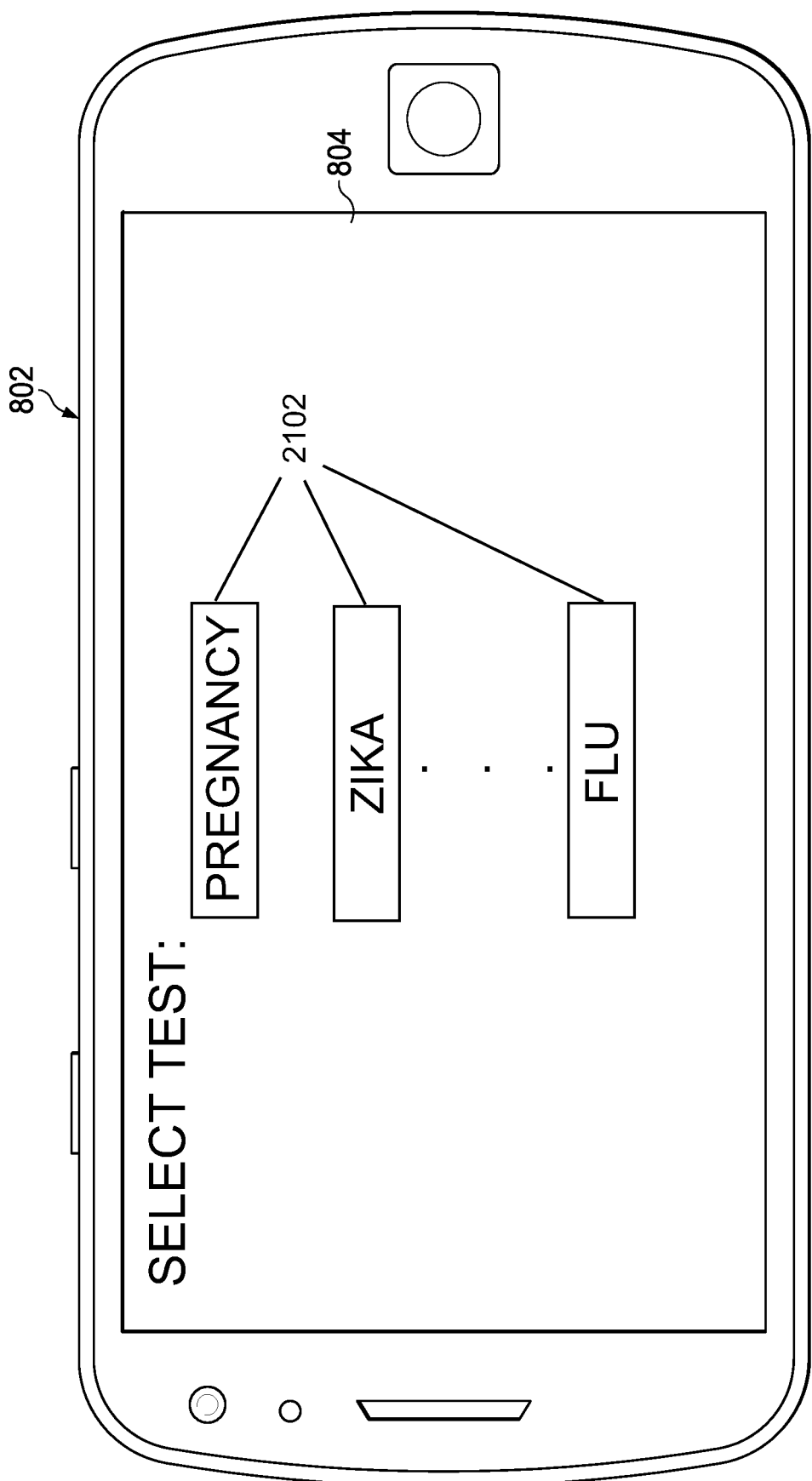
FIG. 21 illustrates a mobile device displaying on a screen a mobile application variable test functionality.

Referring now to FIG. 21, there is illustrated the mobile device 802 displaying on the screen 804 a mobile application variable test functionality. There is displayed on the screen 804 a plurality of test functions 2102. The plurality of test functions 2102 may be buttons that can be selected by a user to switch between tests within the mobile application. This allows for all test functions to be within the same mobile application. For each test run by the mobile application, data for the particular test chosen is utilized in performing the test, pulling the data from the remote server 1206.

Figure 22:
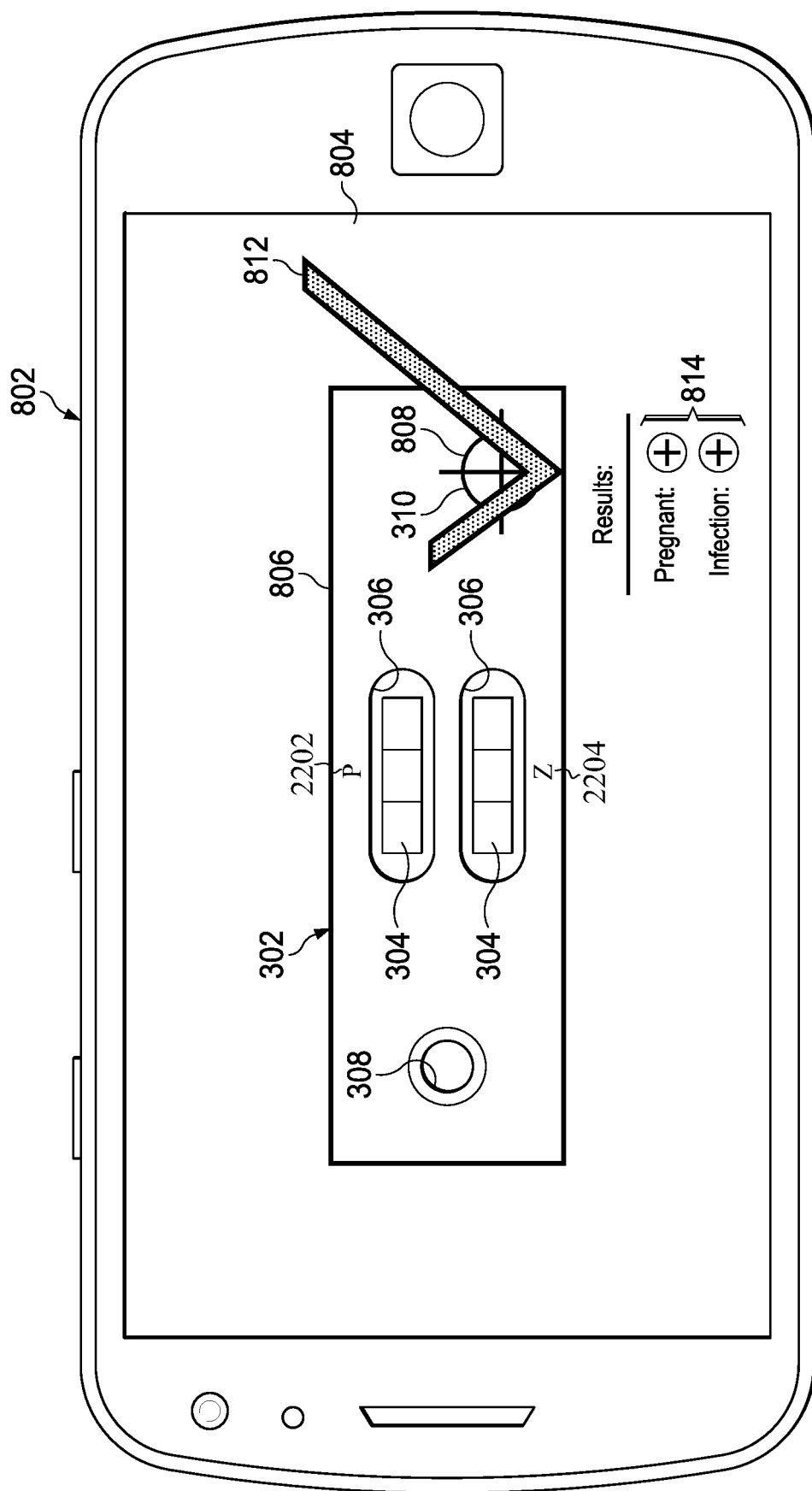
FIG. 22 illustrates the mobile device of FIG. 21, wherein a housing of a testing device also includes thereon test function indicators.

Referring now to FIG. 22, there is illustrated the mobile device 802 of FIG. 8B, wherein the housing 302 of the testing device 300 also includes thereon test function indicators 2202 and 2204. The test function indicators 2202 and 2204 are visual markers located on the housing 302 that identify to the mobile application the types of tests for which the testing device 300 is configured. These indicators may be any symbol, alphanumeric character, shape, etc. that can be added to the surface of the testing device 300. The mobile application is programmed to recognize the indicator and perform the test function associated with the indicator. For example, the embodiment illustrated in FIG. 22 shows a "P" symbol for test function indicator 2202 and a "Z" symbol for test function indicator 2204. In this embodiment, test function indicator 2202 indicates that one test strip in the testing device 300 is a pregnancy test, while test function indicator 2204 indicates that one test strip in the testing device 300 is a Zika test. This is used for merely illustrative purposes, and any recognizable symbol may be used for these two test functions, and any other type of test may have a symbol assigned in this way as well. Further, in some embodiments there may only be one indicator on the housing 302, even if there are multiple tests. This single indicator would be for the combined test. For example, if the testing device 300 of FIG. 22 had a single symbol of "PZ," this would indicate that the testing device 300 is a combined pregnancy and Zika testing device, allowing for the mobile application to recognize such and perform each test with knowledge of which strip is associated with which test based on the stored data on the testing device associated with the "PZ" symbol.

Figure 23:
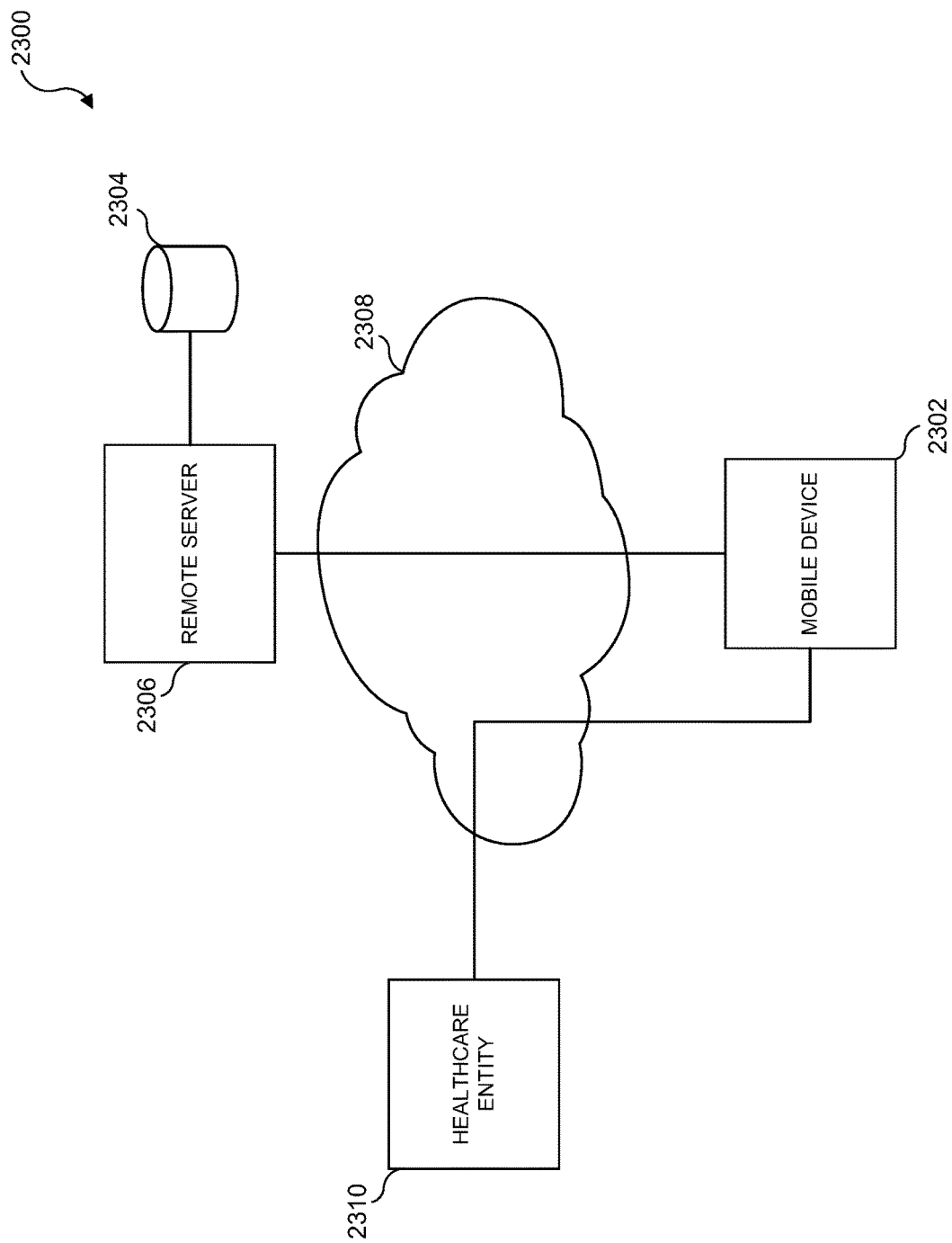
FIG. 23 illustrates one embodiment of a medical code correlation system.

Referring now to FIG. 23, there is illustrated a medical code correlation system 2300. The system 2300 includes a mobile device 2302, which is configured to run the mobile application described herein. The mobile device 2302 is connected to a database 2304 disposed on a server 2306, over a network 2308. To correlate a medical code, the mobile device first passes a diagnostic test identifier to the remote server. This identifier allows for the type of test being used by the user of the mobile device 2302 to be determined. The identifier may simply be the name of the test, may be a number associated with the test, or any other means of identifying the test being performed by the user of the mobile device 2302. This may be done when the phone capture the image of the testing device to process the results, or the user may enter the test to be performed before a test is conducted, at which time the mobile device 2302 may pass the identifier to the remote server. In other embodiments, the diagnostic test identifier may even be the medical code. For example, if the diagnostic test is a strep test, the identifier may be G0435, an HCPCS code for a rapid immunoassay test, or any other appropriate medical code.

Once the physical test results of the diagnostic test is captured, and once the results are processed by the mobile device 2302 or the server 2306, the results are also received by the server. Once the server 2306 has the diagnostic test identification and the results of the test, the server 2306 may then correlate the specific test and the results with appropriate medical codes stored within the database 2304. It will be understood that the database 2304 may be physically located with the server 2306, or the database 2304 may be a remote database, such as a centralized database that allows entities within the healthcare industry to retrieve the latest medical codes. The medical codes assigned may then be transferred from the mobile device 2302 to a healthcare entity 2310. In other embodiments, the medical codes may be transferred from the server 2306 to the healthcare entity 2310. The healthcare entity 2310 may be a physician, a hospital, a pharmacy, an insurance company, or any other entity that may provide the user with further assistance.

Figure 24:
FIG. 24 illustrates one embodiment of a strep home retail test codes table.

Referring now to FIG. 24, there is illustrated a strep home retail test codes table 2400. The table 2400 lists the various medical codes that may be associated with a home testing device that is used to test for a streptococcal infection. The table 2400 is representative of the types of codes that may be stored in the database 2304 in relation to a particular retail strep test device. The table 2400 lists a diagnosis code of J02.0, an ICD-10-CM code for streptococcal pharyngitis. The table 2400 also lists an HCPCS code of G0435, which is a code for a rapid antibody test. The table 2400 also lists an NDC code of 54569-5182-0, which is the NDC code for an amoxicillin prescription. Thus, when the server 2306 assigns the medical codes to the testing device or the test results, various codes may be produced. The example shown in table 2400 shows that the strep home retail testing device is assigned the HCPCS code of G0435 to indicate the type of test it is, a rapid antibody test. If the test results come back as positive, the server assigns the ICD-10-CM code to this event, indicating a streptococcal throat infection. In response to these positive test results, the server 2306 provides the NDC code for amoxicillin as a recommended prescription to give to the user to treat the infection.

In some embodiments, this prescription may be passed to a pharmacy so that the pharmacy may fill the prescription for the user to pick up, or to be delivered to the user. In some embodiments, the medical codes and other information may be passed to a physician for review. This physician may be the primary care physician of the user, allowing the user to set an appointment to go over the test results and get a prescription from the physician. In other embodiments, the physician may be a telemedicine physician that either the user contacts, the physician sets up a telemedicine conference, or the system described herein automatically initiates in response to the test results. The physician may alter the recommended prescription provided by the system, may conduct additional testing, or otherwise handle the situation as he or she sees fit as a physician. In addition, in some embodiments, the medical codes may be passed to an insurance company to seek reimbursement for the testing device, the prescription, the visit with the physician, or any other costs that arise from this testing event. To accomplish such, the user may have provided his or her insurance information when signing up to use the mobile application in conjunction with the various testing devices provided.

Figure 25:
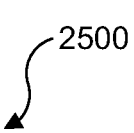
FIG. 25 illustrates one embodiment of a combined pregnancy and Zika home retail test codes table.

Referring now to FIG. 25, there is illustrated a combined pregnancy and Zika home retail test codes table 2500. The table 2500 lists the various medical codes that may be associated with a home testing device that is used to test for both pregnancy and a Zika infection. The table 2500 is representative of the types of codes that may be stored in the database 2304 in relation to a particular retail pregnancy/Zika testing device. The table 2500 has a pregnancy codes column and a Zika codes column. The pregnancy codes column lists a diagnosis code of Z33.1, an ICD-10-CM code for a pregnant state. The pregnancy codes column also lists an HCPCS code of G8802, which is a code for a pregnancy test. The pregnancy codes column also lists an NDC code of 42192-321-30, which is the NDC code for prenatal vitamins. The Zika codes column lists a diagnosis code of A92.5, an ICD-10-CM code for the Zika virus. The Zika codes column also lists an HCPCS code of G0435, which is a code for a rapid antibody test. The Zika codes column also lists an NDC code of 50580-501-30, which is the NDC code for prescription strength Tylenol. In some embodiments, instead of separate codes for each type of test performed, there may be a single code assigned to, for example, a combined pregnancy and Zika test, or even a single code for a pregnant with Zika infection state.

It will be understood that the codes listed in FIGS. 24-25 are examples of how the system may assign codes to a testing event. The use of the specific codes and the types of codes (ICD-10-CM, HCPCS, and NDC codes) are merely used for illustrative purposes; any type of codes may be used and the specific codes listed in FIGS. 24-25 may be other, more appropriate, codes for the particular testing device, diagnosis, etc. Different types of codes include, but are not limited to, ICD-9-CM, ICPC-2, NANDA, Read code, SNOMED, CCI, CDT, NIC, NMDS, NOC, CCAM, OPCS-4, or other codes.

Figure 26:
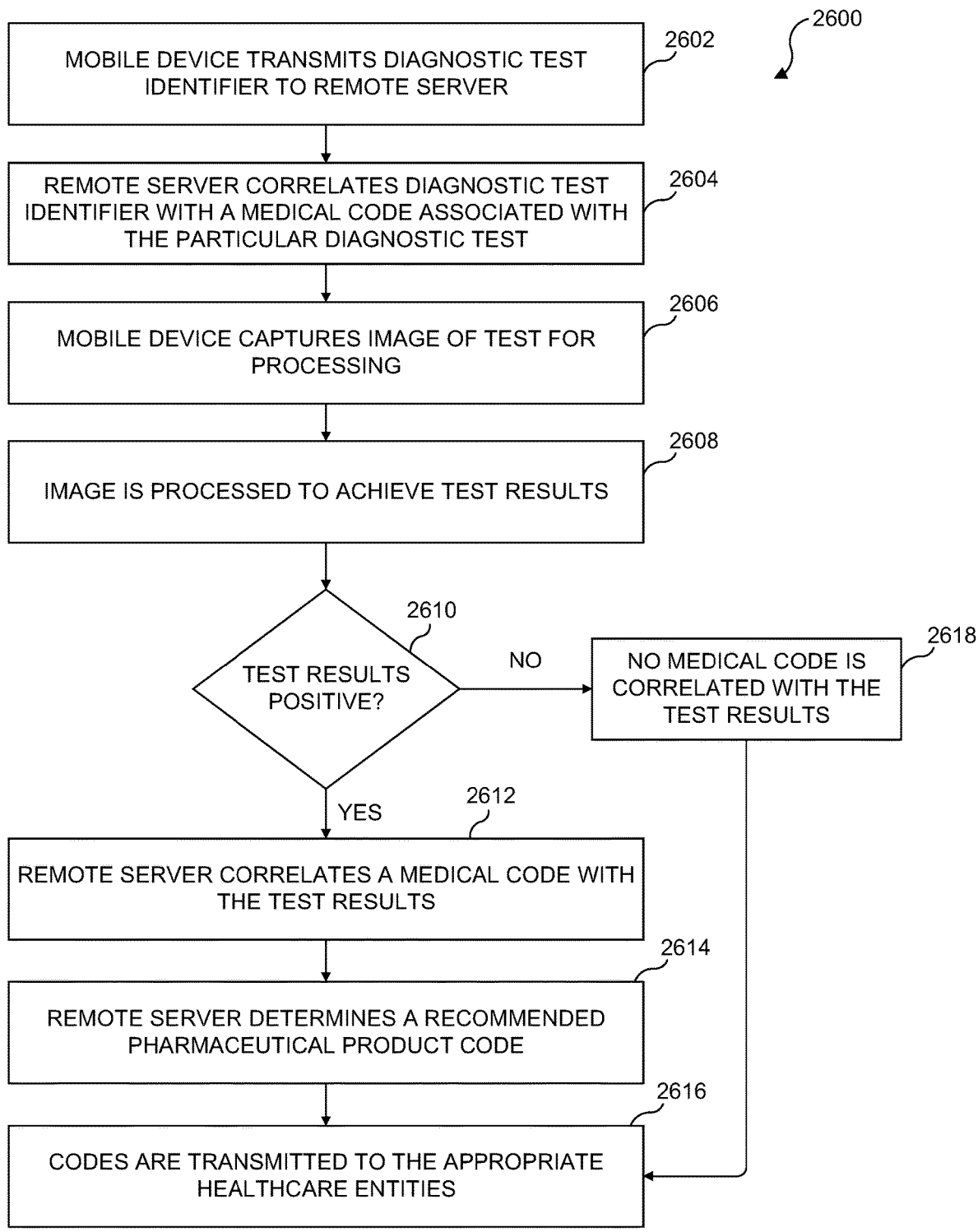
FIG. 26 illustrates flowchart of one embodiment of a medical code correlation process.

Referring now to FIG. 26, there is illustrated a flowchart of one embodiment of a medical code correlation process 2600. The process begins at step 2602 where the mobile device 2302 running the application described herein transmits a diagnostic test identifier to the remote server 2306. At step 2604, the remote server 2306 correlates the diagnostic test identifier with a medical code associated with the particular diagnostic test. This identifier allows for the type of test being used by the user of the mobile device 2302 to be determined. The identifier may simply be the name of the test, may be a number associated with the test, or any other means of identifying the test being performed by the user of the mobile device 2302. This may be done when the phone capture the image of the testing device to process the results, or the user may enter the test to be performed before a test is conducted, at which time the mobile device 2302 may pass the identifier to the remote server. In other embodiments, the diagnostic test identifier may even be the medical code. For example, if the diagnostic test is a strep test, the identifier may be G0435, an HCPCS code for a rapid immunoassay test, or any other appropriate medical code.

The process then flows to step 2606, where the mobile device 2302, as part of the overall operation of the system and mobile application described herein, capture an image of the testing device for processing. At step 2608, the image is processed to achieve the test results. Such processing may be performed on the mobile device 2302, on the remote server 2306, another server, or any other device that may be interfaced with the system disclosed herein. The process then flows to decision block 2610, where it is determined whether the test results indicated a positive result (positive infection, pregnancy, or other outcomes). If the test result is positive, the process flows to step 2612, where the remote server 2306 correlates a medical code with the test results. As described herein, components other than the remote server 2306 may correlate the test results with a medical code, such as a centralized server and database used in the healthcare industry to retrieve medical codes. The process then flows to step 2614 to assign a recommended pharmaceutical product based on the test results. This may be an NDC code for a product, and there may even be provided a prescription for such. At step 2616, the codes are transmitted to the appropriate healthcare entities, such as a physician, a pharmacy, or other entities.

If at decision block 2610 it is determined that the test results are negative, the process instead flows to step 2618, where no medical code is correlated with the test results. This provides that no diagnosis code if provided, since the test results indicate that the user is not positive for the condition being tested. However, a medical code for the test itself, determined at step 2604, may still be applicable in this scenario, because the user still used the diagnostic test, and therefore may still be reimbursed for the cost of the test, if the user's insurance company chooses to do so. The user's physician may also want to see the test results, even if they are negative, and the code for the test and the negative results may still be transmitted to the physician. Therefore, after step 2618, the process then flows to step 2616 to transmit the codes (in this case, the code for the testing device product) to the appropriate healthcare entities. The test results themselves may also be transmitted.

Figure 27:
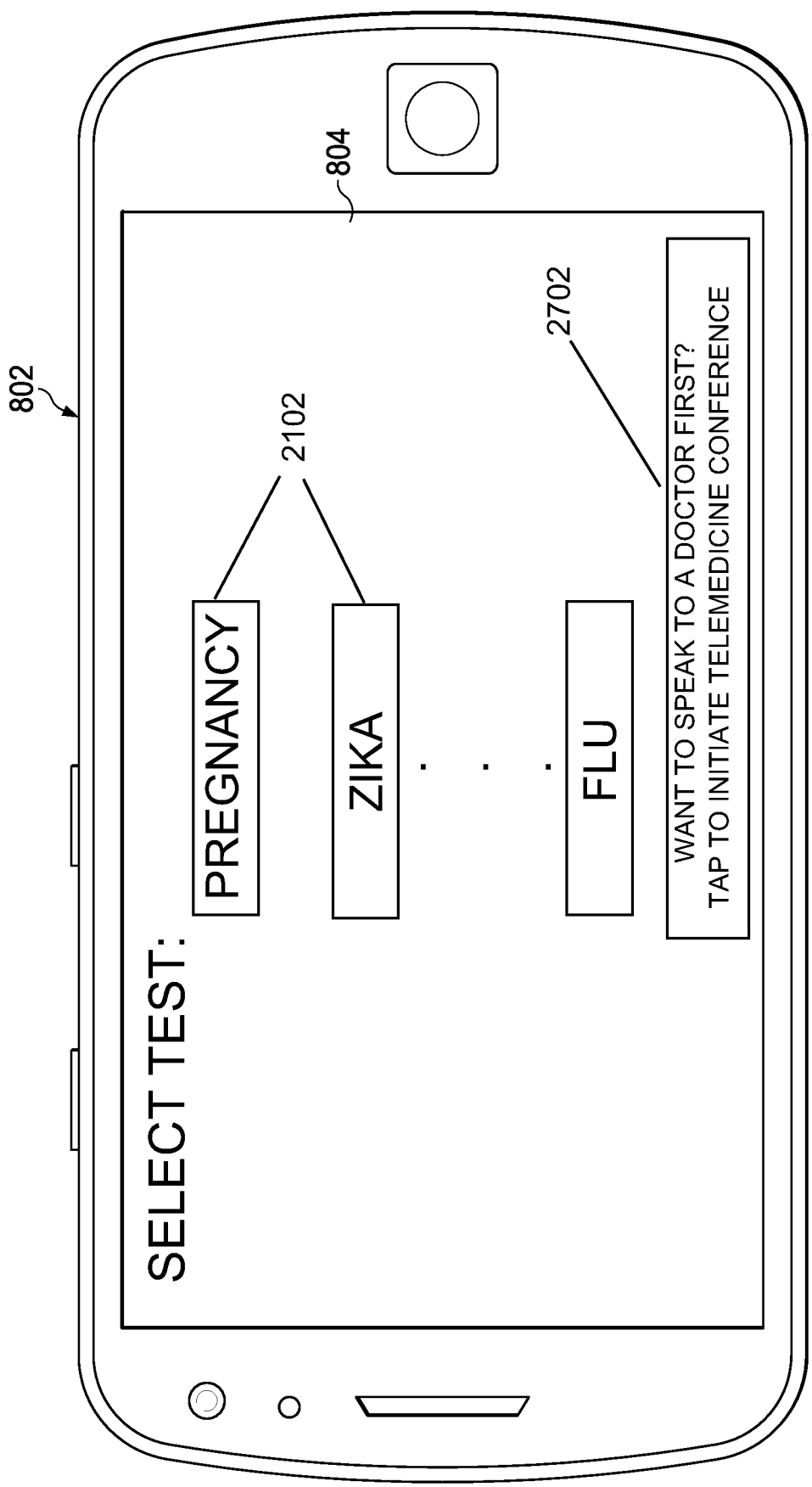
FIG. 27 illustrates one embodiment of a telemedicine initiation option within a mobile application.

Referring now to FIG. 27, there is illustrated one embodiment of a telemedicine initiation option within a mobile application. The mobile application and system described herein is predominantly meant to first test a patient for a medical condition, and then recommend an action, such as seeing a physician. However, the system allows for telemedicine conferences to be initiated, and therefore functionality may exist wherein a user can request a telemedicine conference with a physician at any time while using the mobile application, in order to receive a diagnosis or simply to ask questions. Thus, FIG. 27 again shows the plurality of test functions 2102 displayed on the screen 804. In addition to these options, an additional option is presented to the user. This option is a telemedicine conference button 2702 that allows a user to initiate a telemedicine conference with a qualified telemedicine provider. This button 2702 is shown on the screen where the user selects the type of test to be performed, but the button 2702 may be presented within the user interface on any screen of the mobile application.

Figure 28:
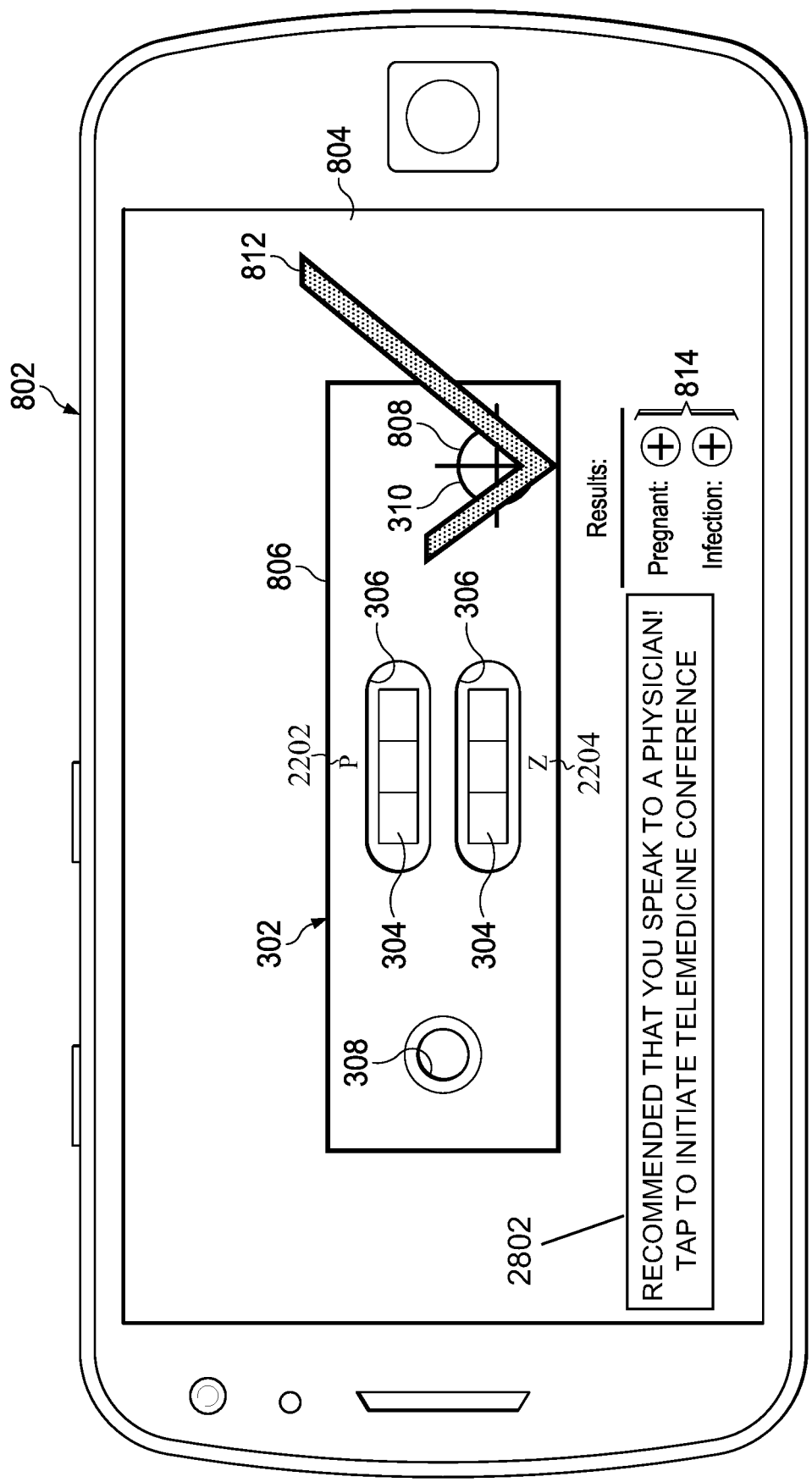
FIG. 28 illustrates another embodiment of a telemedicine initiation option within a mobile application.

Referring now to FIG. 28, there is illustrated another embodiment of a telemedicine initiation option within a mobile application. There is shown on the screen 804 the test results as previously shown on FIG. 22, which indicate positive pregnancy and Zika test results. In such a situation where the test results indicate a possible serious medical condition, a button 2802 may appear to the user on the screen 804. The button 2802 may have a warning message within, urging the user to seek a consultation with a physician to talk about the user's options in light of the positive test results, and inviting the user to tap the button 2802 to initiate a telemedicine conference with a physician. Tapping the button 2802 will initiate such a telemedicine conference. The physician that is connected with for the conference may be an on-call physician that has agreed to make his or her services available through the system described herein, the telemedicine conference may use an existed telemedicine conference platform and physician base, the user's primary care physician may be a user of the system and mobile application, allowing for them to be used as the default telemedicine contact for the user, or other methods of making physicians available for a conference with the users of the mobile application may be provided.

Figure 29:
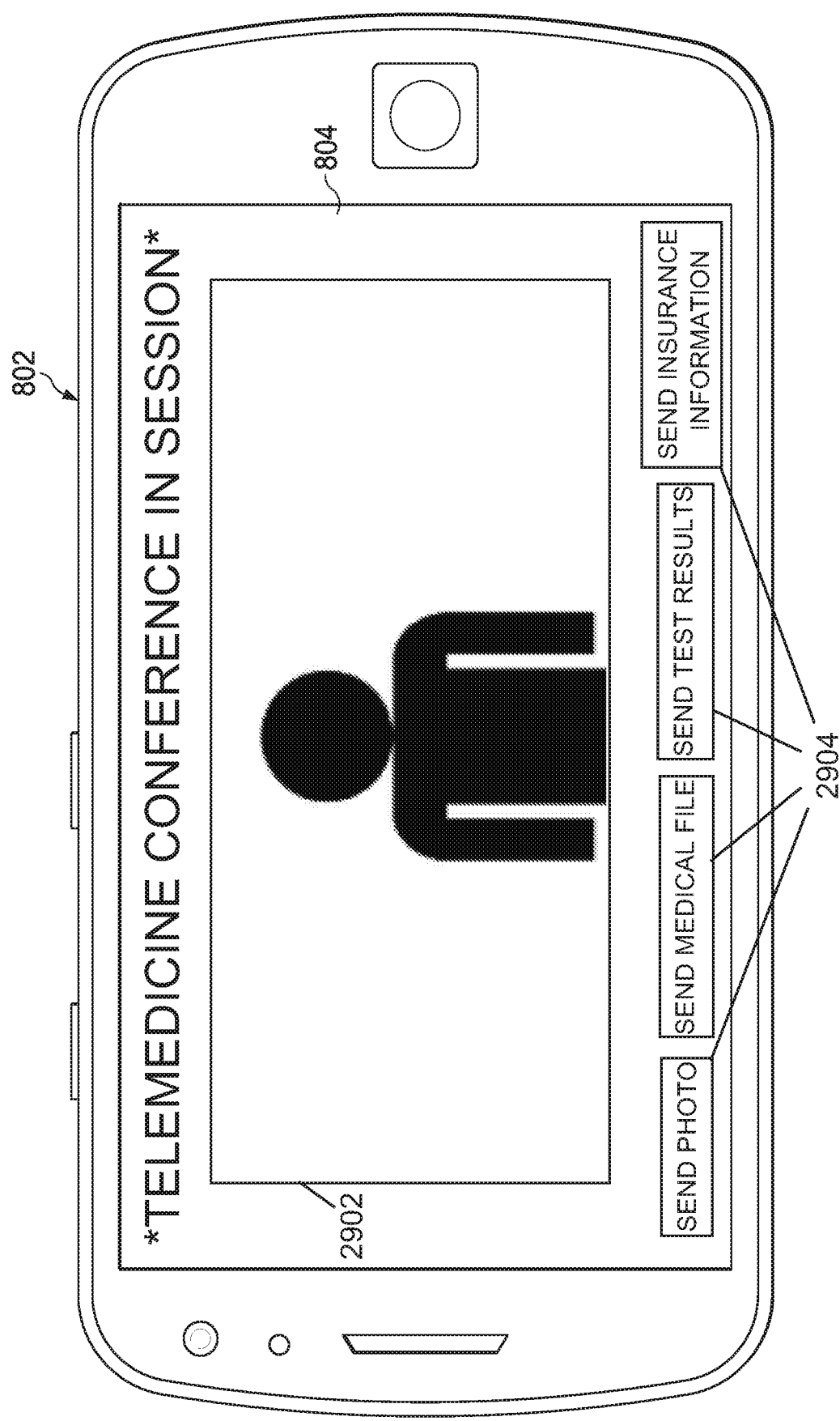
FIG. 29 illustrates one embodiment of a telemedicine conference session on a mobile device.

Referring now to FIG. 29, there is illustrated one embodiment of a telemedicine conference session on a mobile device. During a telemedicine conference that has been initiated as described herein, the user is presented with a video conference window 2902 on the screen 804. The video conference window 2902 allows for user to see the physician that is providing the telemedicine services to the user. It will be understood that the physician may have a similar video window on the device being used by the physician that allows the physician to see the user. This allows the physician to make some visual observations of the user's condition. In addition to the video conference window 2902, the user is presented with a plurality of actions 2904 on the screen 804. The plurality of action 2904 may be buttons that allow the user to provide the physician with further information. For example, one button may allow for the user to send a photograph to the physician, such as a photograph of the user's symptoms, or of the user's test results presented on the testing device. One button may also provide an option for sending the user's medical file to the physician, so that the physician can review the user's medical history or other important information. This medical file may include all the information accumulated from all tests performed by the user under the system described herein, and may also include all other medical history information. The user may have provided a copy of his or her medical history, or such may have been retrieved from a central electronic medical records system.

Other actions that may be provided in the plurality of actions 2904 may be a button to send test results to the physician. This would allow the user to send the test results of the latest test the user took before initiating the telemedicine conference, or it may allow for the user to choose the test. The plurality of actions 2904 may also include a button for sending the user's insurance information to the physician. The user may have provided this information within the mobile application and had it stored to the server, or this information may have been pulled for the user based on the user's identification information. This option allows the user to give the physician insurance information so that the physician can use the user's insurance for reimbursement of the telemedicine services, and may even set up reimbursement to the user for certain services or products, such as the testing device used for the test.

Figure 30:
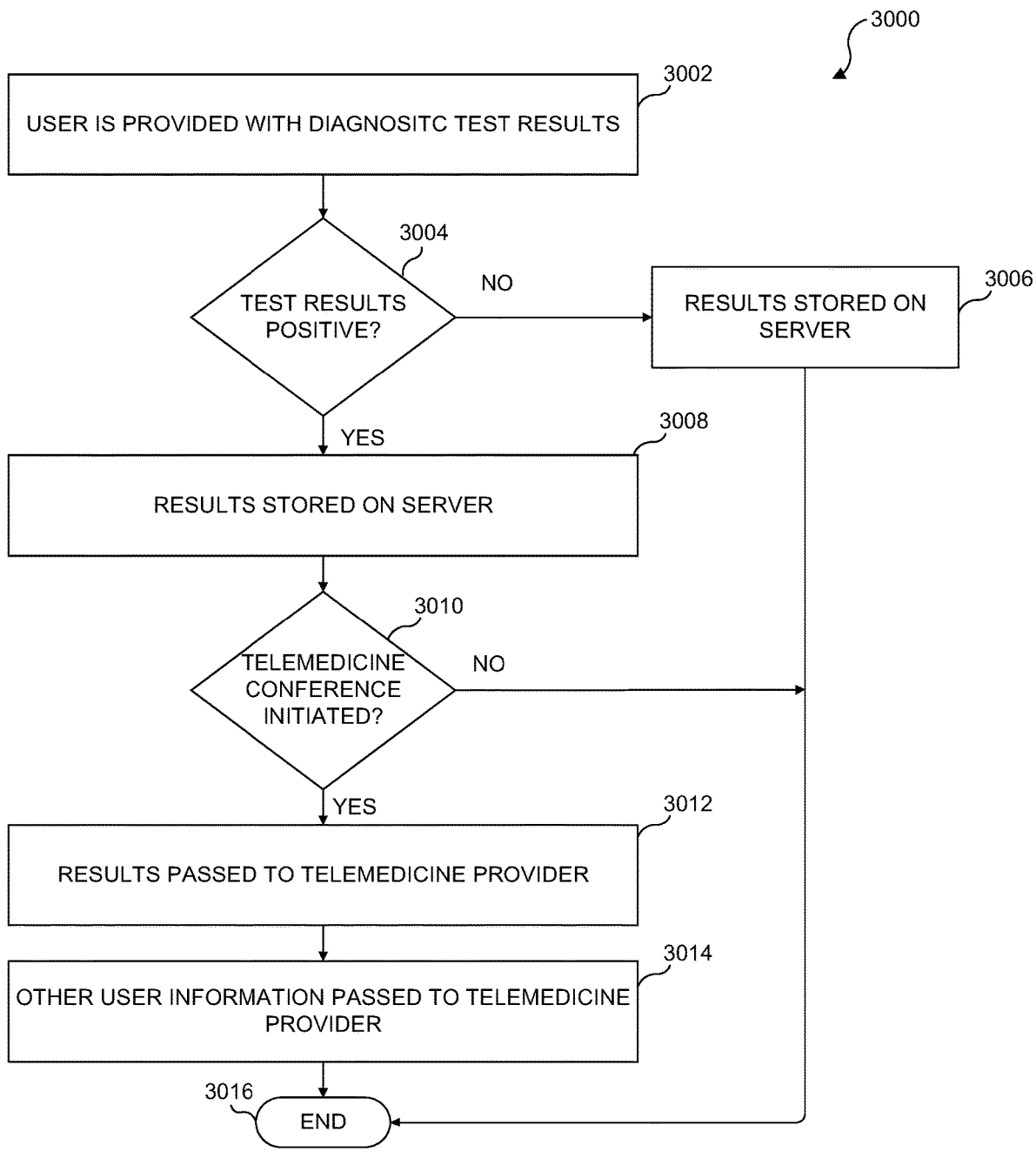
FIG. 30 illustrates a flowchart of one embodiment of a medical file handoff process.

Referring now to FIG. 30, there is illustrated a flowchart of one embodiment of a medical file handoff process 3000. The process 3000 starts at step 3002 where a user is provided with diagnostic test results at the conclusion of a performance of a test. At decision block 3004, it is determined whether the test results provide a positive result. If not, at step 3006 the results are stored on the server of the system described herein and the process ends at end block 3016. If the results are positive, the process flows to step 3008 where the results are stored on the server. At step 3010, it is determined whether a telemedicine conference has been initiated. This initiation may have been selected as described with respect to FIGS. 27 and 28, may have been initiated automatically due to the results provided, or may have been initiated in some other way. If the telemedicine conference was not initiated, the process ends at end block 3016. If the telemedicine conference was initiated, the process flows to step 3012 where the test results are passed to the telemedicine provider participating in the telemedicine conference. The process then flows to step 3014, where other user information is passed to the telemedicine provider. The process then ends at end block 3016.

The passing of the results to the telemedicine provider and other information at steps 3012 and 3014 may be performed by the user's mobile device, wherein the mobile device sends the files to the telemedicine provider. The passing may also be done by the server of the system described herein, wherein the results and other information was previously stored to the server and the server then passes the results and other information to the telemedicine provider as a result of the server being notified of a telemedicine conference initiation. The other user information of step 3014 may be any information needed by the telemedicine provider, such as past medical records and history of the user, past test results, insurance information, or any other information.

Figure 31:
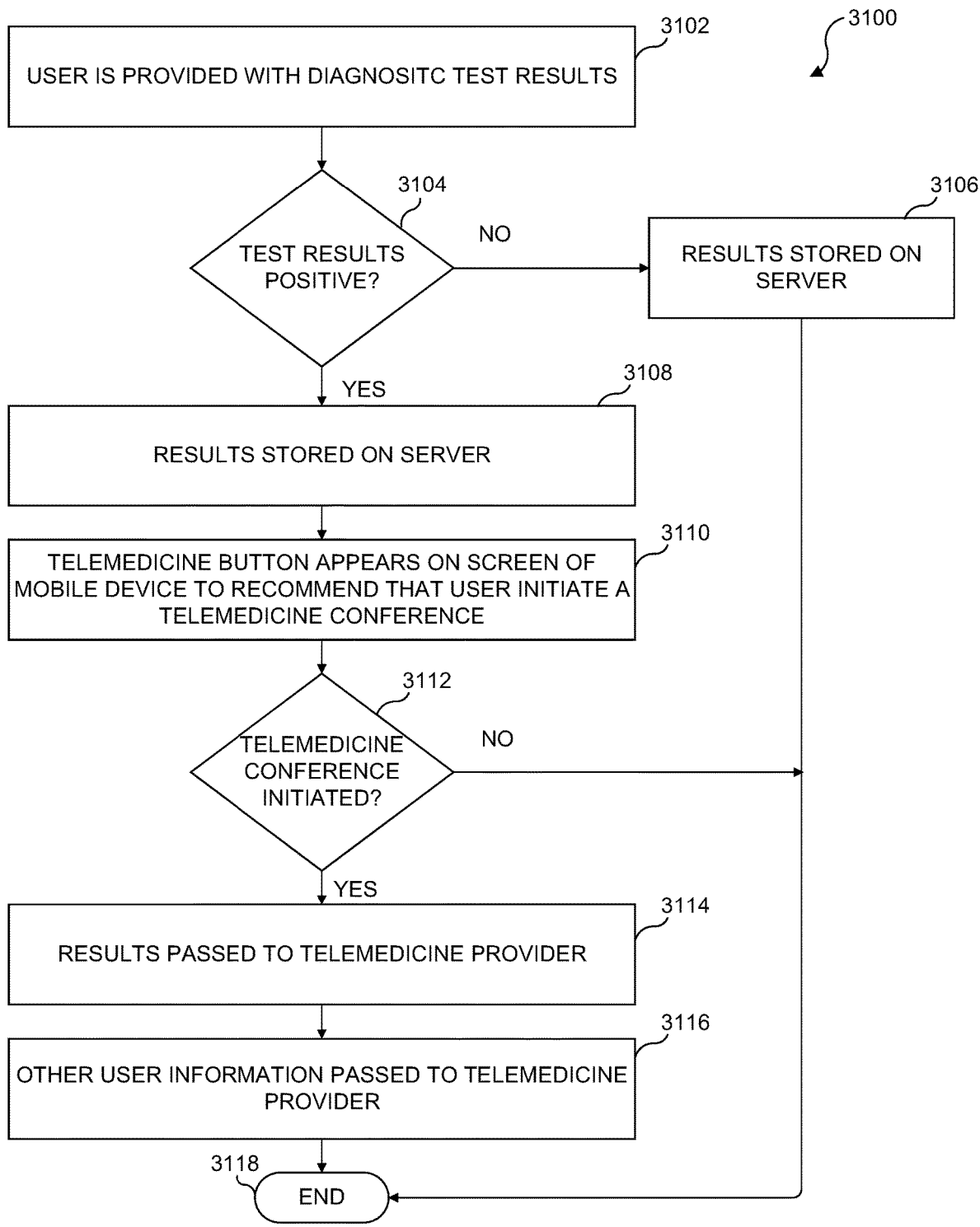
FIG. 31 illustrates a flowchart of one embodiment of a telemedicine conference initiation process.

Referring now to FIG. 31, there is illustrated a flowchart of one embodiment of a telemedicine conference initiation process 3100. The process 3100 starts at step 3102 where a user is provided with diagnostic test results at the conclusion of a performance of a test. At decision block 3104, it is determined whether the test results provide a positive result. If not, at step 3106 the results are stored on the server of the system described herein and the process ends at end block 3118. If the results are positive, the process flows to step 3108 where the results are stored on the server. At step 3110 a telemedicine button is presented to the user on the screen of the mobile device, similar to that shown in FIG. 28. This button recommends to the user that the user initiate a telemedicine conference, since the test results indicate a positive reaction. At step 3112, it is determined whether a telemedicine conference has been initiated. This initiation may have been selected as described with respect to FIGS. 27 and 28, may have been initiated automatically due to the results provided, or may have been initiated in some other way. If the telemedicine conference was not initiated, the process ends at end block 3118. If the telemedicine conference was initiated, the process flows to step 3114 where the test results are passed to the telemedicine provider participating in the telemedicine conference. The process then flows to step 3116, where other user information is passed to the telemedicine provider. The process then ends at end block 3118.

The passing of the results to the telemedicine provider and other information at steps 3114 and 3116 may be performed by the user's mobile device, wherein the mobile device sends the files to the telemedicine provider. The passing may also be done by the server of the system described herein, wherein the results and other information was previously stored to the server and the server then passes the results and other information to the telemedicine provider as a result of the server being notified of a telemedicine conference initiation. The other user information of step 3116 may be any information needed by the telemedicine provider, such as past medical records and history of the user, past test results, insurance information, or any other information.

In some environments ambient lighting in a space cannot be controlled, resulting in images taken by a mobile device of a test kit to have different color temperatures. Additionally, the optical design of cameras that introduce color shifts due to chromatic aberration and other light lens interactions may produce images different in color from other cameras. A lighting sensor in a mobile device may also automatically adjust acquisition parameters. The camera software of the mobile device may also perform processing of the image that alters the colors in the image to be more pleasing to a human observer. This causes each image acquired via a mobile device to have a unique color balance. For example, green colors in one image may not match the green colors in another image. To account for this, various methods may be used to control the color balance.

One such method is to perform colorimetric analysis, comparison, and quantification. Colorimetric analysis is a method of determining the concentration of a chemical element or chemical compound in a solution with the aid of a color reagent. It is applicable to both organic compounds and inorganic compounds and may be used with or without an enzymatic stage. In physical and analytical chemistry, colorimetry is a technique that is used to determine the concentration of colored compounds in solution. Colorimetry can be used to determine the concentration of any colored substance. Methods of taking colorimetric measurements may be made by using a light which passes through a color filter. The light is then passed through a small box or cuvette with the actual chemical substance. The wavelength of the light received is then measured to determine the concentration of the target in the substance.

To introduce colorimetric analysis to the testing devices disclosed herein, the lighting environment may be controlled using by introducing controlled light sources to direct light into the environment or on the subject of the image. The light sources introduced may be of various intensities, colors, etc., depending on the type of test being performed. For example, a standard white light may be applied to an environment to wash out colors in the image, or colored lights, such as a green light, may be introduced to emphasize certain colors or filter out other colors.

Figure 32:
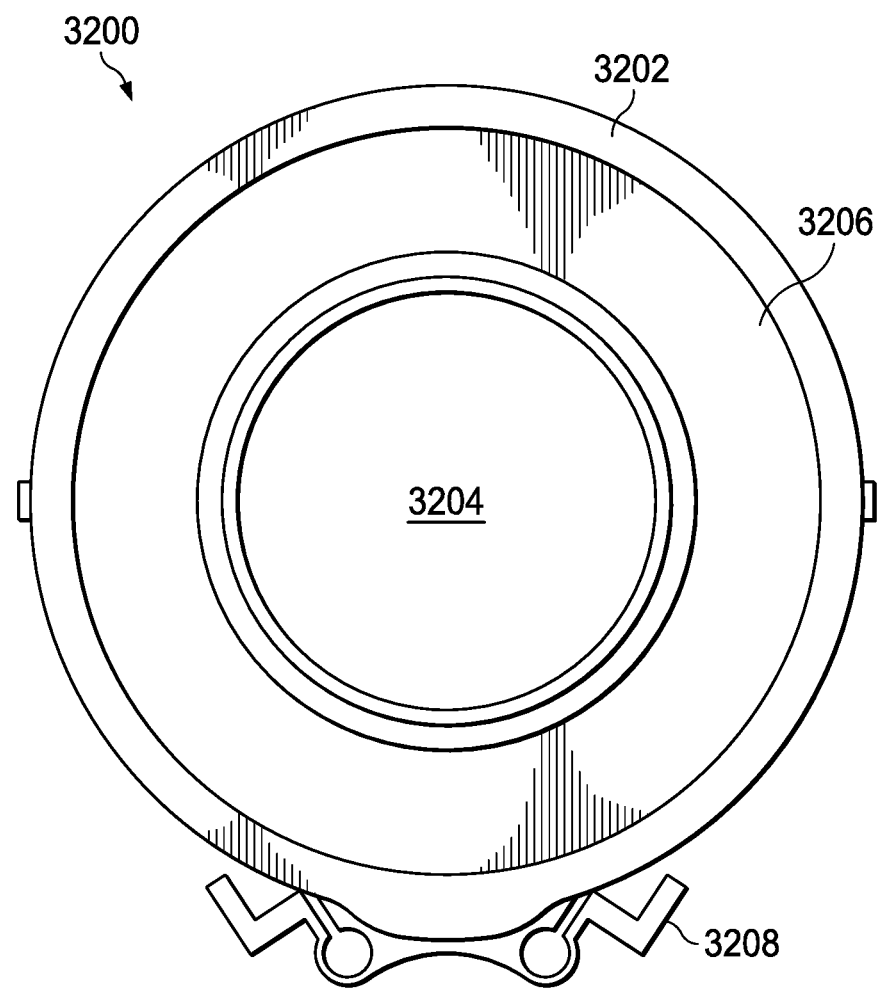
FIG. 32 illustrates an attachable lighting apparatus.

Referring now to FIG. 32, there is illustrated an attachable lighting apparatus 3200. The lighting apparatus 3200 includes a circular body 3202 having an aperture 3204 in the center therethrough. The circular body 3202 may be of a thickness to allow one or more lights 3206 to be disposed within. The one or more lights 3206 may be a single circular light that fits within the circular body 3202. If the one or more lights 3206 include more than one light, the one or more lights 3206 may include series of lights arranged in a circular pattern around the circular body 3202. The one or more lights 3206 may be light emitting diodes (LEDs) or other types of lighting elements. In some embodiments, the one or more lights 3206 may be a white light in order to provide a brighter environment and wash out other color hues from the environment during the taking of an image using a mobile device. In other embodiments, the one or more lights 3206 may be of a particular color. For example, the one or more lights 3206 may be a red light.

If the color of the test line (and the control line) after a successful reaction is red for a particular test strip, red light will be reflected, causing the test line to still appear red. However, if the test line does not undergo a strong reaction, and, for example, the test line appears to be a shade of pink or magenta, rather than true red, the red light would still be reflected, while traces of blue color in the pink or magenta color on the test line would be filtered out. To emphasize a contrast between a red test line and a pink or magenta test line, blue light could instead by cast upon the test strip when taking an image of the test strip. In the case of a strong red test line being produced as a result of the test, the blue light would be absorbed, causing the test line to appear black, which may be useful in determining whether the red test line actually is a strong reaction or not. For example, if it is a strong reaction, the resultant image should show a completely or nearly solid black line. However, if the test line instead was a pink or magenta shade, some blue light may still be reflected, causing the resultant image to show test line having a blue hue. The control line also may be used in the analysis. Since the control line should react strongly despite the result on the test line, in the above example of a red line with blue light, the control line should appear black, which may be contrasted against the test line which may not completely black.

Other colors may be used in this way to emphasize and more closely evaluate the test line. For example, a color may be introduced that is not a primary color, such as magenta. If the test line is again red, magenta light would cause red to be reflected back, while absorbing the blue in the light. If the test line is not a strong red, some of the blue in the magenta light may still be reflected back, indicating a weaker reaction.

The one or more lights 3206 may be covered by a protective barrier made of plastic, glass, or other materials that allow light to pass through the protective barrier while protecting the one or more lights 3206 from damage. The lighting apparatus 3200 may further include a clip 3208 for attaching the lighting apparatus 3200 to another device, such as a mobile device. The clip 3208 may have a hinged clamp portion that clamps onto a mobile device, may be applied with an adhesive, or may be fixed using fixation devices such as pins or screws to a mobile device. The aperture 3204 may have a diameter large enough to fit over a lens of a camera on a mobile device such that the lens is able to operate to take images while the lighting apparatus 3200 is attached to the mobile device, with the circular body 3202 surrounding the lens without covering any portion of the lens.

Figure 33:
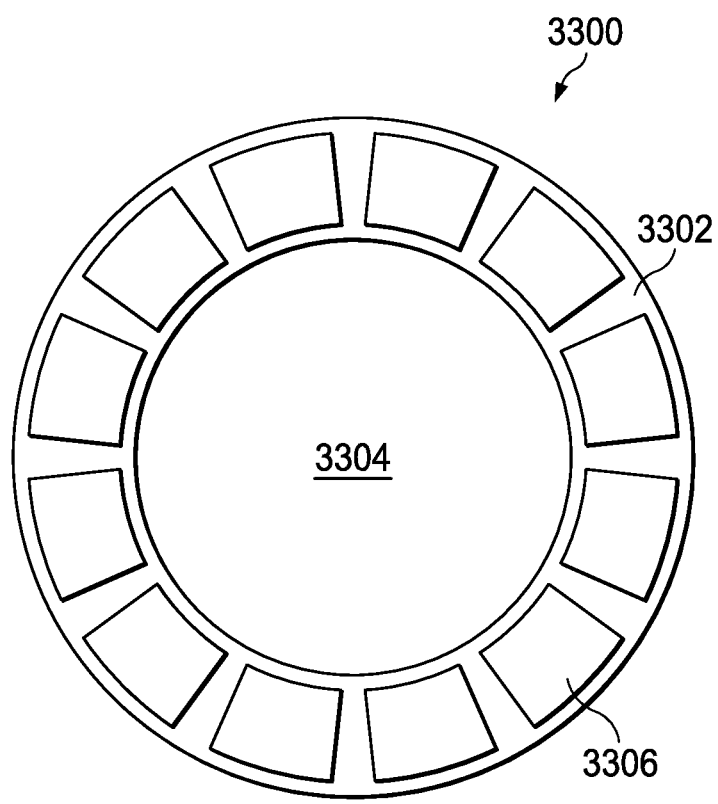
FIG. 33 illustrates a light spectrum apparatus.

Referring now to FIG. 33, there is illustrated a light spectrum apparatus 3300. The light spectrum apparatus 3300 includes a circular body 3302 having an aperture 3304 in the center therethrough. The circular body 3302 may be of a thickness to allow a plurality of lights 3306 to be disposed within. The plurality of lights 3306 include more than one light, the plurality of lights 3206 may include series of lights arranged in a circular pattern around the circular body 3202. The plurality of lights 3306 may be light emitting diodes (LEDs) or other types of lighting elements. The plurality of lights 3306 may be each be a specific color, to provide a variety of colors onto the subject. The plurality of lights 3306 may be covered by a protective barrier made of plastic, glass, or other materials that allow light to pass through the protective barrier while protecting the plurality of lights 3306 from damage. The light spectrum apparatus 3300 may further include a clip such as that described with respect to the lighting apparatus 3200 and as further described herein, to clip the light spectrum apparatus 3300 to another device, such as a mobile device. The aperture 3304 may have a diameter large enough to fit over a lens of a camera on a mobile device such that the lens is able to operate to take images while the light spectrum apparatus 3300 is attached to the mobile device, with the circular body 3302 surrounding the lens without covering any portion of the lens.

The light spectrum apparatus 3300 may be used in a similar manner to the lighting apparatus 3200 to introduce colored light onto the test strip. The light spectrum apparatus 3300 however may introduce a variety of colors without switching the lighting device attached to the mobile device. The light spectrum apparatus 3300 may allow for choosing which colored lights of the plurality of lights 3306 to activate. For example, only a primary color may be chosen to be activated, such as red lights, blue lights, or green lights present on the light spectrum apparatus 3300 may be activated, or different combinations may be activated. For example, a combination of red and blue lights may be activated to introduce a magenta color spectrum into the environment. In other embodiments, lights included in the plurality of lights 3306 may simply be magenta or some other non-primary color, without needing to combine different lights.

Figure 34:
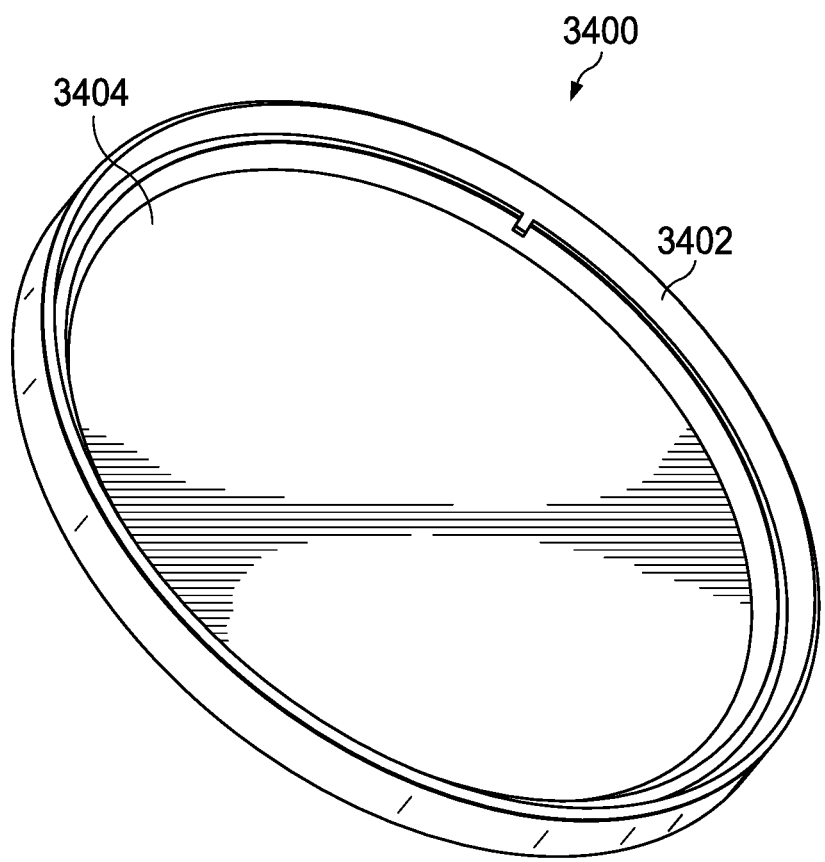
FIG. 34 illustrates an attachable color filter apparatus.

Referring now to FIG. 34, there is illustrated an attachable color filter apparatus 3400. The color filter apparatus 3400 may include a ringed body 3402 made of a material such as plastic. The ringed body 3402 has fixed within a colored filter 3404. The colored filter 3404 may be a plastic film or piece of thin glass that is a specific color, in order to absorb colors other than that specific color from light passing through the colored filter 3404. For example, if a magenta filter is used for the colored filter 3404, green light would be absorbed by the colored filer 3404. This may be combined with different wavelengths of light to analyze the results on a test strip.

In the same example of using a magenta filter, if white light is introduced, only blue and red light would be allowed through the magenta colored filter 3404, filtering out any green light. This may be useful in analyzing a test strip that provides red colored test and control line results, as the color temperatures of the test line and control line could then be compared, while filtering out other wavelengths of light. In other embodiments, other colored filters 3404 may be used, such as a blue filter. In the example where the test and control lines produce red results, a blue filter may allow for any red reflected from the test and control lines to be filtered out. This would produce a black result for the control line that could be compared against the test line results. If the test line results include some blue in the results, the blue wavelengths would still pass through the filter, indicating that the reaction of the test line was not as strong as the control line.

Traditional colorimetry techniques may be applied to the results obtained as described with respect to FIGS. 32-34. The resultant color of the test line as received by the camera allows for the specific wavelength of the color of the test line to be recorded, and then compared to previous wavelengths recorded in previous tests stored in the system disclosed herein, or compared to the wavelength of the control line. The chosen color may additionally have a known wavelength, with the captured wavelength of the light reflected from the test line and/or control line being compared to the known wavelength of the light or filter, to determine how much light was absorbed by the test line and control line. The wavelengths of the test line or control line in some embodiments may be approximated from the RGB values of the pixels captured in the image since wavelengths colors are known, thus assigning a wavelength value to the captured colors. In other embodiments, the mobile device may have colorimeter capabilities to detect the wavelength being returned to the mobile device. The colorimeter capabilities may be built into the mobile device, or a colorimeter peripheral may be added to the mobile device.

Figure 35:
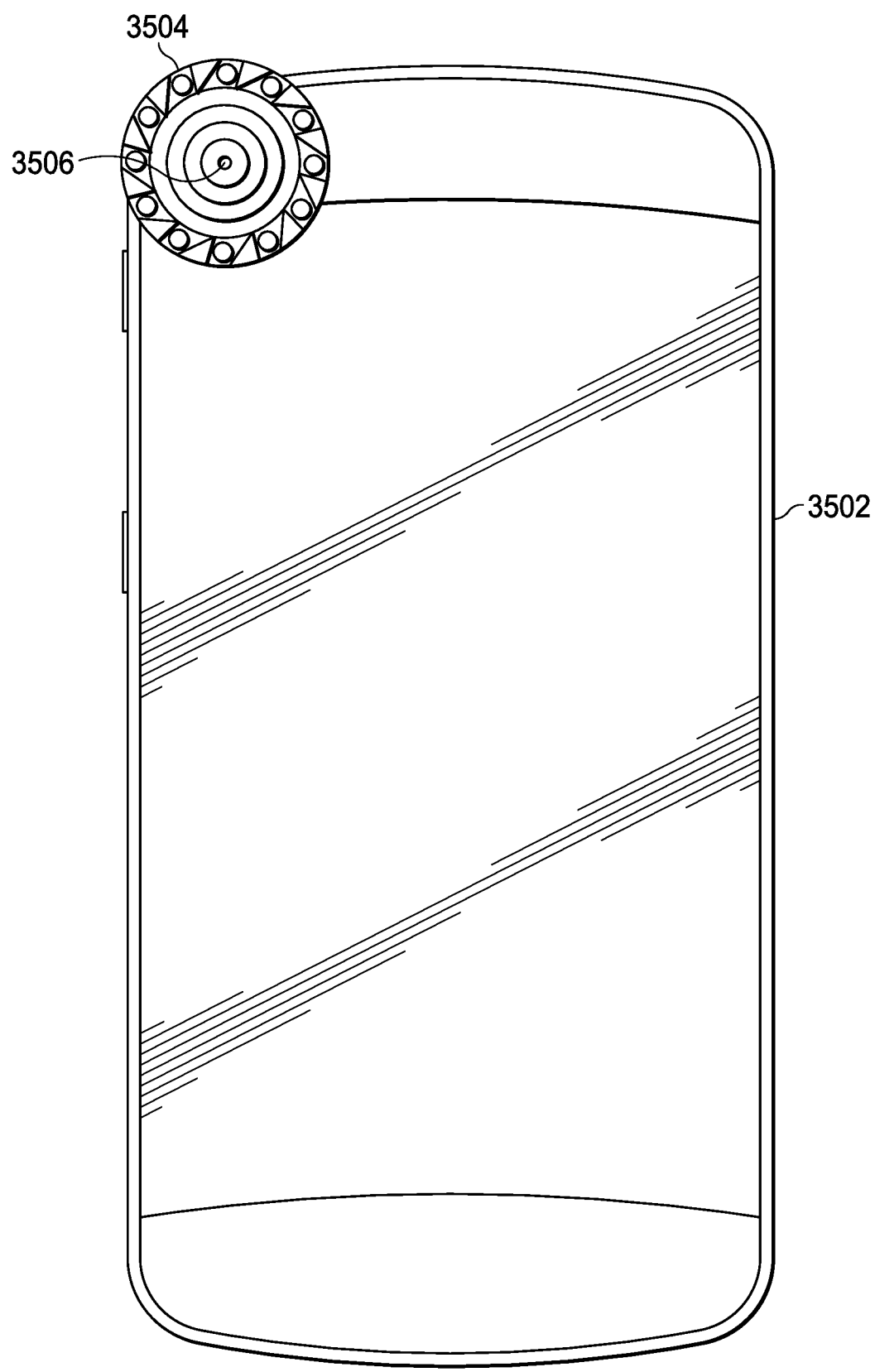
FIG. 35 illustrates a mobile device with a colorimetry device coupled thereto.

Referring now to FIG. 35, there is illustrated a mobile device 3502 with a colorimetry device 3504 coupled thereto. The colorimetry device 3504 is attached over a lens 3506 of the mobile device camera. The colorimetry device 3504 may be a lighting apparatus, such as lighting apparatus 3200 or the light spectrum apparatus 3300 described herein, or may be a colored filter such as the colored filter 3400 described herein. In the case of a light apparatus, there may be an aperture in the lighting apparatus such that the lens 3506 sits within the aperture, allowing the lens 3506 to still light and the camera to take images. In the case of a colored filter, the filter would cover the lens 3506 so that the effect of the colored filter is applied to light received by the lens 3506. In some embodiments, the colorimetry device 3504 may be fixed to the mobile device 3502 using an adhesive, a clip, or other methods.

Figure 36:
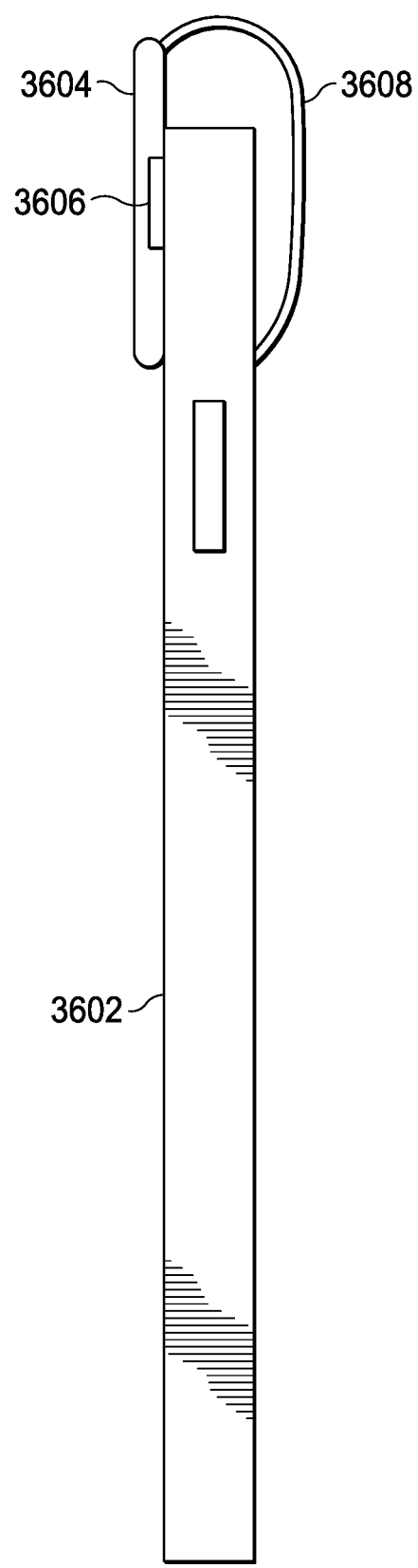
FIG. 36 illustrates a mobile device with a colorimetry device coupled thereto

Referring now to FIG. 36, there is illustrated a mobile device 3602 with a colorimetry device 3604 coupled thereto. The colorimetry device 3604 is attached over a lens 3606 of the mobile device camera. The colorimetry device 3604 may be a lighting apparatus, such as lighting apparatus 3200 or the light spectrum apparatus 3300 described herein, or may be a colored filter such as the colored filter 3400 described herein. In the case of a light apparatus, there may be an aperture in the lighting apparatus such that the lens 3606 sits within the aperture, allowing the lens 3606 to still light and the camera to take images. In the case of a colored filter, the filter would cover the lens 3606 so that the effect of the colored filter is applied to light received by the lens 3506. The colorimetry device 3604 may be fixed to the mobile device 3602 via a clip 3608 fixed to the colorimetry device 3604 and extending over the top of the mobile device 3602 to clamp against the back of the mobile device 3602. In some embodiments, the clip 3608 may be made of flexible metal material that can be flexed out and over the top of the mobile device 3602, but when pressure is taken off the clip 3608, the clip 3608 closes back to clamp against the mobile device 3602. Other embodiments may include types of clips, such as a clip including a wound spring that extends when the clip is squeezed and retracts to clamp onto the mobile device 3602.

Figure 37:
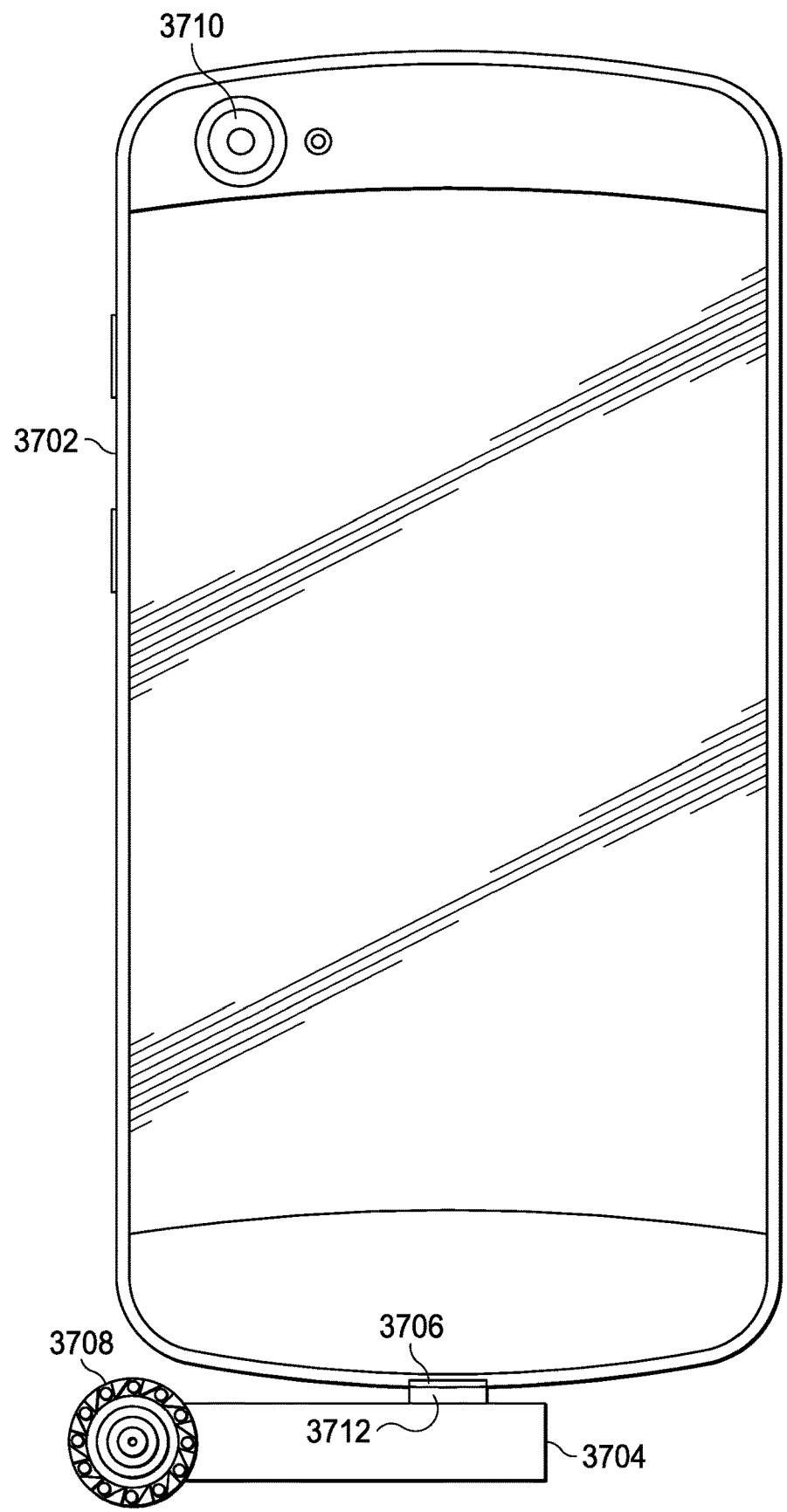
FIG. 37 illustrates a mobile device coupled to a colorimetry device via a charging port of the mobile device.

Referring now to FIG. 37, there is illustrated a mobile device 3702 coupled to a colorimetry device 3704 via a charging port 3706 of the mobile device 3702. The colorimetry device include a lighting apparatus 3708 situated at a first end of the colorimetry device 3704 and disposed to emit light in the same direction as a lens 3710 faces of the mobile 3702. At a second end of colorimetry device 3704 is a charging port connector 3712 configured to plug into the charging port 3706 of the mobile device 3702. The colorimetry device 3704 is supplied power via the charging port 3706 to operate the lighting apparatus 3708. This allows for the lens 3710 to either be free of any attachments, or for an attachment to be used over the lens 3710 at the same time as the lighting apparatus 3708, such as applying a colored filter over the lens 3710 at the same time as the colorimetry device 3704 is being used, to utilize both white or colored light and a colored filter at the same time.

Figure 38A:
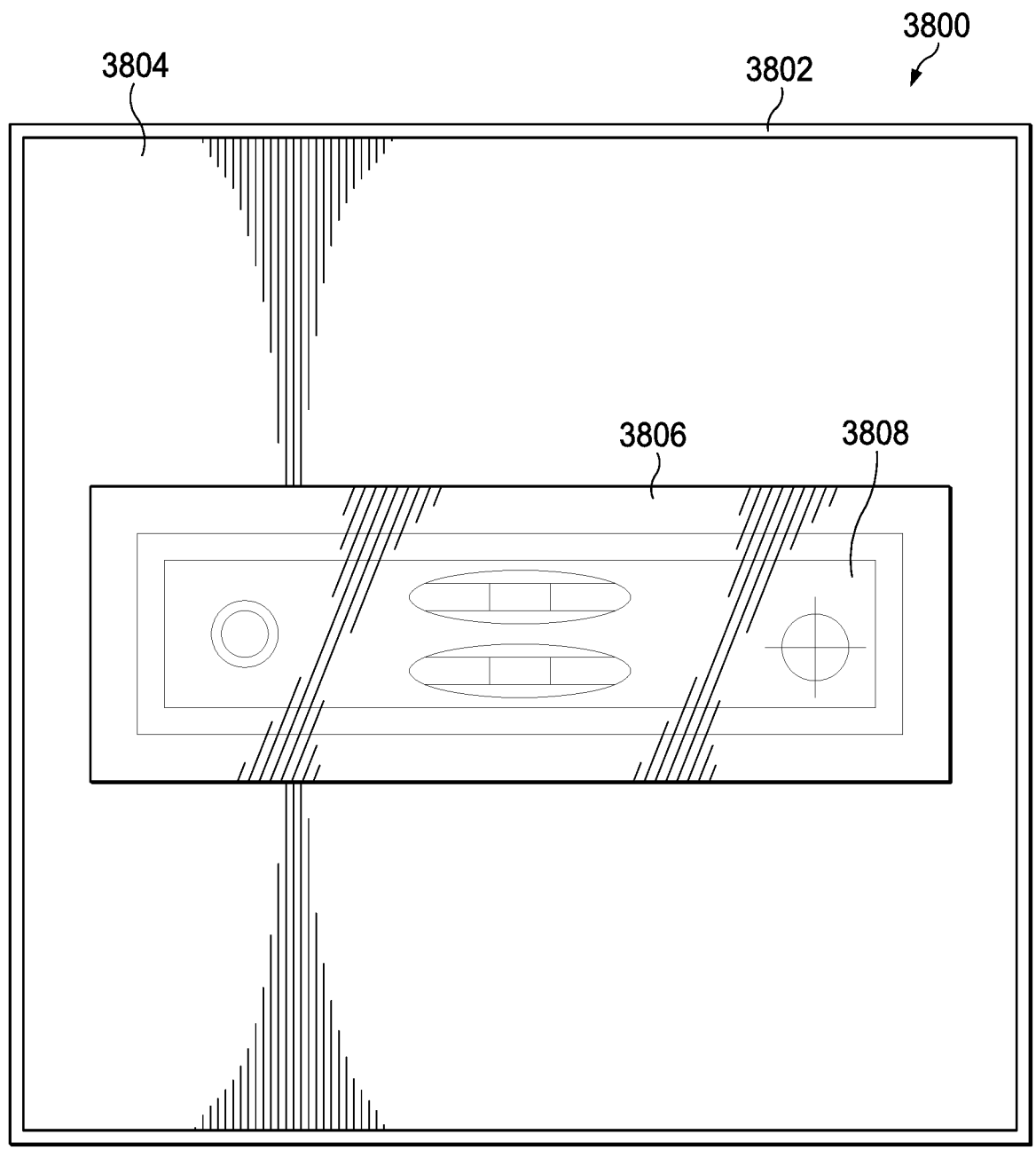
FIG. 38A illustrates a top view of a light box apparatus.
Figure 38B:
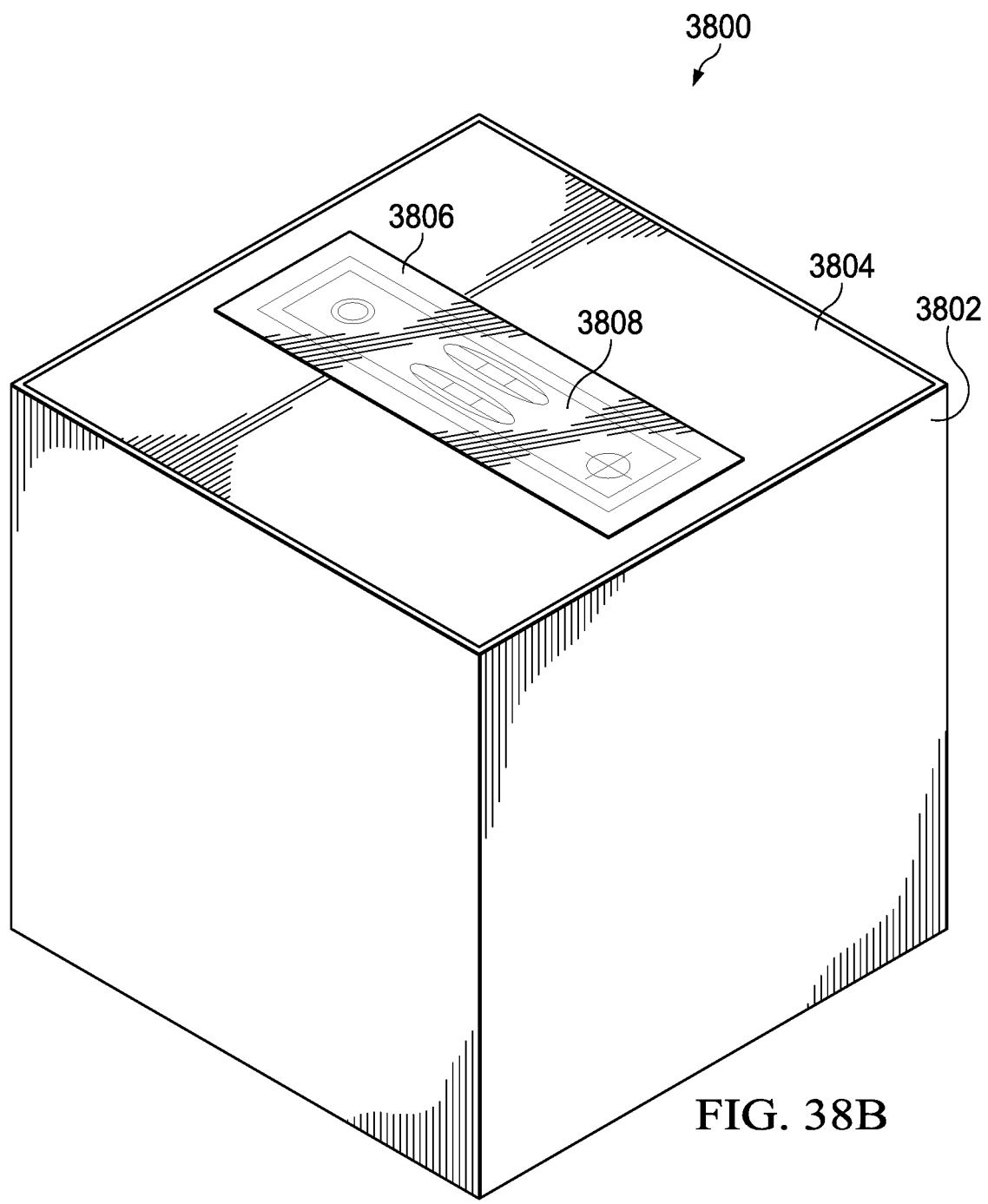
FIG. 38B illustrates a top perspective view of a light box apparatus.
Figure 38C:
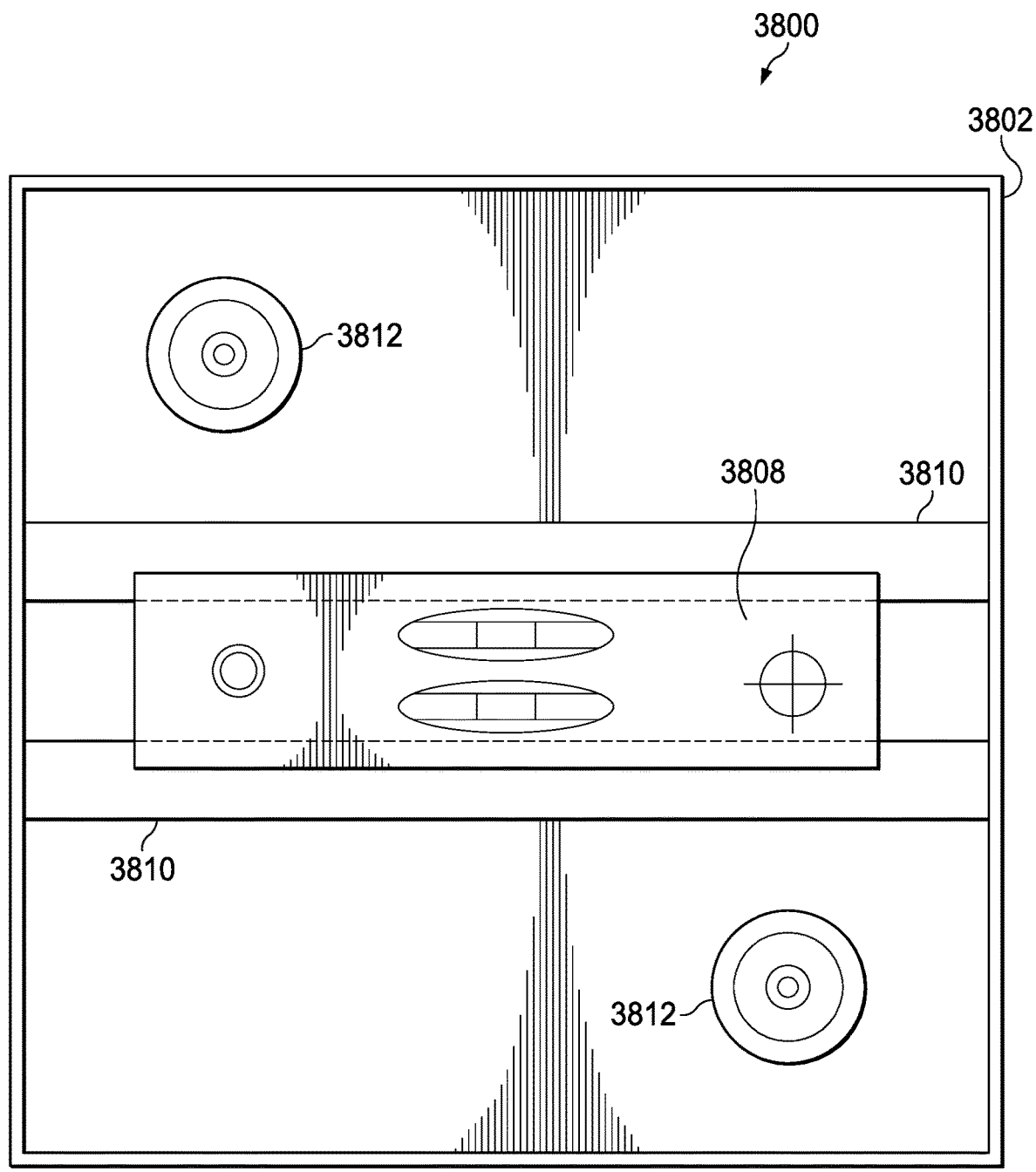
FIG. 38C illustrates a top view of a light box apparatus in an open state.
Figure 38D:
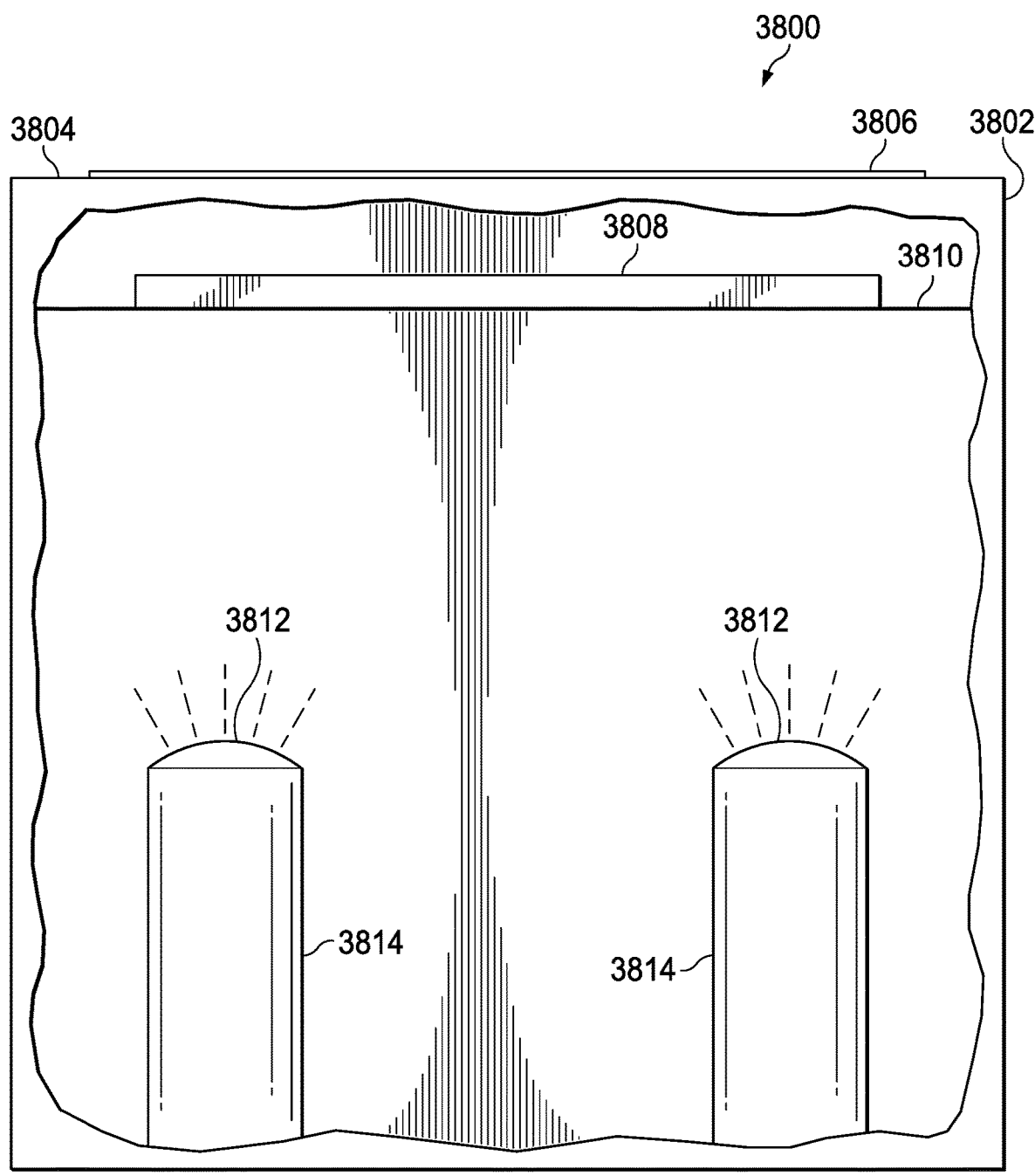
FIG. 38D illustrates a side cross sectional view of a light box apparatus.

Referring now to FIGS. 38A and 38B, there is illustrated a light box apparatus 3800. FIG. 38A illustrates a top view of the light box apparatus 3800 and FIG. 38B illustrates a top perspective view of the light box apparatus 3800. FIG. 38C illustrates the light box apparatus 3800 includes a top view of the light box apparatus 3800 in an open state. FIG. 38D illustrates a side cross sectional view of the light box apparatus 3800.

The light box apparatus 3800 serves the functions of controlling light outside of the light box apparatus 3800, while providing a separate lighting environment within the lighting box apparatus 3800. The light box apparatus 3800 has a cubic body 3802 having a substantially hollow interior. The light box apparatus 3800 may be made of plastic, cardboard, wood, or other materials. In some embodiments, the light box apparatus 3800 may be provided to a user in a folded or disassembled state, and the user might configure the box into the position shown in the accompanying drawings. A top panel 3804 of the light box apparatus 3800 includes a window 3806 through which a medical testing device 3808 may be viewed. The medical testing device 3808 may be disposed a distance down from the window 3806 and may rest on a platform within the light box apparatus 3800. The window 3806 may be a clear window, or the window 3806 may be a colored filter or film to allow for the filtering of colors when capturing an image of the medical testing device 3808, as described herein. The window 3806 may be made of plastic, glass, or other materials. A user may capture an image of the testing device 3808 by either holding a mobile device over the top panel 3804 of the light box apparatus 3800, or by placing the mobile device directly over the window 3806, in order to use the window as a colored filter, or to minimize light from the environment surrounding the outside of the light box apparatus 3800.

Referring now to FIGS. 38C and 38D, FIG. 38C illustrates a top view of the light box apparatus 3800 in an open state. FIG. 38D illustrates a side cross sectional view of the light box apparatus 3800. The medical testing device 3808 may reside on one or more platforms. As shown in FIG. 38C, the medical testing device 3808 is disposed on two shelves 3810 underneath each long edge of the medical testing device 3808. The two shelves 3810 allow for more light to envelope the medical testing device 3808 than a solid platform underneath the medical testing device 3808 would, since additional light can pass between the two shelves 3810.

Light is emitted from one or more lights 3812 disposed below the medical testing device 3808 and may sit on or be coupled to an interior bottom of the light box apparatus 3800. The light emitted from the one or more lights 3812 may white light, or colored light. Light is emitted from the one or more lights 3812 up from the bottom of the interior of the light box apparatus 3800 towards the top panel 3804 in order to illuminate the medical testing device 3808 from below and envelope the area with light, while avoiding casting light directly on the surface of the medical testing device 3808 so that the medical testing device 3808 is not totally washed out. The one or more lights 3812 may be arranged such that the light is spread evenly throughout the light box apparatus 3800, such as shown in FIGS. 38C and 38D, wherein the one or more lights are disposed at opposite corners of the light box apparatus 3800. The one or more lights 3812 may also be placed on platforms 3814 extending up from the bottom of the light box apparatus 3800, such as shown in FIG. 38D, in order to extend assist in focusing light emitted from the one or more lights towards the top of the light box apparatus 3800.

Figure 39:
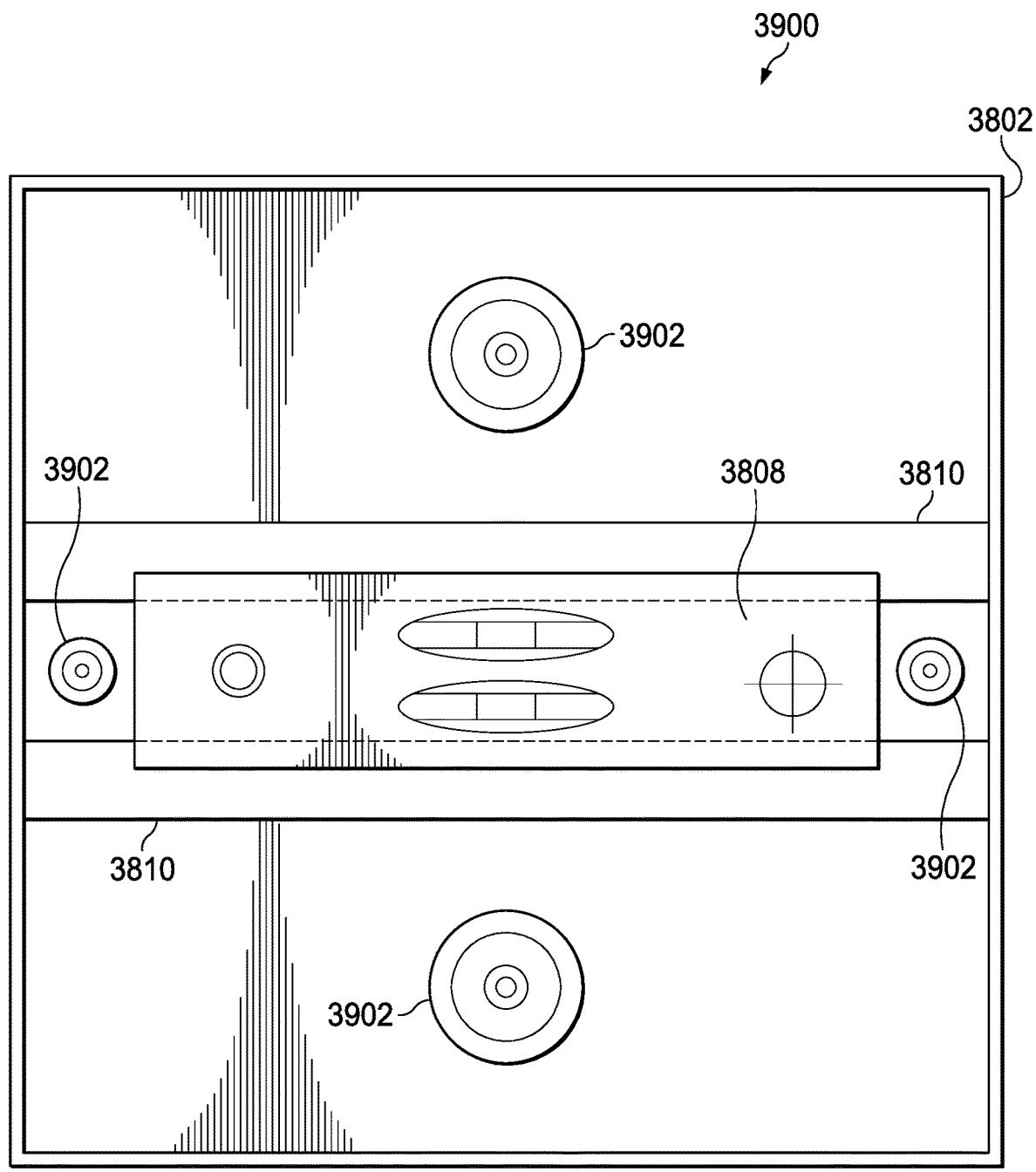
FIG. 39 illustrates a light box apparatus including a plurality of lights in an alternate configuration.

Referring now to FIG. 39, there is illustrated a light box apparatus 3900 including a plurality of lights 3902 in an alternate configuration. The plurality of lights 3902 are arranged such that two lights are each disposed near the center of a top and the center of a bottom edge, respectively, of the bottom surface of the light box apparatus 3900, and two other lights are each disposed near the center of a left and the center of a right edge, respectively, while also residing below the space between the shelves 3810. This embodiment allows for more light to be emitted throughout the light box apparatus.

Figure 40:
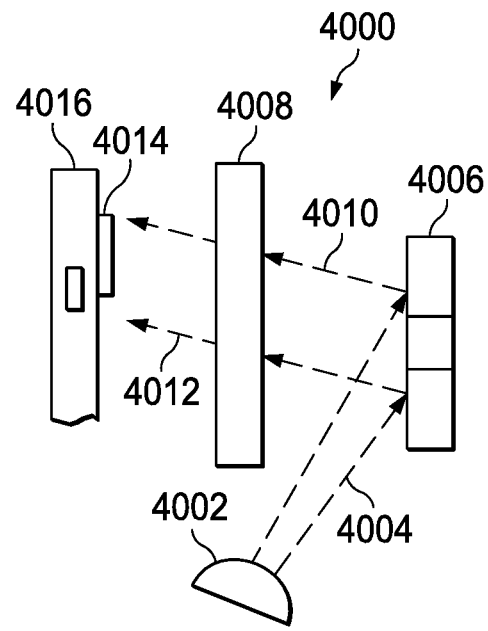
FIG. 40 illustrates a color wavelength detection arrangement.

Referring now to FIG. 40, there is illustrated a color wavelength detection arrangement 4000. There is illustrated a lighting apparatus 4002 directing light in a first wavelength 4004 onto a testing strip 4006. The light in the first wavelength 4004 is reflected off the testing strip 4006 towards a color filter 4008. The light reflected off the testing strip 4006 may be of a second wavelength 4010 corresponding to the color of the test line and/or the control line and the color reflected off the test line according to that color of the test line. After passing through the color filter 4008, the light may now be in a third wavelength 4012. The light in the third wavelength 4012 then reaches the lens 4014 of a mobile device 4016. The lens 4014 may also be a mobile device peripheral or other device for performing colorimeter functions.

Different comparisons may be made based on the arrangement 4000. For example, the light of the first wavelength 4004 may be compared against the light of the third wavelength 4012 to compare how much the wavelength changed between the first introduced light and the light finally captured by the lens 4014. The light of the second wavelength 4010 may also be compared against the light of the third wavelength 4012, to compare the light reflected off the testing strip 4006 against the light after being filtered by the color filter 4008.

Figure 41:
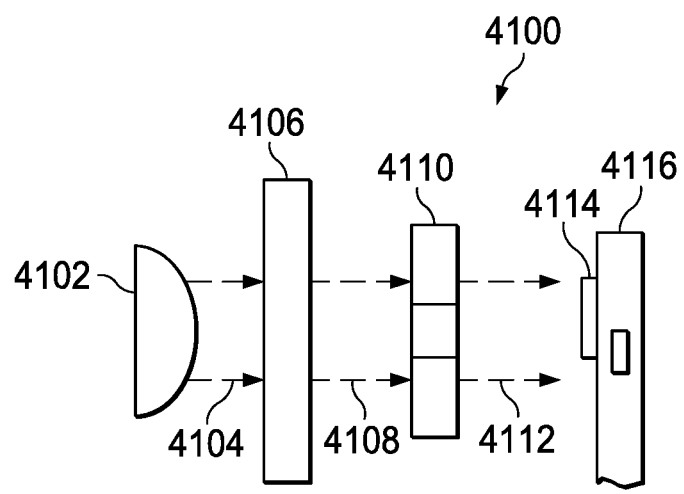
FIG. 41 illustrates a color wavelength detection arrangement.

Referring now to FIG. 41, there is illustrated a color wavelength detection arrangement 4100. There is illustrated a lighting apparatus 4102 directing light in a first wavelength 4104 through a color filter 4106. After passing through the color filter 4106, the light may be in a second wavelength 4108. The light in the second wavelength 4108 is reflected off a testing strip 4110. The light reflected off the testing strip 4110 may be of a third wavelength 4112 corresponding to the color of the test line and/or the control line and the color reflected off the test line according to that color of the test line, and having already been filtered by the color filter 4106. The light of the third wavelength 4112 then reaches a lens 4114 of a mobile device 4116. The lens 4114 may also be a mobile device peripheral or other device for performing colorimeter functions, such as a color sensor peripheral connected to the mobile device.

The lighting apparatus 4102 may pass white light through the color filter 4106, altering the wavelength for use with the arrangement 4100. After the light passes through the color filter 4106, the light of the second wavelength 4108 is altered by the color reflecting off the color of the test line and control line, which creates the third wavelength 4112. Since the wavelength produced by a particular color filter may be known, the captured wavelength (the third wavelength 4112) may be compared to the known second wavelength 4108. The differences between the wavelength and the amount of light absorbed by the color of the test line. The absorbance by the test line may be directly proportional to the concentration of the bound substance on the test line, indicating whether a strong reaction has occurred or not. For example, if the difference between the wavelengths is small, a weak reaction has occurred. However, if there is a large difference between the wavelengths, this may indicate a strong reaction, and thus a high likelihood of infection or other condition.

Figure 42:
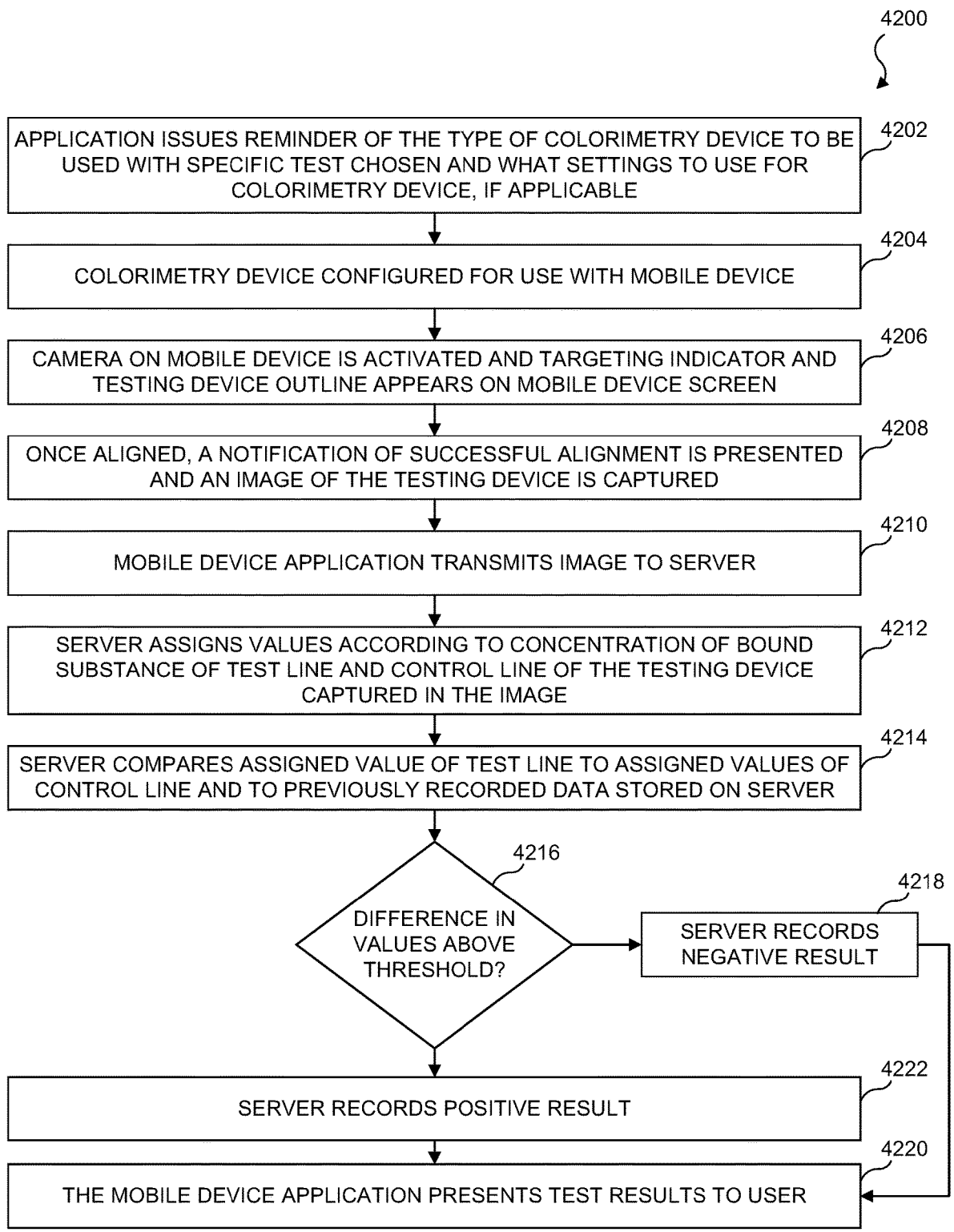
FIG. 42 illustrates a flowchart of a mobile device colorimetry analysis process.

Referring now to FIG. 42, there is illustrated a flowchart of a mobile device colorimetry analysis process 4200. At step 4202, after selection of a test to be performed using an application on a mobile device, the application issues a reminder of the type of colorimetry device to be used or that is recommended to be used with the selected test, and what settings to use for the colorimetry device. For example, the application may suggest using a filter of a particular or to configure a lighting apparatus to emit light of a particular color or colors. At step 4204, the colorimetry device is configured for use with the mobile device based on the setting recommended. Step 4204 may also include attaching the colorimetry device to the mobile device. At step 4206, a camera on the mobile device is activated and a crosshair indicator and a testing device outline appear on the mobile device screen. At step 4208 the crosshair indicator presented on the screen of the mobile device is aligned with a crosshair icon on the testing device and the device outline presented on the screen of the mobile device is aligned with the borders of a testing device, and, once aligned, an indicator of successful alignment is presented on the screen and an image of the testing device is captured by the mobile device camera. At step 4210, the application transmits the captured image to a server.

At step 4212, the server assigns values to the captured test line and control line. The values may correspond to a detected wavelength or other indication of color according to the bound substance concentration. The server may additionally store the value of the initial wavelength of light emitted by a lighting apparatus and used in the test. The server may also store in association with the test a wavelength according to a wavelength of light after having passed through a colored filter for the test. At step 4214, the server compares the assigned value associated with the test line to the control line and to other data such as the wavelength of the light before encountering the control line, or known values from previous tests, either by the user or other users, etc.

At decision block 4216, it is determined whether the difference between the compared values is above a threshold. For instance, a threshold value may be assigned for the change in wavelength between light cast onto the testing device and light reflected off the test line. If the difference is below the threshold, the process 4200 flows to step 4218, where the server records a negative test result, indicating no infection or other medical condition. The process then flows to step 4220, where the negative result is presented to the user via the mobile device application. If at decision block 4216 the difference between the values is above the threshold, the process flows to step 4222 where the server records a positive result, indicating an infection or other medical condition. The process flows from step 4222 to step 4220 to present the positive test result to the user. The test result provided to the user may be either a qualitative or quantitative result.

Figure 43:
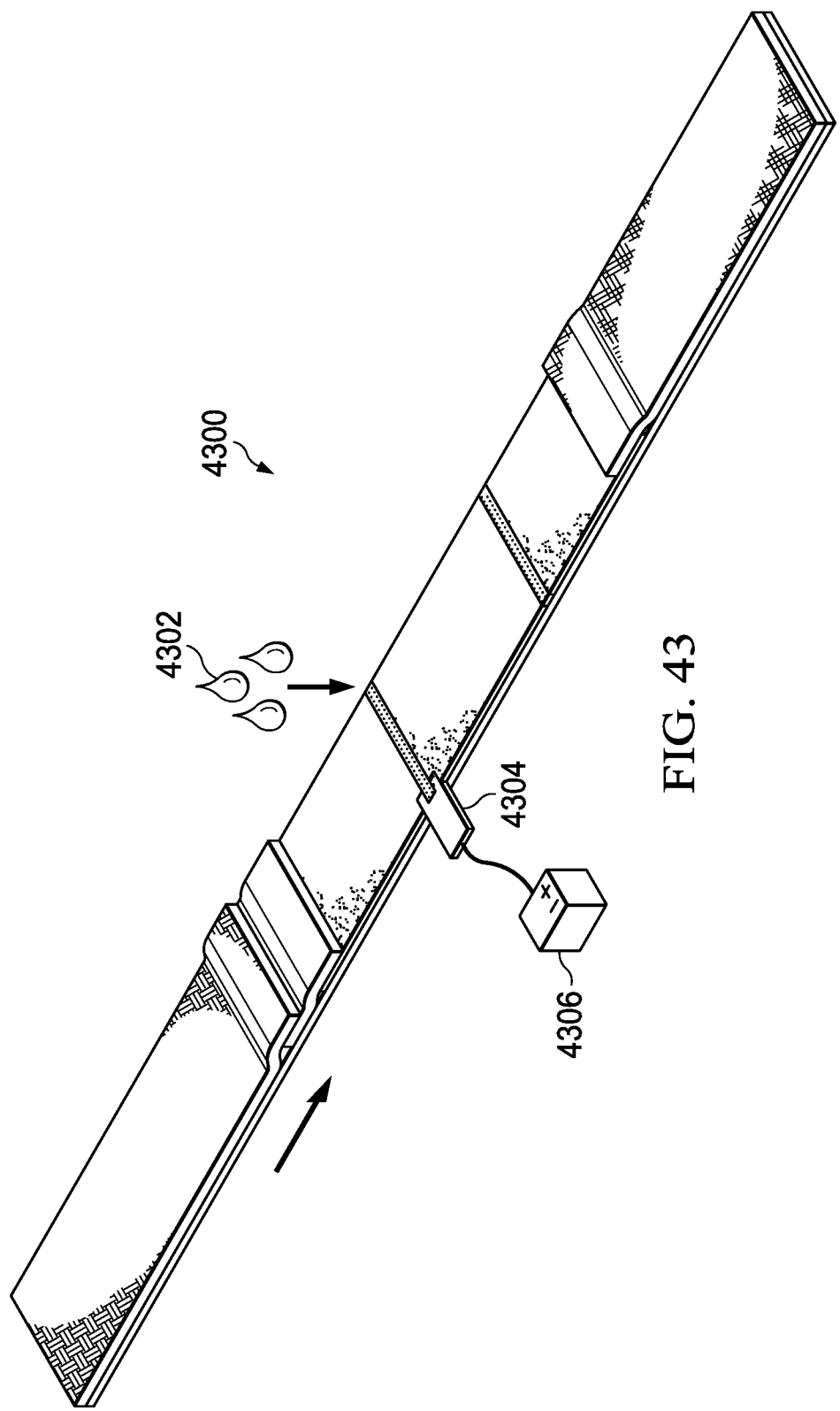
FIG. 43 illustrates an immunoassay test strip including fluorescent dye indicators.

Referring now to FIG. 43, there is illustrated an immunoassay test strip 4300 including fluorescent dye indicators 4302. The fluorescent dye indicators 4302 may be introduced to provide for a fluorescent immunoassay technique to be applied to the test strip 4300 in order to allow for ratiometric and non-ratiometric analyzation of bound and unbound antibodies, antigens, etc. Various fluorescent dyes are available for use, depending on the type of condition being tested, such as the AF488 or Alexa 488 dye (bright green fluorescent dye). The type of dye uses is also dependent on whether ratiometric or non-ratiometric analysis is to be performed. The fluorescent dye or fluorescent compound may absorb light or energy (excitation light or energy) at a specific wavelength and then emit light or energy at a different wavelength (emission light or energy). If the antibodies and antigens are bound, the fluorescence of the dye will increase or shift noticeably. The difference between the wavelength of the excitation light and the emission light is called the Stokes shift. The greater the shift or difference in the wavelength the less interference there will be by having the excitation light detected as part of the emission light.

The test strip 4300 also includes a conductive electrode sheet 4304 coupled to the test line to provide an electric charge to the antibodies and antigens on the test line during a test. The conductive electrode sheet 4304 may be coupled to a batter 4306 for power. The battery may be housed in a testing device and may provide power for a plurality of test strips. In other embodiments, the sheet 4304 may a fully functioning electrode capable of providing a charge without a battery. An electrical charge may be introduced to provide additional excitation of the antibodies and antigens present on the test line to, which causes certain antibodies or antigens to move towards the charge in order to separate out molecules, which may be useful in observing bound vs. free molecules on the test line.

Figure 44A:
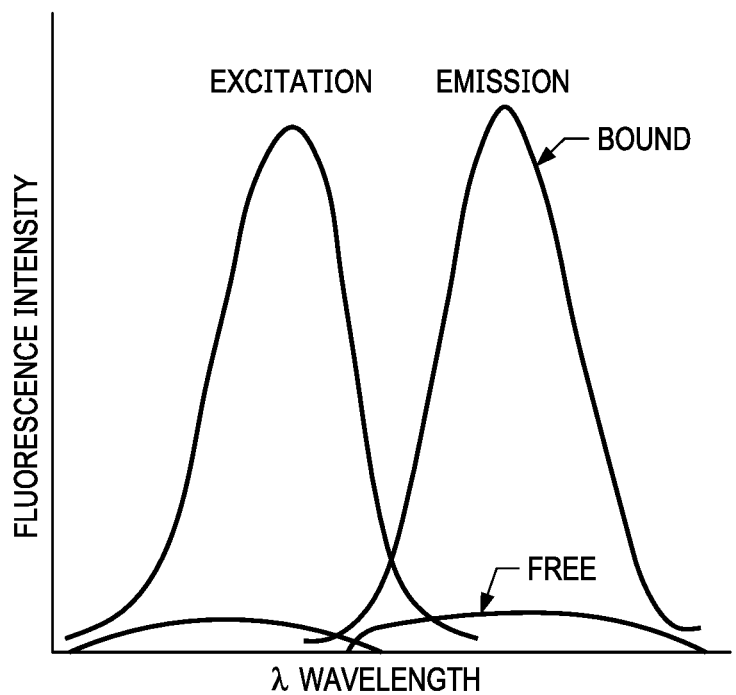
FIG. 44A illustrates a chart showing wavelength and fluorescence intensity of free and bound subjects according to non-ratiometric methods.
Figure 44B:
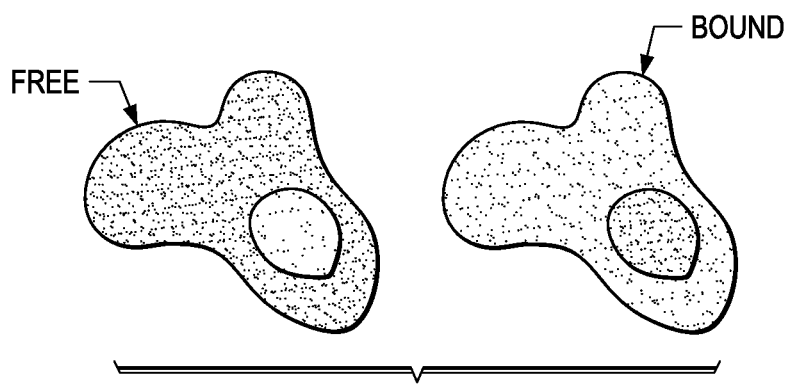
FIG. 44B illustrates a comparison of a free and a bound subject according to non-ratiometric methods.

Referring now to FIGS. 44A, 44B, 45A, 45B, and 45C, ratiometric and non-ratiometric methods of analyzing the results of an immunoassay test may be performed. In addition to processes described herein, an indicator such as a fluorescent dye may be used in ratiometric and non-ratiometric measurements. Indicators used for non-ratiometric measurements show a shift in fluorescent intensity, with the free indicator usually having a very weak fluorescence, as illustrated in FIGS. 44A and 44B. As shown in FIGS. 44A and 44B (non-ratiometric), the wavelengths of the free antibodies for both excitation and emission light have very low fluorescence intensity, whereas the excitation and emission light of bound antibodies result in high fluorescence intensity. Non-ratiometric measurements thus are useful in showing a stark difference between free and bound subjects, but not as useful for making minute comparisons.

Figure 45A:
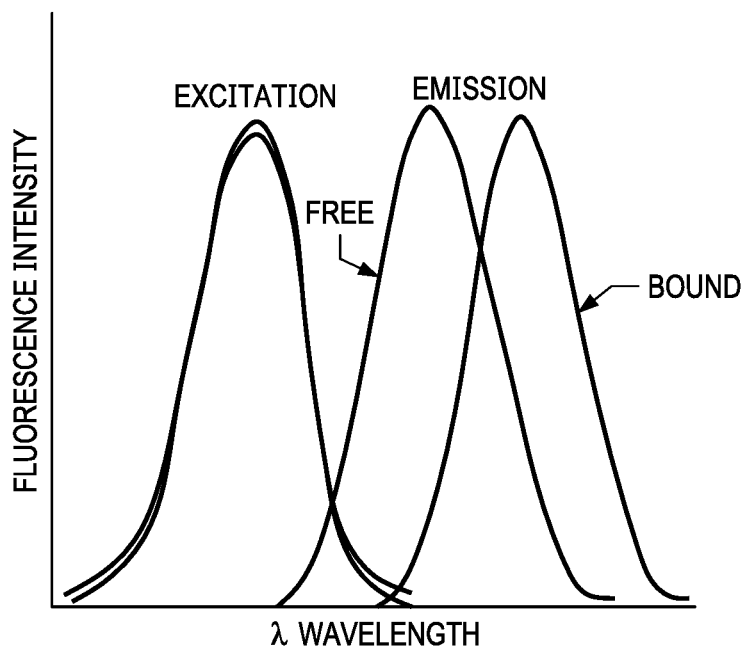
FIG. 45A illustrates a chart showing wavelength and fluorescence intensity of free and bound subjects according to ratiometric methods.
Figure 45B:
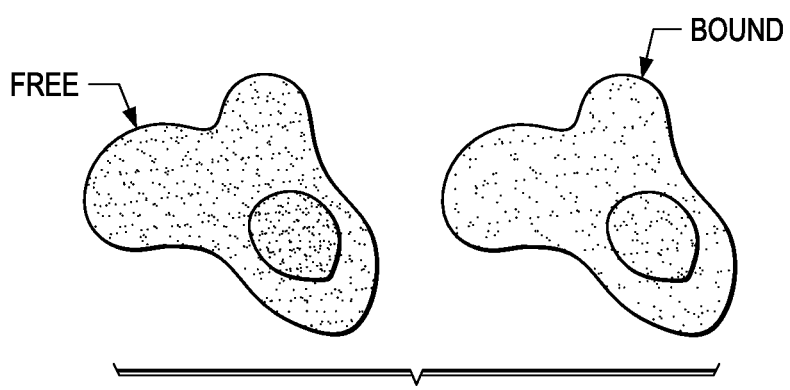
FIG. 45B illustrates a comparison of a free and a bound subject according to ratiometric methods.
Figure 45C:
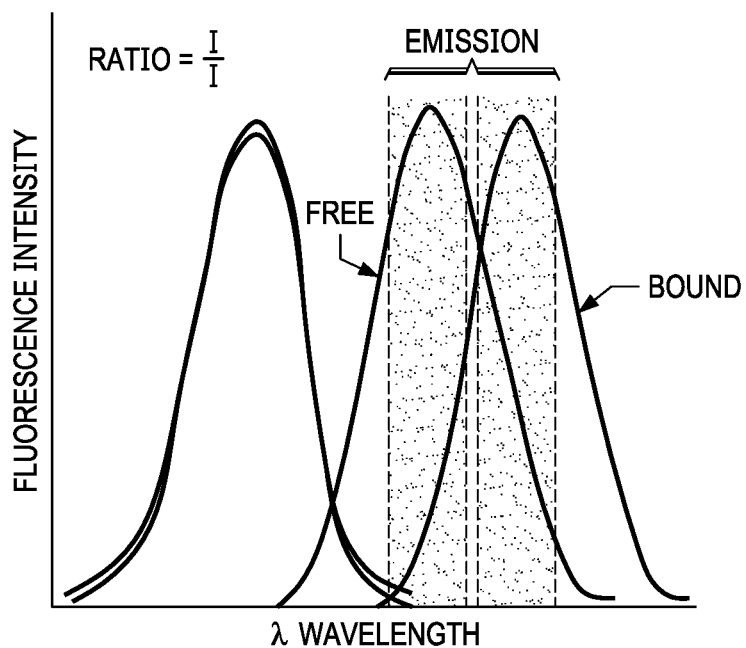
FIG. 45C illustrates a chart showing a ratio applied to fluorescence intensity of free and bound subjects.

For ratiometric measurements, such as shown in FIGS. 45A and 45B, both the excitation and emission light for both free and bound subjects emit a high fluorescent intensity. Excitation light on the free and bound subjects has close result, as shown in FIG. 45A, but the emission light results in a shift of the wavelength for the bound subjects, such that the bound subjects undergo a color shift, as shown in FIG. 45B, for example. The changes in color allow for a ratiometric analysis of the two emission wavelengths, such as shown in FIG. 45C. This ratio of the free emission wavelength to the bound emission wavelength may thus be used in analyzing test results of a immunoassay test. If the shift is a large shift from the free emission wavelength, a strong positive result for infection or other medical condition may be indicated.

Figure 46:
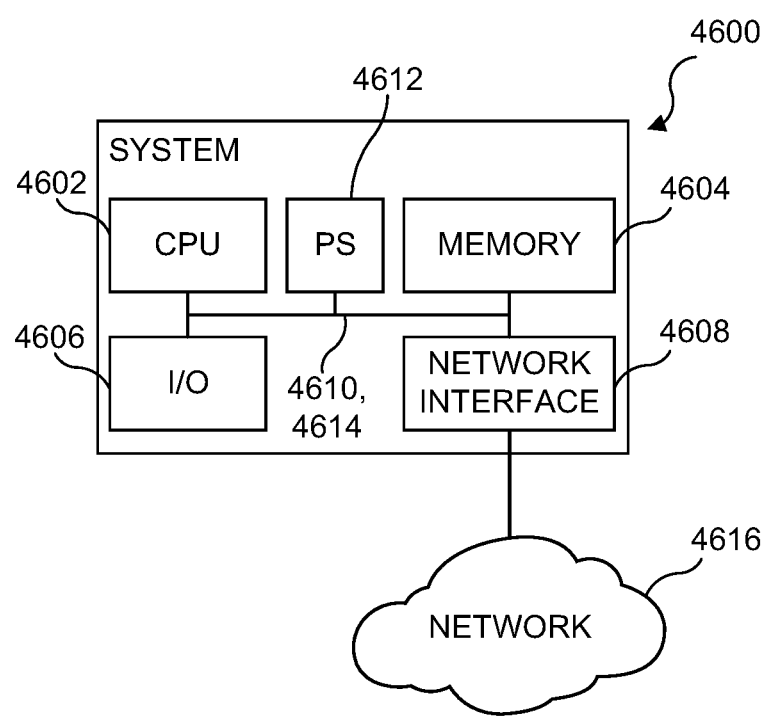
FIG. 46 illustrates a diagrammatic view of one embodiment of a system device that may be used within the environment described herein

Referring to FIG. 46, one embodiment of a system device 4600 is illustrated. The system device 4600 is one possible example of a mobile device as described herein, a colorimetry device as described herein, or one possible example of a remote server as described herein. Embodiments include cellular telephones (including smart phones), personal digital assistants (PDAs), netbooks, tablets, laptops, desktops, workstations, telepresence consoles, and any other computing device that can communicate with another computing device using a wireless and/or wireline communication link. Such communications may be direct (e.g., via a peer-to-peer network, an ad hoc network, or using a direct connection), indirect, such as through a server or other proxy (e.g., in a client-server model), or may use a combination of direct and indirect communications. It is understood that the device may be implemented in many different ways and by many different types of systems, and may be customized as needed to operate within a particular environment.

The system 4600 may include a controller (e.g., a central processing unit ("CPU")) 4602, a memory unit 4604, an input/output ("I/O") device 4606, and a network interface 4608. The components 4602, 4604, 4606, and 4608 are interconnected by a transport system (e.g., a bus) 4610. A power supply (PS) 4612 may provide power to components of the computer system 4600, such as the CPU 4602 and memory unit 4604, via a power system 4614 (which is illustrated with the transport system 4610 but may be different). It is understood that the system 4600 may be differently configured and that each of the listed components may actually represent several different components. For example, the CPU 4602 may actually represent a multi-processor or a distributed processing system; the memory unit 4604 may include different levels of cache memory, main memory, hard disks, and remote storage locations; the I/O device 4606 may include monitors, keyboards, and the like; and the network interface 4608 may include one or more network cards providing one or more wired and/or wireless connections to a network 4616. Therefore, a wide range of flexibility is anticipated in the configuration of the computer system 4600.

The system 4600 may use any operating system (or multiple operating systems), including various versions of operating systems provided by Microsoft (such as WINDOWS), Apple (such as Mac OS X), UNIX, and LINUX, and may include operating systems specifically developed for handheld devices, personal computers, servers, and embedded devices depending on the use of the system 4600. The operating system, as well as other instructions, may be stored in the memory unit 4604 and executed by the processor 4602. For example, the memory unit 4604 may include instructions for performing some or all of the methods described herein.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system for providing colorimetric and ratiometric comparison and quantification for medical test results, comprising:
   a testing device including thereon an alignment target and including a plurality of immunoassay test strips, the plurality of immunoassay test strips each including:
      a sample pad capable of receiving a biologic sample;
      a conjugate pad containing particles for conjugating with antibodies or antigens present in the biologic sample; and
      a membrane strip including a test line and a control line, wherein the test line and the control line are viewable;
   a colorimetry device configured to operate with a mobile device, wherein the colorimetry device includes:

one or more light sources configured to emit a first wavelength of light onto at least the test line of at least one of the plurality of immunoassay test strips, and a color filter disposed between the testing device and the mobile device, wherein the color filter includes a clamp that presses against a back of the mobile device to maintain the color filter over a lens of a camera of the mobile device;

the mobile device including a viewing screen and a software application stored thereon, wherein the software application provides executable instructions to:

receive a selected test from among a plurality of test options;

issue a notification concerning use of the colorimetry device and instructions regarding configuration of the colorimetry device, for display to a user on the viewing screen, wherein the notification includes information particular to the selected test and a recommendation for configuring the colorimetry device for use with the selected test;

initiate operation of the camera of the mobile device;

present on the viewing screen of the mobile device an alignment graphic to be aligned with the alignment target of the testing device;

detect when an alignment of the alignment graphic and the alignment target has taken place;

capture an image of the testing device in response to detecting the alignment of the alignment graphic and the alignment target, including receiving, by the camera, a second wavelength of light, different from the first wavelength of light, that is passed through the color filter after reflection off the at least one of the plurality of immunoassay test strips;

detect color properties of a color of the test line and a color of the control line of at least one of the plurality of immunoassay test strips;

transmit the image and the color properties to a server;

determine a risk value for each of at least one disease risk tested using the biologic sample, wherein the risk value is a rating determined from the color properties of the color of the test line; and provide medical test results based on the risk value.

2. The system of claim 1, wherein the colorimetry device includes a light apparatus configured to emit a light of a predefined color onto the testing device.

3. The system of claim 1, wherein the colorimetry device includes a light box apparatus, wherein the light box apparatus includes:

a body, wherein the one or more light sources are disposed within the body;

a platform for placing the testing device; and a window disposed over the platform on a top panel of the body for viewing the testing device.

4. The system of claim 3, wherein the step of capturing the image includes disposing the mobile device over the window of the light box apparatus.

5. The system of claim 4, wherein the window of the light box apparatus includes the color filter.

6. The system of claim 1, wherein the software application further provides executable instructions to:

assign values to the first wavelength of light and the second wavelength of light; and determine whether a color shift occurred between the first wavelength of light and the second wavelength of light based on the assigned values.

7. The system of claim 1, wherein at least one of the plurality of immunoassay test strips includes one or more fluorescent dye indicators.

8. The system of claim 1, wherein the test line of one of the plurality of immunoassay test strips includes Zika virus antigens and the test line of another one of the plurality of immunoassay test strips includes an antibodies suitable for binding with hCG.

9. The system of claim 1, wherein a third wavelength of light is reflected off the at least one of the plurality of immunoassay test strips and is received by the color filter.

* * * * *